(12) United States Patent
Turner et al.

(10) Patent No.: US 11,067,562 B2
(45) Date of Patent: Jul. 20, 2021

(54) METHOD OF SEQUENCING MULTIPLE COPIES OF A SEQUENCE IN A CIRCULAR TEMPLATE

(71) Applicant: Pacific Biosciences of California, Inc., Menlo Park, CA (US)

(72) Inventors: Stephen Turner, Eugene, OR (US); Benjamin Flusberg, Atlanta, GA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 152 days.

(21) Appl. No.: 16/575,063

(22) Filed: Sep. 18, 2019

(65) Prior Publication Data
US 2020/0141918 A1    May 7, 2020

Related U.S. Application Data

(63) Continuation of application No. 15/654,395, filed on Jul. 19, 2017, now Pat. No. 10,481,144, which is a
(Continued)

(51) Int. Cl.
*C12Q 1/68*     (2018.01)
*B82Y 5/00*    (2011.01)
(Continued)

(52) U.S. Cl.
CPC ......... *G01N 33/48721* (2013.01); *B82Y 5/00* (2013.01); *B82Y 15/00* (2013.01);
(Continued)

(58) Field of Classification Search
CPC ....... G01N 33/48721; G01N 27/44791; C12Q 1/68; C12Q 1/6869; C12Q 2565/631; B82Y 5/00
See application file for complete search history.

(56) References Cited

U.S. PATENT DOCUMENTS

| 4,720,786 A | 1/1988 | Hara |
| 5,748,491 A | 5/1998 | Allison et al. |

(Continued)

FOREIGN PATENT DOCUMENTS

| EP | 1712909 A1 | 10/2006 |
| WO | 2000028312 A1 | 5/2000 |

(Continued)

OTHER PUBLICATIONS

Astier et al. "Toward Single Molecule DNA Sequencing: Direct Identification of Ribonucleoside andd Deoxyribonucleoside 5'-Monophosphates by Using an Engineered Protein Nanopore Equipped with a Molecular Adapter" JACS (2006) 128:1705-1710.
(Continued)

*Primary Examiner* — Brian J. Sines
(74) *Attorney, Agent, or Firm* — Robert H. Reamey

(57) ABSTRACT

The invention relates to methods for nanopore sequencing. A substrate such as a semiconductor is provided having a nanopore or an array of nanopores connecting an upper solution with a lower solution. A polymerase-nucleic acid complex comprising a strand displacing DNA polymerase and a circular nucleic acid template and components required for DNA synthesis are provided. The polymerase produces a nascent DNA strand complementary to the circular nucleic acid template and this nascent strand is translocated through the nanopore while it is being produced by a polymerase-nucleic acid complex comprising a strand displacing DNA polymerase and a circular nucleic acid template and providing the components required for DNA synthesis whereby the polymerase produces a nascent DNA strand which is translocated through the nanopore while the nascent DNA strand is being produced. The sequence of the nascent DNA strand is determined while it translates through the pore using the measured current over time. The poly-
(Continued)

merase proceeds around the circular template and continues to produce the nascent DNA strand such that a sequence in the nascent strand corresponding a sequence in the circular template is determined more than once. Determining the sequence of corresponding to the circular template more than once can provide for greater accuracy.

26 Claims, 33 Drawing Sheets

Related U.S. Application Data continuation of application No. 15/439,497, filed on Feb. 22, 2017, now Pat. No. 9,772,323, which is a continuation of application No. 15/337,312, filed on Oct. 28, 2016, now abandoned, which is a continuation of application No. 14/026,906, filed on Sep. 13, 2013, now Pat. No. 9,546,400, which is a continuation of application No. 12/757,789, filed on Apr. 9, 2010, now Pat. No. 8,986,928.

(60) Provisional application No. 61/168,431, filed on Apr. 10, 2009.

(51) Int. Cl.
  G01N 33/487 (2006.01)
  C12Q 1/6869 (2018.01)
  G01N 27/447 (2006.01)
  C12Q 1/6874 (2018.01)
  B82Y 15/00 (2011.01)

(52) U.S. Cl.
  CPC ......... *C12Q 1/6869* (2013.01); *C12Q 1/6874* (2013.01); *G01N 27/447* (2013.01); *G01N 27/44791* (2013.01); *C12Q 2565/631* (2013.01)

(56) References Cited

U.S. PATENT DOCUMENTS

| | | | |
|---|---|---|---|
| 5,795,782 | A | 8/1998 | Church et al. |
| 6,015,714 | A | 1/2000 | Baldarelli et al. |
| 6,056,922 | A | 5/2000 | Ikamatsu |
| 6,362,002 | B1 | 3/2002 | Denison et al. |
| 6,627,067 | B1 | 9/2003 | Branton et al. |
| 6,673,615 | B2 | 1/2004 | Denison et al. |
| 7,211,789 | B2 | 5/2007 | Berstis |
| 7,258,838 | B2 | 8/2007 | Li et al. |
| 7,312,046 | B2 | 12/2007 | Chin et al. |
| 7,476,503 | B2 | 1/2009 | Turner et al. |
| 7,488,671 | B2 | 2/2009 | Corderman et al. |
| 7,504,058 | B1 | 3/2009 | Batten et al. |
| 7,625,701 | B2 | 12/2009 | Williams et al. |
| 8,133,672 | B2 | 3/2012 | Bjornson et al. |
| 8,324,914 | B2 | 12/2012 | Chen et al. |
| 8,652,779 | B2 | 2/2014 | Turner et al. |
| 8,986,928 | B2 | 3/2015 | Turner et al. |
| 9,546,400 | B2 | 1/2017 | Turner et al. |
| 9,551,028 | B2 * | 1/2017 | Bjornson ............ C12Q 1/6869 |
| RE47,067 | E | 10/2018 | Turner et al. |
| 2002/0197618 | A1 | 12/2002 | Sampson |
| 2003/0207326 | A1 | 11/2003 | Su et al. |
| 2003/0232346 | A1 | 12/2003 | Su |
| 2004/0144658 | A1 | 7/2004 | Flory |
| 2005/0202444 | A1 | 9/2005 | Zhu |
| 2005/0266416 | A1 | 12/2005 | Guo |
| 2006/0019247 | A1 | 1/2006 | Su et al. |
| 2006/0063171 | A1 | 3/2006 | Akeson et al. |
| 2006/0231419 | A1 | 10/2006 | Barth et al. |
| 2006/0246497 | A1 | 11/2006 | Huang et al. |
| 2007/0048745 | A1 | 3/2007 | Joyce et al. |
| 2007/0099191 | A1 | 5/2007 | Nair et al. |
| 2007/0205098 | A1 | 9/2007 | Ehrismann et al. |
| 2007/0298511 | A1 | 12/2007 | Kang et al. |
| 2008/0041733 | A1 | 2/2008 | Hibbs et al. |
| 2008/0218184 | A1 | 9/2008 | Henry et al. |
| 2008/0254995 | A1 | 10/2008 | Kim et al. |
| 2008/0311582 | A1 | 12/2008 | Bayley et al. |
| 2009/0029477 | A1 | 1/2009 | Meller et al. |
| 2009/0286245 | A1 | 11/2009 | Bjornson et al. |
| 2009/0298072 | A1 | 12/2009 | Ju |
| 2010/0092960 | A1 | 4/2010 | Fehr |
| 2010/0289505 | A1 | 11/2010 | Zhang et al. |
| 2010/0331194 | A1 | 12/2010 | Turner et al. |
| 2011/0014612 | A1 | 1/2011 | Hendricks et al. |
| 2011/0081647 | A1 | 4/2011 | Siddiqi et al. |
| 2011/0193570 | A1 | 8/2011 | Chen et al. |
| 2011/0214991 | A1 | 9/2011 | Kim et al. |
| 2012/0055792 | A1 | 3/2012 | Gundlach et al. |
| 2012/0107802 | A1 | 5/2012 | Stoddart et al. |
| 2014/0051069 | A1 | 2/2014 | Jayasinghe et al. |
| 2019/0187094 | A1 | 6/2019 | Reid et al. |

FOREIGN PATENT DOCUMENTS

| | | |
|---|---|---|
| WO | 2006020775 A2 | 2/2006 |
| WO | 2008102121 A1 | 8/2008 |
| WO | 2009077734 A2 | 6/2009 |
| WO | 2010086603 A1 | 8/2010 |
| WO | 2012083249 A2 | 6/2012 |
| WO | 2012083249 A3 | 6/2012 |

OTHER PUBLICATIONS

Austin et al. "Fabrication of 5nm linewidth and 14 nm pitch features by nanoimprint lithography" Apps Phys Lett (2004) 84(26):5299-5301.
Bayley et al. "Nanotechnology: Holes with an edge" Nature (2010) 567:164-165.
Benner et al. "Sequence-specific detection of individual DNA polymerase complexes in real time using a nanopore" NNano (2007) 2:718-724.
Branton et al. "The potential and challenges of nanopore sequencing" Nat Biotech (2008) 26(10):1146-1153.
Chang et al. "Electronic signatures of all four DNA nucleosides in a tunneling gap" Nano Lett (2010) 10:1070-1075.
Chen et al. "Atomic layer deposition to fine-tune the surface properties and diameters of fabricated nanopores" Nano Lett (2004) 4(7):1333-1337.
Chou et al. "Electrodeless dielectrophoresis of single- and double-stranted DNA" Biophys J (2002) 83:2170-2179.
Clarke et al. "Continuous base identification for single-molecule nanopore DNA sequencing" NNano (2009) 4(4):265-270.
Cockroft et al. "A single-molecule nanopore device detects DNA polymerase activity with single-nucleotide resolution" JACS (2008) 130(3):818-820.
Derrington et al. "Nanopore DNA sequencing with MspA" PNAS (2010) 107(37):16060-16065.
Geirhart et al., "Nanopore with Transverse Nanoelectrodes for Electrical Characterization and Sequencing of DNA," Sensors and Actuators B (2008) 132:593-600.
Gramlich et al. "Click-click-click: Single to triple modification of DNA" Angew Chem Int Ed (2008) 47:3442-3444.
Harrer et al. "Electrochemical characterization of thin film electrodes toward developing a DNA transistor" Langmuir (2010) 26(24):19191-19198.
He et al. "A hydrogen-bonded electron-tunneling circuit reads the base composition of unmodified DNA" Nanotech (2009) 20(7):075102.
Holden et al. "Direct introduction of single protein channels and pores into lipid bilayers" JACS (2005) 127(18):6502-6503.
Hopfner et al. "Mechanisms of nucleic acid translocases: lessons from structural biology and single-molecule biophysics" Curr Opin Struct Biol (2007) 17(1):87-95.
Howorka et al. "Sequence-specific detection of individual DNA strands using engineered nanopores" Nature Biotech (2001) 19:636-639.

(56) References Cited

OTHER PUBLICATIONS

Hughes et al. "Optical absorption of DNA—carbon nanotube structures" Nano Lett (2007) 7(5):1191-1194.
Hurt et al. "Specific nucleotide binding an rebinding to individual DNA polymerase complexes captured on a nanopore" JACS (2009) 131(10):3772-3778.
Jiang et al. "The open pore conformation of potassium channels" Nature (2002) 47:523-526.
Kang et al. "A storable encapsulated bilayer chip containing a single protein nanopore" JACS (2007) 129:4701-4705.
Kim et al. "Rapid fabrication of uniformly sized nanopores and nanopore arrays for parallel DNA analysis" Adv Mat (2006) 18:3149-3153.
Li et al. "DNA molecules and configurations in a solidstate nanopore microscope" Nature Mat (2003) 2:611-615.
Liang et al. "Nanogap detector inside nanofluidic channel for fast real-time label-free DNA analysis" Nano Lett (2008) 8(5):1472-1476.
Lieberman et al. "Processive replication of single DNA molecules in a nanopore catalyzed by phi29 DNA polymerase" JACS (2010) 132(50):17961-17972.
Lindsay et al. "Recognition tunneling" Nanotech (2010) 21:262001.
Liu et al. "Descreening of field effect in electrically gated nanopores" Appl Phys Lett (2010) 97:143109.
Liu et al. "Translocation of single-stranded DNA through single-walled carbon nanotubes" Science (2010) 327:64-67.
Lohman et al. "Non-hexameric DNA helicases and translocases: mechanisms and regulation" Nature Rev Mol Cell Biol (2008) 9:391-401.
Lu et al. "Nanowire transistor performance limits and applications" IEEE Trans on Electron Dev (2008) 55(11):2859-2876.
Luan et al. "Base-by-base ratcheting of single stranded DNA through a solid-state nanopore" Phys Rev Lett (2010) 104:8103-8106.
Meller et al. "Voltage-driven DNA translocation through a nanopore" Phys Rev Lett (2001) 86(15):3435-3438.
Merchant et al. "DNA Translocation Through Graphene Nanopores," NanoLetters (2010) 10:2915-2921.
Pease et al. "Sequence-directed DNA translocation by purified FtsK" Science (2005) 307:586-590.
Polonsky et al. "Nanopore in metal-dielectric sandwich for DNA position control" Appl Phys Lett (2007) 91:153103-153103-3.
Reimhult et al. "Membrane biosensor platforms using nano- and microporous supports" Trends in Biotech (2007) 26(2):82-89.
Schneider et al. "DNA translocation through graphene nanopores" Nano Lett (2010) 10:3163-3167.
Shchepinov et al. "Oligonucleotide dendrimers: synthesis and use as polylabelled DNA probes" Nucl Acids Res (1997) 25(22):4447-4454.
Singleton et al. "Structure and mechanism of helicases and nucleic acid translocases" Ann Rev Biochem (2007) 76:23-50.
Smeets et al. "Noise in solid-state nanopores" PNAS (2008) 105(2):417-421.
Stoddart et al. "Single-nucleotide discrimination in immobilized DNA oligonucleotides with a biological nanopore" PNAS (2009) 106:7702-7707.
Storm et al. "Fabrication of solid-state nanopores with single-nanometre precision" Nature Mat (2003) 2:537-540.
Tanaka et al. "Partial sequencing of a single DNA molecule with a scanning tunnelling microscope" Nature Nanotech (2009) 4:518-522.
Tian et al. "Three-dimensional, flexible nanoscale field-effect transistors as localized bioprobes" Science (2010) 329:830-834.
Tsutsui et al. "Identifying singl-e nucleotides by tunnelling current" Nature Nanotech (2010) 5:286-290.
Turner et al. "Confinement-induced entropic recoil of single DNA molecules in a nanofluidic structure" Phys Rev Lett (2002) 88(12):128103-1-4.
Wanunu et al. "Rapid electronic detection of probe-specific microRNAs using thin nanopore sensors" Nature Nanotech (2010) 5:807-814.
White et al. "Single ion-channel recordings using glass nanopore membranes" JACS (2007) 129(38):11766-11775.
Wu et al. "Protein nanopores with covalently attached molecular adapters" JACS (2007) 129:16142-16148.
International Search Report and Written Opinion dated Jan. 25, 2011 for related case PCT/US2010/001072.
International Preliminary Report on Patentability dated Oct. 20, 2011 for related case PCT/US2010/001072.
Kumar et al., "PEG-Labeled Nucleotides and Nanopore Detection for Single Molecule DNA Sequencing by Synthesis," Scientific Reports (2012) 2:684 DOI:10.1038-srep00684.
Complaint for Patent Infringement of U.S. Pat. No. 9,546,400, filed on Mar. 15, 2017 in the United States District Court for the District of Delaware (*Pacific Biosciences of California* vs. *Oxford Nanopore Technologies, Inc.*).
Oxford's Motion and Opening Brief in Support of its Motion to Dismiss Pacific Biosciences' Complaint dated May 8, 2017, on the Ground That the Asserted Claims are Invalid; with Exhibits included.
Oxford Nanopore Opening Brief in Support of Motion to Dismiss, dated May 8, 2017, U.S. District Court Civil Case No. 17-275.
Pacific Biosciences Opposition to Oxford Nanopore Motion to Dismiss, dated Jun. 5, 2017, U.S. District Court Civil Case No. 17-275.
Oxford Nanopore Reply Brief, dated Jun. 26, 2017, U.S. District Court Civil Case No. 17-275.
Court Order Denying Oxford Nanopore Motion to Dismiss, dated Nov. 9, 2017, U.S. District Court Civil Case No. 17-275.
Pacific Biosciences Complaint of Patent Infringement against Oxford Nanopore, dated Sep. 25, 2017, U.S. District Court Civil Case No. 17-1353.
Oxford Nanopore Motion to Dismiss Pacific Bioscience Complaint of Patent Infringement, dated Dec. 14, 2017, U.S. District Court Civil Case No. 17-1353.
Oxford Nanopore Opening Brief in Support of Motion to Dismiss, dated Dec. 14, 2017, U.S. District Court Civil Case No. 17-1353.
Pacific Biosciences Response to Oxford Nanopore Motion to Dismiss, dated Jan. 5, 2018, U.S. District Court Civil Case No. 17-1353.
Oxford Nanopore Reply Brief, dated Jan. 17, 2018, U.S. District Court Civil Case No. 17-1353.
Court Order Denying Oxford Nanopore Motion to Dismiss, dated Mar. 22, 2018, U.S. District Court Civil Case No. 17-1353.
Court Memorandum Opinion Regarding Motion to Dismiss, dated Mar. 22, 2018, U.S. District Court Civil Case No. 17-1353.
Pacific Biosciences 2nd Amended Complaint, dated Mar. 28, 2018, U.S. Disctrict Court Civil Case Nos. 17-1353 & 17-275.
Oxford Nanopore Invalidity Contentions, dated Jul. 13, 2018, U.S. Disctrict Court Civil Case Nos. 17-1353 & 17-275.
Joint Claim Constructions, dated Aug. 10, 2018, U.S. Disctrict Court Civil Case Nos. 17-1353 & 17-275.
Pacific Biosciences Reply Brief, dated Aug. 10, 2018, U.S. Disctrict Court Civil Case Nos. 17-1353 & 17-275.
Pacific Biosciences 3rd Amended Complaint, dated Aug. 23, 2018, U.S. Disctrict Court Civil Case Nos. 17-1353 & 17-275.
Oxford Nanopore Claim Constructions Opening Brief, dated Sep. 7, 2018, U.S. Disctrict Court Civil Case Nos. 17-1353 & 17-275.
Pacific Biosciences Claim Constructions Opening Brief, dated Sep. 7, 2018, U.S. Disctrict Court Civil Case Nos. 17-1353 & 17-275.
Inter Party Review Initiated by Oxford Nanopore Against Pacific Biosciences U.S. Pat. No. 9,546,400 Before the U.S. Patent Appeal Board, dated Mar. 15, 2018, IPR No. 2018-00789.
Pacific Biosciences Preliminary Response in Inter Party Review of U.S. Pat. No. 9,546,400 Before the U.S. Patent Appeal Board, dated Jul. 5, 2018, IPR No. 2018-00789.
Decision Denying Institution of Inter Party Review Initiated by Oxford Nanopore Against Pacific Biosciences U.S. Pat. No. 9,546,400 Before the U.S. Patent Appeal Board, dated Sep. 25, 2018, IPR No. 2018-00789.
Inter Party Review Initiated by Oxford Nanopore Against Pacific Biosciences U.S. Pat. No. 9,678,056 Before the U.S. Patent Appeal Board, dated Sep. 25, 2018, IPR No. not yet assigned (Later Assigned IPR No. 2018-01795).

(56) References Cited

OTHER PUBLICATIONS

Memorandum Opinion of the District Court Initial Markman Decision, dated Mar. 6, 2019, U.S. District Court Civil Case Nos. 17-1353 & 17-275.
Pacific Biosciences Motion for Reconsideration, dated Mar. 20, 2019, U.S. District Court Civil Case Nos. 17-1353 & 17-275.
Memorandum Order Reversing Construction of Kinetic Step, dated Jun. 12, 2019, U.S. District Court Civil Case Nos. 17-1353 & 17-275.
Pacific Biosciences Preliminary Response to Oxford Nanopore's Petition for Inter Partes Review of U.S. Pat. No. 9,678,056 Before the U.S. Patent Appeal Board, dated Feb. 13, 2019, IPR No. 2018-01795.
Termination Dismissing the Proceeding, dated Mar. 26, 2019, IPR No. 2018-01795.
Oxford Nanopore Brief in Support of Motion to Dismiss and Counterclaim, dated Jul. 11, 2018, U.S. Disctrict Court Civil Case Nos. 17-1353 & 17-275.
Pacific Biosciences Reply in Support of Motion to Dismiss and Partially Dismiss Oxford Nanopore Counterclaim, dated Jul. 27, 2018, U.S. Disctrict Court Civil Case Nos. 17-1353 & 17-275.
Oxford Nanopore Answer to 3rd Amendmend Complaint and Counterclaims, dated Sep. 12, 2018, U.S. Disctrict Court Civil Case Nos. 17-1353 & 17-275.
Oxford Nanopore Responsive Claim Construction Brief, dated Nov. 20, 2018, U.S. Disctrict Court Civil Case Nos. 17-1353 & 17-275.
Pacific Biosciences Answer to Claim Construction Brief, dated Nov. 20, 2018, U.S. Disctrict Court Civil Case Nos. 17-1353 & 17-275.
Memorandum in Support of Order Granting Pacific Biosciences Motion to Dismiss Counterclaims, dated Feb. 19, 2019, U. S. Disctrict Court Civil Case Nos. 17-1353 & 17-275.
Expert Report of Mark Akeson, dated Jul. 29, 2019, U.S. Disctrict Court Civil Case Nos. 17-1353 & 17-275.
Expert Report of Nick Goldman, dated Jul. 29, 2019, U.S. Disctrict Court Civil Case Nos. 17-1353 & 17-275.
Expert Report of Patrick Hrdlicka, dated Jul. 29, 2019, U.S. Disctrict Court Civil Case Nos. 17-1353 & 17-275.
Expert Report of Sylvia Hall, dated Jul. 29, 2019, U.S. Disctrict Court Civil Case Nos. 17-1353 & 17-275.
Expert Report of Taekjip Ha, dated Jul. 29, 2019, U.S. Disctrict Court Civil Case Nos. 17-1353 & 17-275.

* cited by examiner

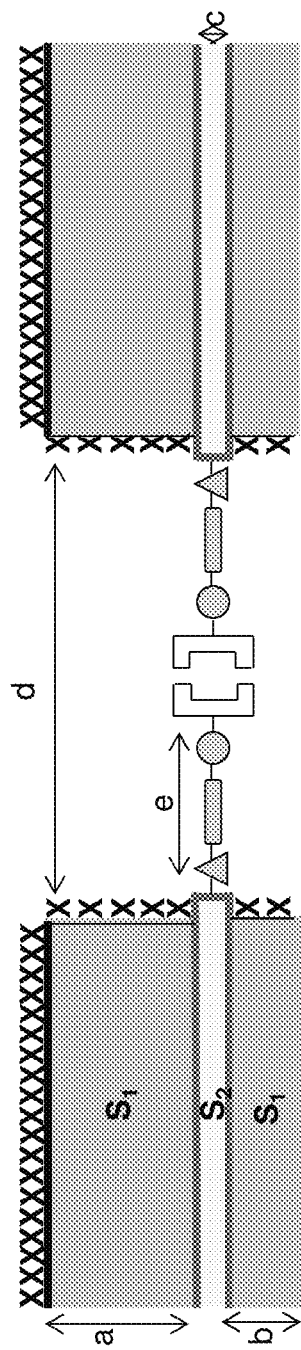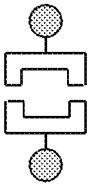
X = Substrate 1 (S₁) surface treatment
△ = Substrate 2 (S₂) surface treatment
▬ = Linker/spacer
= Protein (or other biological machinery) modified with conjugation sites
Figure 5

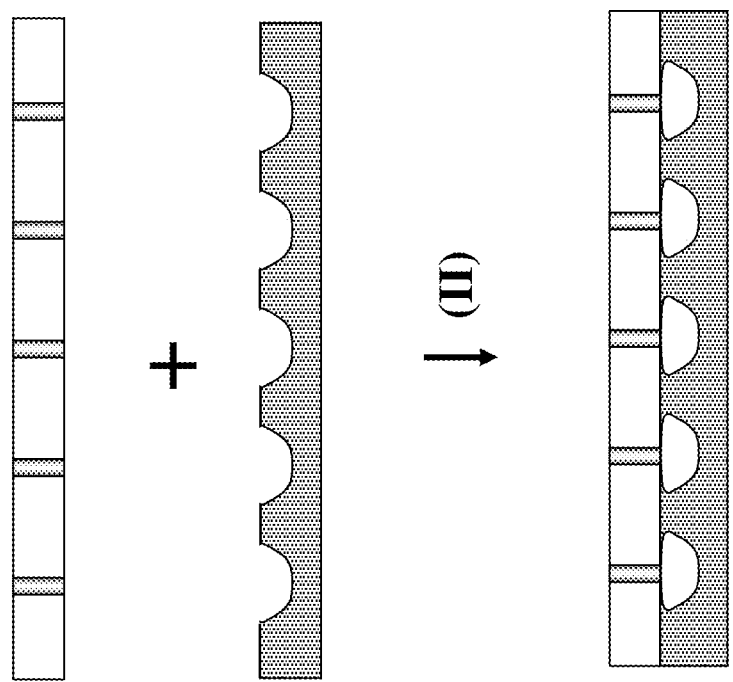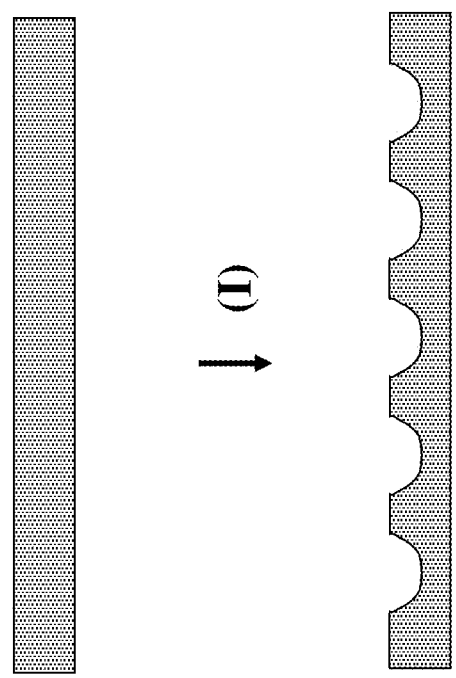
Figure 7

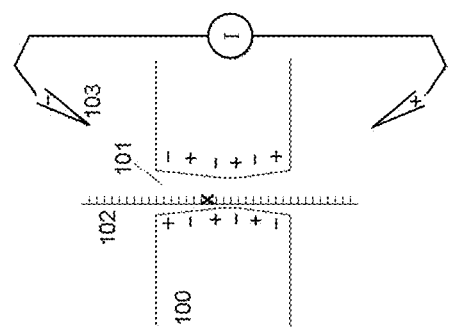
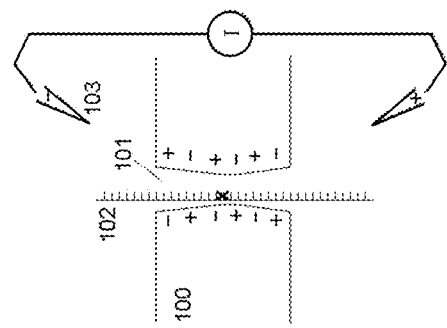
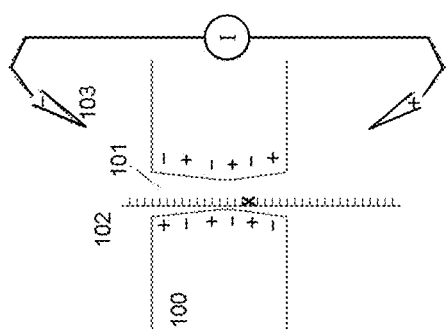
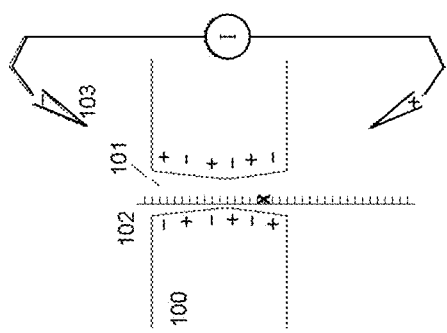
Figure 18 cis trans

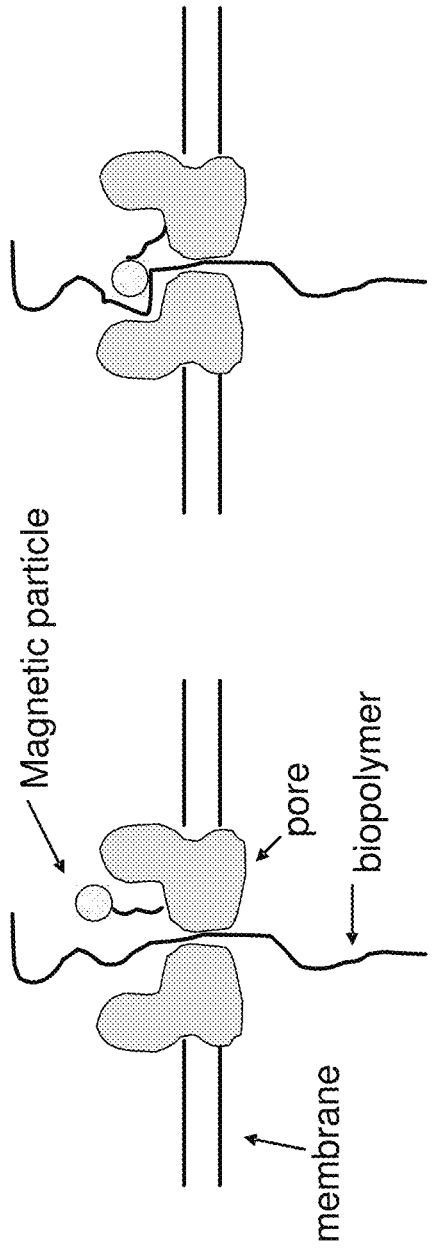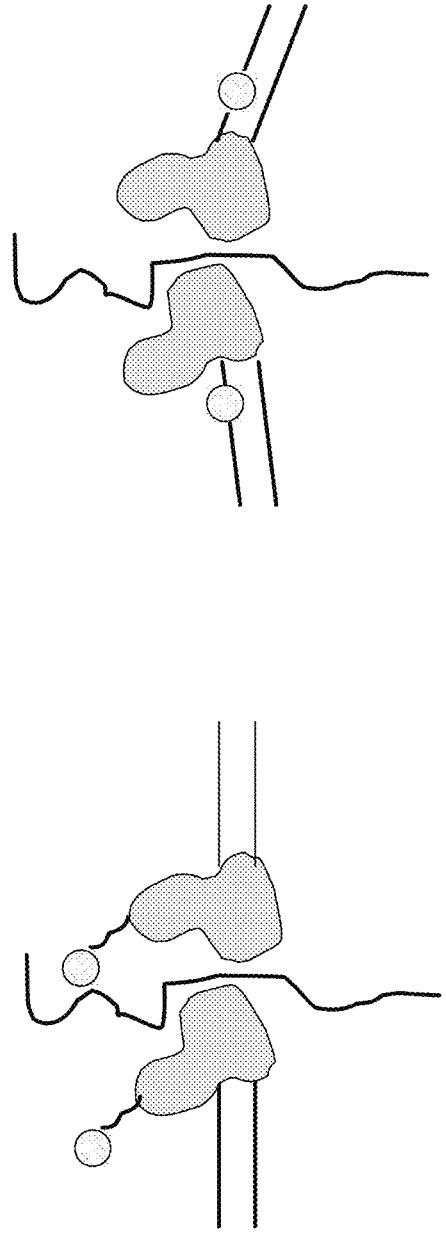
Figure 31A
Figure 31B
Figure 31C
Figure 31D

METHOD OF SEQUENCING MULTIPLE COPIES OF A SEQUENCE IN A CIRCULAR TEMPLATE

CROSS-REFERENCE TO RELATED APPLICATIONS

This application is a continuation application of U.S. patent application Ser. No. 15/654,395, filed Jul. 19, 2017, which is a continuation application of U.S. patent application Ser. No. 15/439,497, filed Feb. 22, 2017, now U.S. Pat. No. 9,772,323, which is a continuation application of U.S. patent application Ser. No. 15/337,312, filed Oct. 28, 2016, which is a continuation application of U.S. patent application Ser. No. 14/026,906, filed Sep. 13, 2013, now U.S. Pat. No. 9,546,400, which is a continuation application of U.S. patent application Ser. No. 12/757,789, filed Apr. 9, 2010, now U.S. Pat. No. 8,986,928, which claims priority to and benefit of: U. S. Provisional Patent Application 61/168,431, filed Apr. 10, 2009, the full disclosures of which is incorporated herein by reference in its entirety.

STATEMENT REGARDING FEDERALLY SPONSORED RESEARCH

Not Applicable.

BACKGROUND OF THE INVENTION

The rapid determination of the nucleotide sequence of single- and double-stranded DNA and RNA is a major goal of researchers seeking to obtain the sequence for the entire genome of an organism. The ability to determine the sequence of nucleic acids in DNA or RNA has additional importance in identifying genetic mutations and polymorphisms. The concept of using nanometer-sized holes, or "nanopores," to characterize biological macromolecules and polymer molecules has recently been developed.

Nanopore-based analysis methods often involve passing a polymeric molecule, for example single-stranded DNA ("ssDNA"), through a nanoscopic opening while monitoring a signal such as an electrical signal. Typically, the nanopore is designed to have a size that allows the polymer to pass only in a sequential, single file order. As the polymer molecule passes through the nanopore, differences in the chemical and physical properties of the monomeric units that make up the polymer, for example, the nucleotides that compose the ssDNA, are translated into characteristic electrical signals.

The signal can, for example, be detected as a modulation of the ionic current by the passage of a DNA molecule through the nanopore, which current is created by an applied voltage across the nanopore-bearing membrane or film. Because of structural differences between different nucleotides, different types of nucleotides interrupt the current in different ways, with each different type of nucleotide within the ssDNA producing a type-specific modulation in the current as it passes through a nanopore, and thus allowing the sequence of the DNA to be determined.

Nanopores that have been used for sequencing DNA include protein nanopores held within lipid bilayer membranes, such as α-hemolysin nanopores, and solid state nanopores formed, for example, by ion beam sculpting of a solid state thin film. Devices using nanopores to sequence DNA and RNA molecules have generally not been capable of reading sequence at a single-nucleotide resolution.

While this prior work has shown the promise of nanopores for detecting some sequence information, there is a need for accurate, reliable devices and methods for measuring sequences such as those of RNA and DNA. Accordingly, there is a need for a method of fabricating arrays of nanopores in a form that is amenable to manufacturing. Similarly, there is also a related need for devices capable of sequencing molecules having nanoscale dimensions at a high speed and at a high level of resolution.

SUMMARY OF THE INVENTION

In some aspects, the invention provides a device for determining polymer sequence information comprising: a substrate comprising an array of nanopores; each nanopore fluidically connected to an upper fluidic region and a lower fluidic region; wherein each upper fluidic region is fluidically connected through an upper resistive opening to an upper liquid volume. In some embodiments the upper liquid volume is fluidically connected to two or more upper fluidic regions. In some embodiments each lower fluidic region is fluidically connected through a lower resistive opening to a lower liquid volume, and wherein the lower liquid volume is fluidically connected to two or more lower fluidic regions.

In some embodiments the substrate is a semiconductor comprising circuit elements. In some embodiments either the upper fluidic region or the lower fluidic region for each nanopore or both the lower fluidic region and the upper fluidic region for each nanopore is electrically connected to a circuit element. In some embodiments the circuit element comprises an amplifier, an analog-to-digital converter, or a clock circuit.

In some embodiments the resistive opening comprises one or more channels. In some embodiments the length and width of the one or more channels are selected to provide a suitable resistance drop across the resistive opening. In some embodiments the conduit is a channel through a polymeric layer. In some embodiments the polymeric layer is polydimethylsiloxane (PDMS).

In some embodiments the device further comprises an upper drive electrode in the upper liquid volume, a lower drive electrode in the lower liquid volume, and a measurement electrode in either the upper liquid volume or the lower liquid volume.

In some embodiments the device further comprises an upper drive electrode in the upper liquid volume, a lower drive electrode in the lower liquid volume, and an upper measurement electrode in the upper liquid volume and a lower measurement electrode in the lower liquid volume.

In some embodiments the nanopore, upper fluidic reservoir and lower fluidic reservoir are disposed within a channel that extends through the substrate. In some embodiments the upper fluidic reservoir and lower fluidic reservoir each open to the same side of the substrate.

In some aspects, the invention provides a polymer sequencing device comprising: a) a nanopore layer comprising an array of nanopores, each nanopore having a cross sectional dimension of 1 to 10 nanometers, and having a top and a bottom opening, wherein the bottom opening of each nanopore opens into a discrete reservoir, resulting in an array of reservoirs, wherein each reservoir comprises one or more electrodes, the nanopore layer physically and electrically connected to a semiconductor chip, and b) the semiconductor chip, comprising an array of circuit elements, wherein each of the electrodes in the array of reservoirs is connected to at least one circuit element on the semiconductor chip.

In some embodiments the array of nanopores comprises an array of holes in a solid substrate, each hole comprising a protein nanopore. In some embodiments each protein nanopore is held in place in its hole with a lipid bilayer. In some embodiments the top opening of the nanopores open into an upper reservoir. In some embodiments the circuit elements comprise amplifiers, analog to digital converters, or clock circuits.

In some aspects, the invention provides a method of fabricating a polymer sequencing device comprising: a) obtaining a semiconductor substrate; b) processing the semiconductor substrate to create an array of microfluidic features, wherein the microfluidic features are capable of supporting an array of nanopores; c) subsequently producing circuit elements on the substrate that are electronically coupled to the microfluidic features; and d) introducing nanopores into the microfluidic features.

In some embodiments the circuit elements are CMOS circuit elements. In some embodiments the CMOS circuit elements comprise amplifiers, analog to digital converters.

In some aspects, the invention provides a method of fabricating a polymer sequencing device comprising the following steps in the order presented: a) obtaining a semiconductor substrate; b) processing the semiconductor substrate to create an array of CMOS circuits, without carrying out an aluminum deposition step; c) processing the semiconductor substrate having the CMOS circuits to produce microfluidic features, wherein the microfluidic features are capable of supporting nanopores; d) subsequently performing an aluminum deposition step to create conductive features; and e) introducing nanopores into the microfluidic features.

In some embodiments the processing of step (c) to create the microfluidic features subjects the semiconductor substrate to temperatures greater than about 250° C.

In some aspects, the invention provides a method for fabricating a polymer sequencing device comprising: a) producing an insulator layer having microfluidic elements comprising an array of pores extending through the insulator; b) bonding the insulator layer with a semiconductor layer; c) exposing the semiconducting layer to etchant through the pores in the insulator layer to produce discrete reservoirs in the semiconductor layer; d) removing portions of the semiconductor layer to isolate the discrete reservoirs from one another, e) incorporating electrical contacts into the semiconductor layer that allow current to be directed to each of the discrete reservoirs; and f) bonding an electric circuit layer to the semiconducting layer such that the electric circuits on the electric circuit layer are electrically connected to the electrical contacts on the semiconductor layer.

In some embodiments the method further comprises the step of adding nanopores into each of the pores.

In some embodiments the method further comprises two or more electrodes within each of the discrete reservoirs.

In some aspects, the invention provides a method for fabricating a polymer sequencing device comprising: a) producing an insulator layer having microfluidic elements comprising an array of pores extending through the insulator; b) bonding the insulator layer with a semiconductor layer wherein the semiconducting layer comprises an array of wells corresponding to the pores on the insulator layer, whereby the bonding produces an array of discrete reservoirs, each discrete reservoir connected to a pore; c) removing portions of the semiconductor layer to isolate the discrete reservoirs from one another d) adding electrical contacts to the semiconductor layer that allow current to be directed to each of the discrete reservoirs; and e) bonding an electric circuit layer to the semiconducting layer such that the electric circuits on the electric circuit layer are electrically connected to the electrical contacts on the semiconductor layer.

In some aspects, the invention provides a method for fabricating a polymer sequencing device comprising: a) obtaining an SOI substrate comprising a top silicon layer, an insulator layer, and a bottom silicon layer; b) processing the top silicon layer and bottom silicon layer to remove portions of each layer to produce an array of exposed regions of the insulator layer in which both the top and bottom surfaces of the insulator layer are exposed; c) processing the top silicon layer or the bottom silicon layer or both the top silicon layer and bottom silicon layer to add electrodes and electrical circuits; and d) processing the insulator layer to produce an array of pores through the exposed regions of the insulator layer.

In some embodiments the method further comprises adding polymer layers to the top of the device, the bottom of the device, or to the top and to the bottom of the device to produce microfluidic features.

In some embodiments the method further comprises inserting a nanopore into the pores in the insulator layer.

In some aspects, the invention provides a method for determining sequence information about a polymer molecule comprising: a) providing a device comprising a substrate having an array of nanopores; each nanopore fluidically connected to an upper fluidic region and a lower fluidic region; wherein each upper fluidic region is fluidically connected through a an upper resistive opening to an upper liquid volume; and each lower fluidic region is connected to a lower liquid volume, and wherein the upper liquid volume and the lower liquid volume are each fluidically connected to two or more fluidic regions, wherein the device comprises an upper drive electrode in the upper liquid volume, a lower drive electrode in the lower liquid volume, and a measurement electrode in either the upper liquid volume or the lower liquid volume; b) placing a polymer molecule to be sequenced into one or more upper fluidic regions; c) applying a voltage across the upper and lower drive electrodes so as to pass a current through the nanopore such that the polymer molecule is translated through the nanopore; d) measuring the current through the nanopore over time; and e) using the measured current over time in step (d) to determine sequence information about the polymer molecule.

In some embodiments the substrate comprises electronic circuits electrically coupled to the measurement electrodes which at least partially process signals from the measurement electrodes.

In some embodiments the upper drive electrode and lower drive electrode are each biased to a voltage above or below ground, and at least a portion of the substrate electrically connected to the electronic circuits is held at ground potential.

In some aspects, the invention provides a method for determining sequence information about a polymer molecule comprising: a) providing a device having an array of nanopores, each connected to upper and lower fluid regions; wherein the device comprises electronic circuits electrically connected to electrodes in either the upper fluid regions or lower fluid regions or both the upper and lower fluid regions; b) placing a polymer molecule in an upper fluid region; c) applying a voltage across the nanopore whereby the polymer molecule is translocated through the nanopore; d) using the electronic circuits to monitor the current through the nanopore over time, wherein the electronic circuits process the incoming current over time to record events, thereby generating event data; and e) using the event data from step (d) to obtain sequence information about the polymer molecule.

In some embodiments the events comprise a change in current level above or below a specified threshold. In some embodiments the electronic circuit records the events, the average current before the events and the average current after the events. In some embodiments the event data is generated without reference to time.

In some embodiments a clock circuit is used such that the relative time that the events occurred is also determined. In some embodiments the event data generated by the electronic circuits on the device is transmitted from the device for further processing. In some embodiments the information is transmitted optically.

In some aspects, the invention provides a method for determining the sequence of a polymer having two or more types of monomeric units in a solution comprising: a) actively translocating the polymer through a pore; b) measuring a property which has a value that varies depending on whether and which of the two or more a types of monomeric unit is in the pore, wherein the measuring is performed as a function of time while the polymer is actively translocating; and c) determining the sequence of the two or more types of monomeric units in the polymer using the measured property from step (b) by performing a process including the steps of: (i) deconvolution, (ii) peak finding, and (iii) peak classification.

In some embodiments the polymer is a nucleic acid, the monomeric units are nucleotide bases or nucleotide analogs, and the measured property is current. In some embodiments the deconvolution comprises (a) carrying out measurements of current as a function of time on nucleic acids having known sequences to produce calibration information, and (b) using the calibration information perform the deconvolution. In some embodiments the deconvolution uses a Weiner, Jansson, or Richardson-Levy deconvolution. In some embodiments the peak classification is performed by a heuristic tree algorithm, Bayesian network, hidden Markov model, or conditional random field. In some embodiments the method further comprises step (iv) of quality estimation.

In some embodiments the measurements on nucleic acids having known sequences comprising known n-mers. In some embodiments the known n-mers are 3-mers, 4-mers, 5-mers or 6-mers.

DESCRIPTION OF THE FIGURES

FIG. 5 shows an embodiment of the invention illustrating the chemistry used to produce an array of hybrid nanopores of the invention.

FIG. 7 shows the production of microfluidic features in a semiconductor substrate prior to wafer bonding.

FIG. 18 illustrates transporting a polymer through a nanopore using alternating fields.

FIGS. 31A-31D show the use of tethered magnetic particles to control DNA translocation through the pore.

DETAILED DESCRIPTION OF THE INVENTION

I. General

Figure 1A:
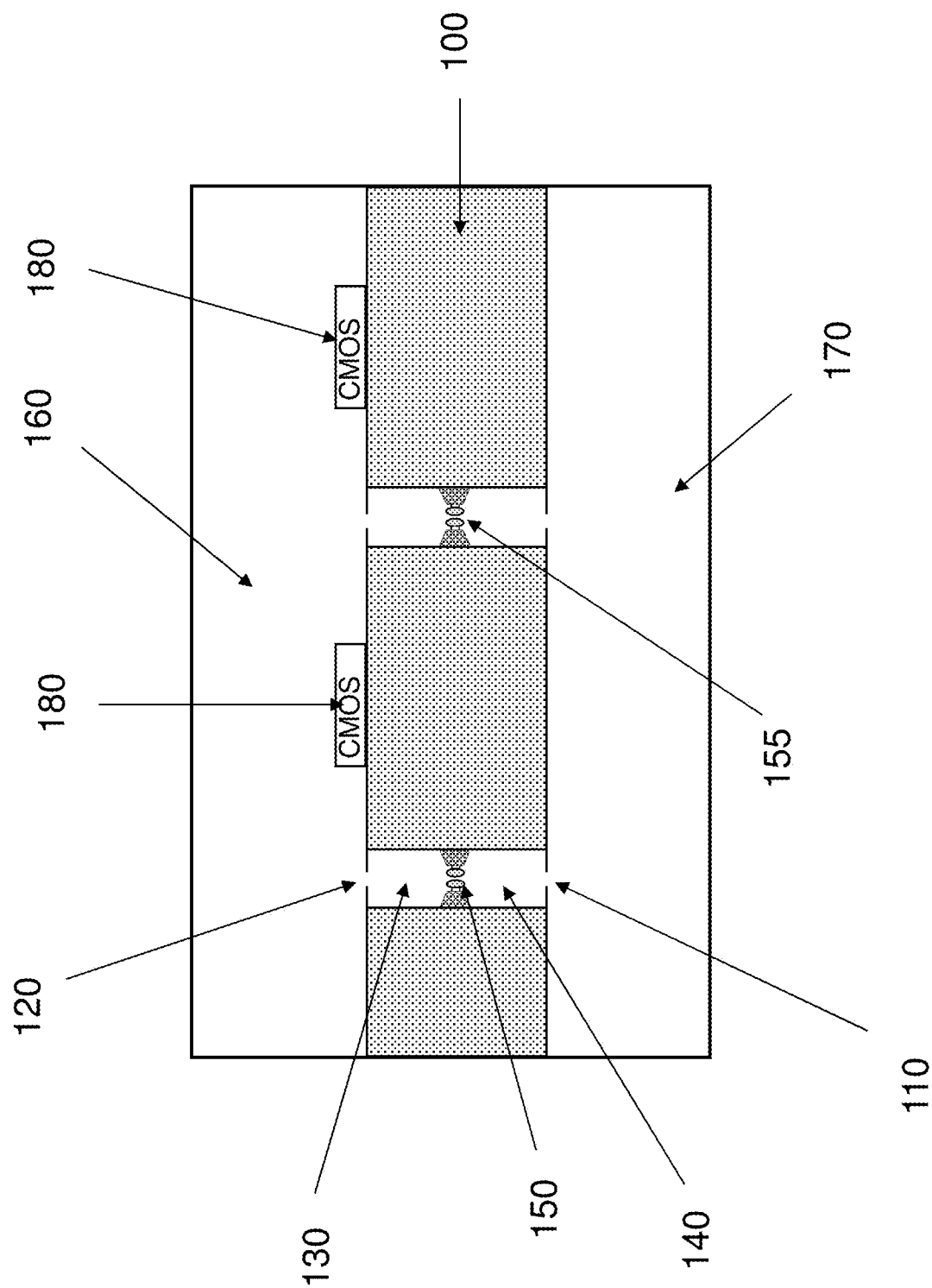
FIG. 1A shows an embodiment of an array or nanopores of the invention having resistive openings and incorporated electronics associated with the nanopores.

The invention relates to devices, systems, and methods for sequencing polymers using nanopores. In particular, the invention relates to multiplex sequencing in which sequencing data is simultaneously obtained from multiple nanopores. In some aspects, the invention relates to multiplex nanopore sequencing devices that directly incorporate semiconductor devices, such as CMOS devices. The devices of the invention can be made wherein the nanopores are formed in a semiconductor substrate, such as silicon. Alternatively, the devides can be made in a composite semiconductor substrate such as silicon-insulator-silicon (SOI), or can be made by bonding together semiconductor and insulator components.

The incorporation of semiconductors such as silicon into the devices provides for the inclusion of electronic circuitry in close association with the nanopores. For example, the use of silicon allows for a multiplex device having an array of electronic circuits wherein each nanopore in the array is directly associated with a set of electronic circuits. These circuits can provide the functions of measurement, data manipulation, data storage, and data transfer. The circuits can provide amplification, analog to digital conversion, signal processing, memory, and data output.

In some aspects, the invention relates to devices and methods which allow for multiplex electronic sequencing measurements in a manner that reduces or eliminates crosstalk between the nanopores in the nanopore array. In some cases it is desirable for a nanopore sequencing measurement system to have a pair of drive electrodes that drive current through the nanopores, and one or more measurement electrodes that measure the current through the nanopore. It can be desirable to have the drive electrodes drive current through multiple nanopores in the nanopore array, and have measurement electrodes that are directly associated with each nanopore. We have found that this type of system can be obtained by the incorporation of resistive openings, which connect a reservoir of fluid in contact with the nanopore to a volume of fluid in contact with a drive electrode in a manner that creates a resistive drop across the resistive opening, but allows for fluidic connection and for ion transport between the reservoir of fluid in contact with the nanopore and the volume of fluid in contact with the drive electrode.

The resistive opening can be made from any suitable structure that provides for a resistive drop across two fluid regions while allowing for the passage of fluid including ions between the fluid regions. In general, the resistive opening will impede, but not prevent the flow of ions. The resistive opening can comprise, for example, one or more narrow holes, apertures, or conduits. The resistive opening can comprise a porous or fibrous structure such as a nanoporous or nanofiber material. The resistive opening can comprise a single, or multiple, long, narrow channels. Such channels can be formed, for example, in a polymeric material such as polydimethylsiloxane (PDMS).

The nanopore sequencing of the invention relates to the sequencing of polymers. The polymers to be sequenced can be, for example, nucleic acids such as RNA or DNA, proteins, polypeptides, polysaccharides, or other polymers for which information about the sequence is of value. In some embodiments, the sequencing is performed by measuring the modulation of current as the polymer molecule, e.g. a single-stranded DNA molecule passes through the nanopore. In some cases, the polymer as a whole does not pass through the pore, but portions of the polymer, or molecules associated with portions of the polymer pass through the nanopore, and are detected. For example, in some cases, a nucleic acid is sequentially degraded, sequentially releasing monomeric units, e.g. by an exonuclease, and the monomeric units are detected as they pass through the nanopore. Certain aspects and embodiments are described as being implemented with specific materials, e.g. a specific polymer. It understood that the embodiments described can be implemented using any suitable material such as those described elsewhere herein or as known in the art.

II. Nanopore Sequencing Devices

The invention relates in some aspects to devices for multiplex nanopore sequencing. In some cases, the devices of the invention comprise resistive openings between fluid regions in contact with the nanopore and fluid regions which house a drive electrode. The devices of the invention can be made using a semiconductor substrate such as silicon to allow for incorporated electronic circuitry to be located near each of the nanopores or nanometer scale apertures in the array of nanopores which comprise the multiplex sequencing device. The devices of the invention will therefore comprise arrays of both microfluidic and electronic elements. In some cases, the semiconductor which has the electronic elements also includes microfluidic elements that contain the nanopores. In some cases, the semiconductor having the electronic elements is bonded to another layer which has incorporated microfluidic elements that contain the nanopores.

The devices of the invention generally comprise a microfluidic element into which a nanopore is disposed. This microfluidic element will generally provide for fluid regions on either side of the nanopore through which the molecules to be detected for sequence determination will pass. In some cases, the fluid regions on either side of the nanopore are referred to as the cis and trans regions, where the molecule to be measured generally travels from the cis region to the trans region through the nanopore. For the purposes of description, we sometimes use the terms upper and lower to describe such reservoirs and other fluid regions. It is to be understood that the terms upper and lower are used as relative rather than absolute terms, and in some cases, the upper and lower regions may be in the same plane of the device. The upper and lower fluidic regions are electrically connected either by direct contact, or by fluidic (ionic) contact with drive and measurement electrodes. In some cases, the upper and lower fluid regions extend through a substrate, in other cases, the upper and lower fluid regions are disposed within a layer, for example, where both the upper and lower fluidic regions open to the same surface of a substrate. Methods for semiconductor and microfluidic fabrication described herein and as known in the art can be employed to fabricate the devices of the invention.

FIG. 1A shows a cross section of an exemplary multiplex nanopore sequencing device of the invention comprising resistive openings. Substrate layer 100 comprises a semiconductor material such as silicon. The semiconductor substrate comprises an array of holes or pores comprising nanopores. FIG. 1A shows two pores. Devices of the invention can have any suitable number of pores to facilitate multiplex sequencing, for example 2 to 10 pores, 10 to 100 pores, 100 to 1000 pores, 1000 to 10,000 pores or more than 10,000 pores. Each of the pores has a nanopore or nanometer scale aperture 150. As used herein the term nanopore, nanometer scale aperture, and nanoscale aperture are used interchangeably. In each case, the term refers to an opening which is of a size such that when molecules of interest pass through the opening, the passage of the molecules can be detected by a change in signal, for example, electrical signal, e.g. current. In some cases the nanopore comprises a protein, such as alpha-hemolysin or MspA, which can be modified or unmodified. In some cases, the nanopore is disposed within a membrane, or lipid bilayer, which can be attached to the surface of the microfluidic region of the device of the invention by using surface treatments as described herein and as known in the art. In some cases, the nanopore can be a solid state nanopore. Solid state nanopores can be produced as described in U.S. Pat. Nos. 7,258,838, 7,504,058. In some cases, the nanopore comprises a hybrid protein/solid state nanopore in which a nanopore protein is incorporated into a solid state nanopore.

The device of FIG. 1A has upper fluidic region 130 and lower fluidic region 140, which are in contact with the nanopore 150. Upper fluidic region 130 is fluidically connected to upper fluid volume 160 through the upper resistive opening 120. In addition, in this device, lower fluidic region 130 is fluidically connected to lower fluid volume 170 through the lower resistive opening 110. Generally, the drive electrodes will be disposed in fluid volumes 160 and 170. The fluid volumes 160 and 170 can be in fluidic contact with multiple pores in the substrate 100 containing nanopores. The resistive opening minimizes the electrical crosstalk between the multiplex pores in the device. The semiconductor substrate 100 also comprises electrical circuits 180 and 185. Such circuits can be used to measure, process, and store electronic data and signals related to the sequencing measurements. For example, the circuits can be connected to measurement electrodes extending into the upper fluid region 130 and/or lower fluid region 140 to measure signals associated with nanopore 150. In some cases, each nanopore will have a set of embedded circuitry associated with it, for example as shown where circuitry 185 is used to measure and process electrical characteristics related to nanopore 155. The electronic circuits can be made by any suitable semiconductor processing technique described herein or known in the art. In some cases the circuits comprise CMOS circuits. The nanopores can be any suitable nanopore including a solid state nanopore, a protein nanopore, or a hybrid protein/solid state nanopore. The nanopores illustrated in FIG. 1A comprise hybrid nanopores, described in more detail below, in which a solid state nanopore is sized to accommodate a single nanopore protein, and the surface of the aperture is modified in order to hold the nanopore protein in place.

Figure 1B:
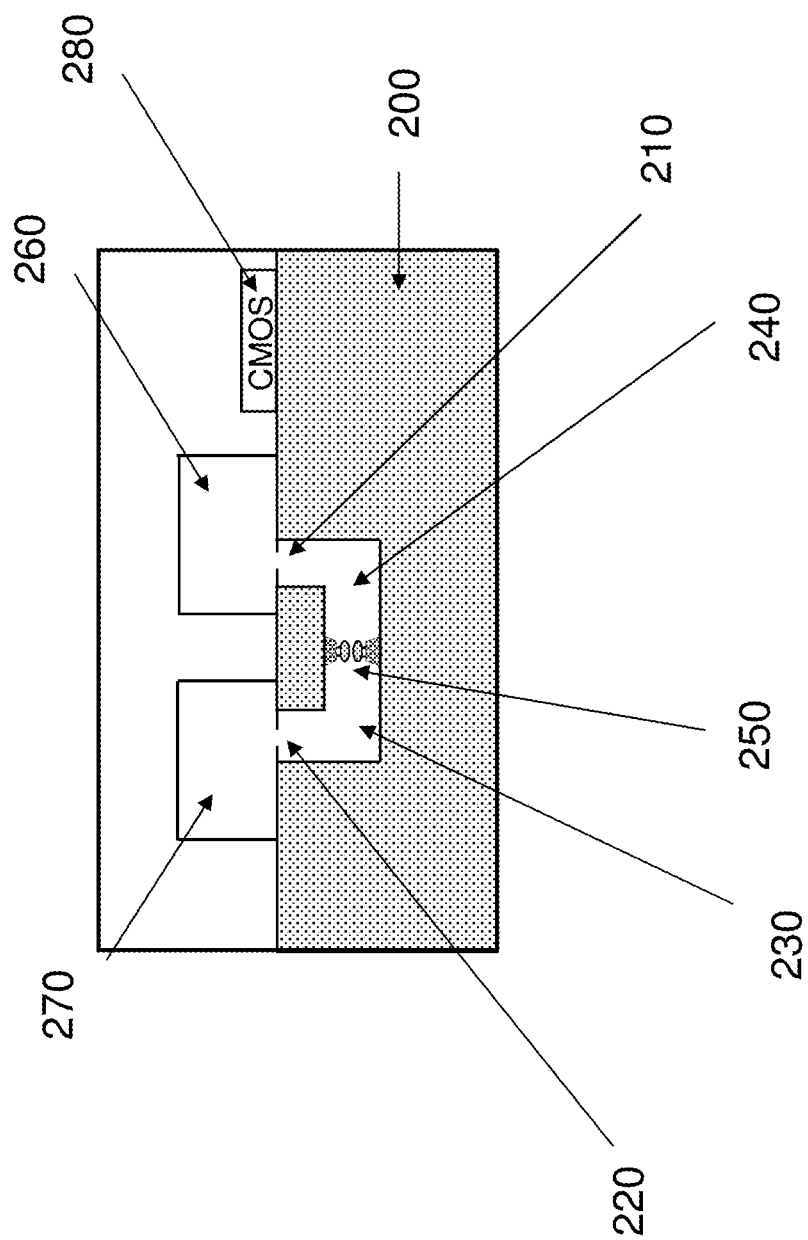
FIG. 1B shows an alternative embodiment wherein the input and output pores from the nanopore extend to the same surface.

FIG. 1B shows a cross sectional view of an alternative embodiment of a nanopore in an array of nanopores in which the upper fluidic region 230 and the lower fluidic region 240 each open to the top surface of silicon substrate 200 through resistive openings 220 and 210 to contact upper fluid volume 270 and lower fluid volume 260. As described above, the fluid volumes 260 and 270 can house the drive electrodes. The fluid volumes 260 and 270 can extend across multiple nanopores in the substrate. The semiconductor substrate 200 comprises electronic circuits 280 which can be electronically connected to measurement electrodes as described above. FIG. 1B shows one nanopore and surrounding microfluidic and electronic structures. The device of the invention will generally comprise an array of hundreds to thousands or more of such structures.

In some cases herein the term "each" is used when referring to the microfluidic or electronic elements in an array on the device. In general, the term each, does not mean all. For example, an array in which each microfluidic element comprises a nanopore may include an array in which a subset of all of the microfluidic elements comprise a nanopore. The meaning of the term "each" as used herein should be understood in light of the context in which the term is used.

In some embodiments the devices comprise an nanopore layer is separate from the semiconductor layer comprising the circuitry. In such cases, the substrate comprising the nanopore layer is typically electrically insulating. The substrate can be made from any suitable material including, for example, polymers, oxides, such as silicon oxide, a nitride, or can be made from a semiconductor material such as silicon.

One aspect of the invention is the incorporation of resistive openings into these structures for facilitating the use of a single drive electrode for multiple nanopores (a constriction architecture).

The incorporation of resistive openings associated with each nanopore can be useful for multiplexing and miniaturizing a system for nanopore DNA sequencing, providing for the use of a single drive electrode to provide the applied potential for each of the in-parallel nanopores. The use of a single set of drive electrodes can be advantageous because it simplifies the electronics and enables one to place the drive electrode away from the individual pores so that bubble-formation due to electrolysis at the electrode will not disrupt the nanopore or supporting lipid bilayer, and such that chemical species generated at the drive electrodes, for example acids, bases, oxidizing, and reducing species do not interfere with the sequencing measurements. With one set of drive electrodes, each nanopore generally requires one or more measurement electrodes. However, with one set of drive electrodes, there can be cross-talk between adjacent nanopores. For example, at any given moment, some pores will be open and others will be closed. This can result in statistical fluctuation of the resistance across the total circuit over time, which can lead to errors in determining polymer sequence.

Figure 2:
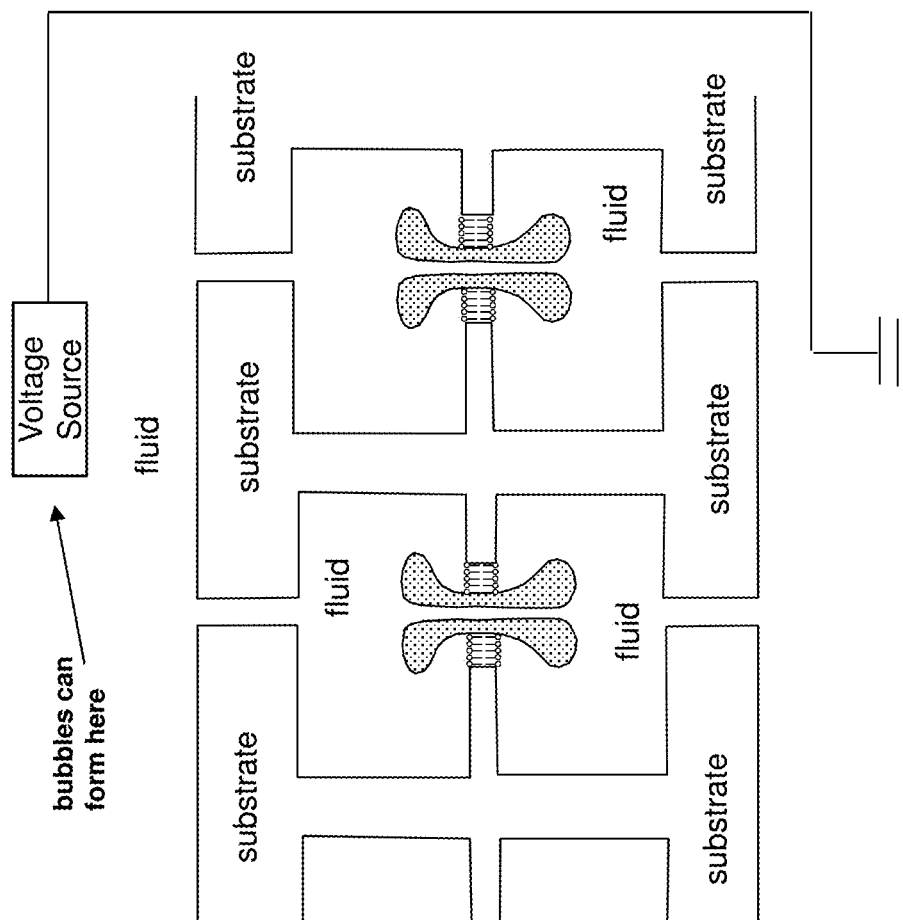
FIG. 2 shows a structure of the invention comprising resistive openings.

In some aspects of this invention, a single drive voltage source can used for all the nanopores, and each nanopore is protected by a constriction (resistive opening). FIG. 2 shows an arrangement in which constrictions in the substrate act to electrically isolate it from the fluctuations described above. In some cases, there is a constriction, or resistive opening only above or only below the nanopore. In some cases there is a constriction, or resistive opening both above and below the nanopore. The resistive openings create a resistance drop between the fluid regions that they span. The resistance drop across a resistive opening is generally on the same order as the resistance drop across the nanopore and is generally equal to or lower than the resistive drop across the nanopore. In some cases the resistance drop across the resistive opening is about 1 K-ohm to about 100 G-ohm, from about 1 M-ohm to about 10 G-ohm. In some cases, the resistance drop is about the same as the resistance drop across an unblocked pore. In some cases, the resistance drop across the resistive opening is lower by a factor of greater than about 5, 10, 20, 50 or 100 relative to the resistance across an unblocked pore. In other cases, the resistance drop across the resistive opening is higher by a factor greater than about 5, 10, 20, 50 or 100 relative to the resistance across an unblocked pore.

In some aspects, the invention relates to devices and methods which allow for multiplex electronic sequencing measurements in a manner that reduces or eliminates cross-talk between the nanopores in the nanopore array. In some cases it is desirable for a nanopore sequencing measurement system to have a pair of drive electrodes that drive current through the nanopores, and one or more measurement electrodes that measure the current through the nanopore. It can be desirable to have the drive electrodes drive current through multiple nanopores in the nanopore array, and have measurement electrodes that are directly associated with each nanopore. We have found that this type of system can be obtained by the incorporation of resistive openings, which connect a reservoir of fluid in contact with the nanopore to a volume of fluid in contact with a drive electrode in a manner that creates a resistive drop across the resistive opening, but allows for fluidic connection and for ion transport between the reservoir of fluid in contact with the nanopore and the volume of fluid in contact with the drive electrode.

These resistive openings can be optimized for several type of operating conditions. For example, in some embodiments it is convenient for the resistive opening to act as a reference resistor, and in some cases it is desirable to have this resistance be well balanced with the sequencing nanopore resistance. One means of attaining this is for the resistive opening to comprise an additional nanopore identical to the sequencing nanopore. In this way the balance between the reference resistive opening and the sequencing nanopore is automatically optimal. In other embodiments it is desirable to minimize the stray series capacitance of the system, and in these cases a low capacitance can be achieved by increasing the thickness of the membrane while at the same time increasing the cross-sectional area of the aperture of the resistive opening. In some embodiments this membrane could be 2 times the thickness of the sequencing nanopore membrane, in still others, it could be 10, 30, 100, 300, 1000, 3000 or 10000 times thicker than the sequencing membrane. It is also of interest that the reference resistive opening be fabricated in a membrane that has a small surface area, as capacitance is typically proportional to surface area. In some embodiments, the reference resistive opening is 10 microns in diameter, in others it is 3 microns in diameter, in others it is 1 micron in diameter. In others there is no membrane and only a resistive opening in an otherwise solid structure.

The effect of a series of resistive openings can be simulated, for example, using a program such as Matlab. Such simulations have been used to demonstrates the ratio of the mean resistance in such a circuit to the standard deviation of the resistance, given N nanopores in parallel, a probability P of each nanopore being open (derived from the duty cycle of current blockage due to passing nucleotides to be ~1/30), and assuming typical resistance values for open and closed nanopores, JACS, 128:1705-1710 (2006). For example, a simulation showed that for N=10 nanopores, one could incorporate a constriction resistance R1 of ≥5e9 ohms for the standard deviation of the resistance to be <1/100 of the mean resistance. Such a resistance could be accomplished, for example, by placing another protein nanopore within a lipid bilayer in the constriction, by having the constriction comprise an opening of ~2-3 nm diameter and 1 nm deep opening, or by using a larger diameter constriction that is deeper than 1 nm. This level of resistance could also be accomplished using nanoporous or fibrous materials. Alternatively, a long narrow channel, e.g. a channel through a polymer such as PDMS can provide a resistive opening. The long narrow channel can have a cross-sectional dimension of about 3 nm to about a micrometer and have an aspect ratio of 1:5, 1:10, 1:100, 1:1000, 1:10,000 or more. Another advantage of the use of a resistive opening is that it can help prevent crosstalk of chemical species between nanopores. For example, resistive openings can prevent exonuclease-excised nucleotides from diffusing into an unwanted nanopore.

In one aspect, the invention comprises a device for determining polymer sequence information comprising: a substrate comprising an array of nanopores; each nanopore fluidically connected to an upper fluidic region and a lower fluidic region; wherein each upper fluidic region is fluidically connected through a resistive opening to an upper liquid volume, wherein the upper liquid volume is fluidically connected to two or more upper fluidic regions.

In some case each lower fluidic region is fluidically connected through a resistive opening to a lower liquid volume, and wherein the lower liquid volume is fluidically connected to two or more lower fluidic regions. In some embodiments the substrate is a semiconductor comprising circuit elements. In some embodiments, either the upper fluidic region or the lower fluidic region for each nanopore or both the lower fluidic region and the upper fluidic region for each nanopore is electrically connected to a circuit element. In some embodiments the circuit element comprises an amplifier, an analog-to-digital converter, or a clock circuit. In some embodiments the resistive opening comprises one or more channels. In some embodiments the length and width of the one or more channels are selected to provide a suitable resistance drop across the resistive opening. In some embodiments the conduit is a channel through a polymeric layer. In some embodiments the polymeric layer is polydimethylsiloxane (PDMS).

The devices of the invention can also include an upper drive electrode in the upper liquid volume, a lower drive electrode in the lower liquid volume, and a measurement electrode in either the upper liquid volume or the lower liquid volume. Alternatively, the devices can include an upper drive electrode in the upper liquid volume, a lower drive electrode in the lower liquid volume, and an upper measurement electrode in the upper liquid volume and a lower measurement electrode in the lower liquid volume.

In some cases, the nanopore, upper fluidic reservoir and lower fluidic reservoir are disposed within a channel that extends through the substrate. In some cases the upper fluidic reservoir and lower fluidic reservoir each open to the same side of the substrate.

In some embodiments, the devices of the invention do not comprise resistive openings.

Figure 3:
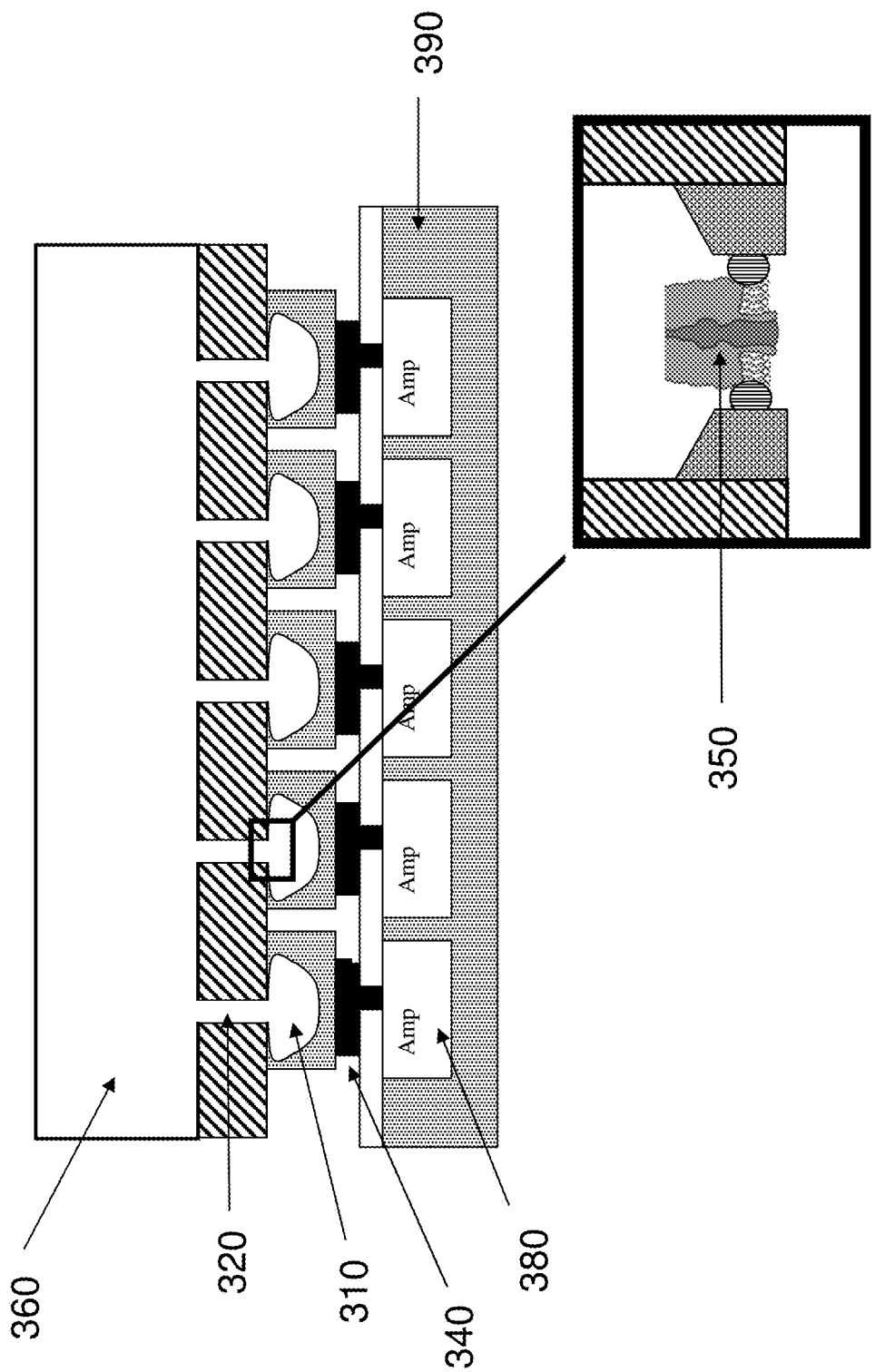
FIG. 3 shows a cross sectional view of an embodiment of a multiplex nanopore sequencing device of the invention having discrete reservoirs.

In some embodiments, the devices comprise discrete reservoirs, wherein each discrete reservoir is associated with one nanopore. In some cases the discrete reservoir can be connected to an upper fluidic region, a lower fluidic region, or both an upper and lower fluidic region of the nanopore. In other cases, the discrete fluidic regions for each nanopore are separated, such that there is no fluidic contact between the regions. FIG. 3 shows a cross sectional view of an embodiment of a multiplex nanopore sequencing device of the invention having discrete reservoirs. The device has an array of pores 320 which hold nanopores 350. As shown, nanopore 350 is disposed at the base of the pore 320. In other embodiments, it could be placed in any other suitable portion of the pore 320 including at or near the top or in the middle region. The nanopores 350 can comprise either solid state nanopores, protein nanopores, or hybrid nanopores such as those described herein. The pores, 320 are in fluidic contact with discrete reservoirs 310 below, and in this embodiment with upper fluid volume 360. In other embodiments, the upper fluidic region can also be a discrete region, associated only with that nanopore. For example, the top surface of the device can have separate wells isolating the pores, or can have hydrophobic barriers between the pores allowing for separate fluidic regions, each associated with one pore. Where each pore has a distinct fluidic region, the drive voltage for transporting the molecules through the pores is supplied to each separate nanopore. The discrete fluidic reservoirs are each connected to electrodes 340 for providing drive current and for measuring electrical properties for sequence determination. In some cases, the electrodes 340 will comprise two electrodes to each discrete reservoir, one to act as a drive electrode, and the other to act as a measurement electrode. In some cases, the inner surface of the discrete reservoir 310 can have a high conductivity electrode such as gold, platinum, or aluminum. In some cases, the electrode can be coated with a dielectric material such as a low K dielectric. The electrodes 340 can be connected to electronic circuitry 380, which can include, for example, amplifiers for amplifying the measured electrical signal. The electronic circuitry can be produced, for example in a semiconductor substrate 390. A device such as that shown in FIG. 3 can be produced using flip chip methods. FIG. 3 shows 5 pores 320 having nanopores 350, but such a device of the invention may have more or fewer nanopores as described herein. The devices may have 10s to 100s to 1000s of pores. The pores can be arranged linearly, or in a two dimensional array structure.

The discrete fluid reservoirs can be of any suitable shape and suitable volume. The dimensions of the discrete reservoirs will generally be on the order of a micron, 10 microns, or 100s of microns.

One aspect of the invention is a polymer sequencing device comprising: a nanopore layer comprising an array of nanopores, each nanopore having a cross sectional dimension of about 1 to 10 nanometers, and having a top and a bottom opening, wherein the bottom opening of each nanopore opens into a discrete reservoir, resulting in an array of reservoirs, wherein each reservoir comprises one or more electrodes; and a semiconductor chip, comprising an array of circuit elements, wherein each of the electrodes in the array of reservoirs is connected to at least one circuit element on the semiconductor chip.

In some embodiments the array of nanopores comprises an array of holes in a solid substrate, each hole comprising a protein nanopore. In some embodiments each protein nanopore is held in place in its hole with a lipid bilayer.

In some cases the top opening of the nanopores open into an upper reservoir. In some cases the circuit elements comprise amplifiers, analog to digital converters, or clock circuits.

Figure 4:
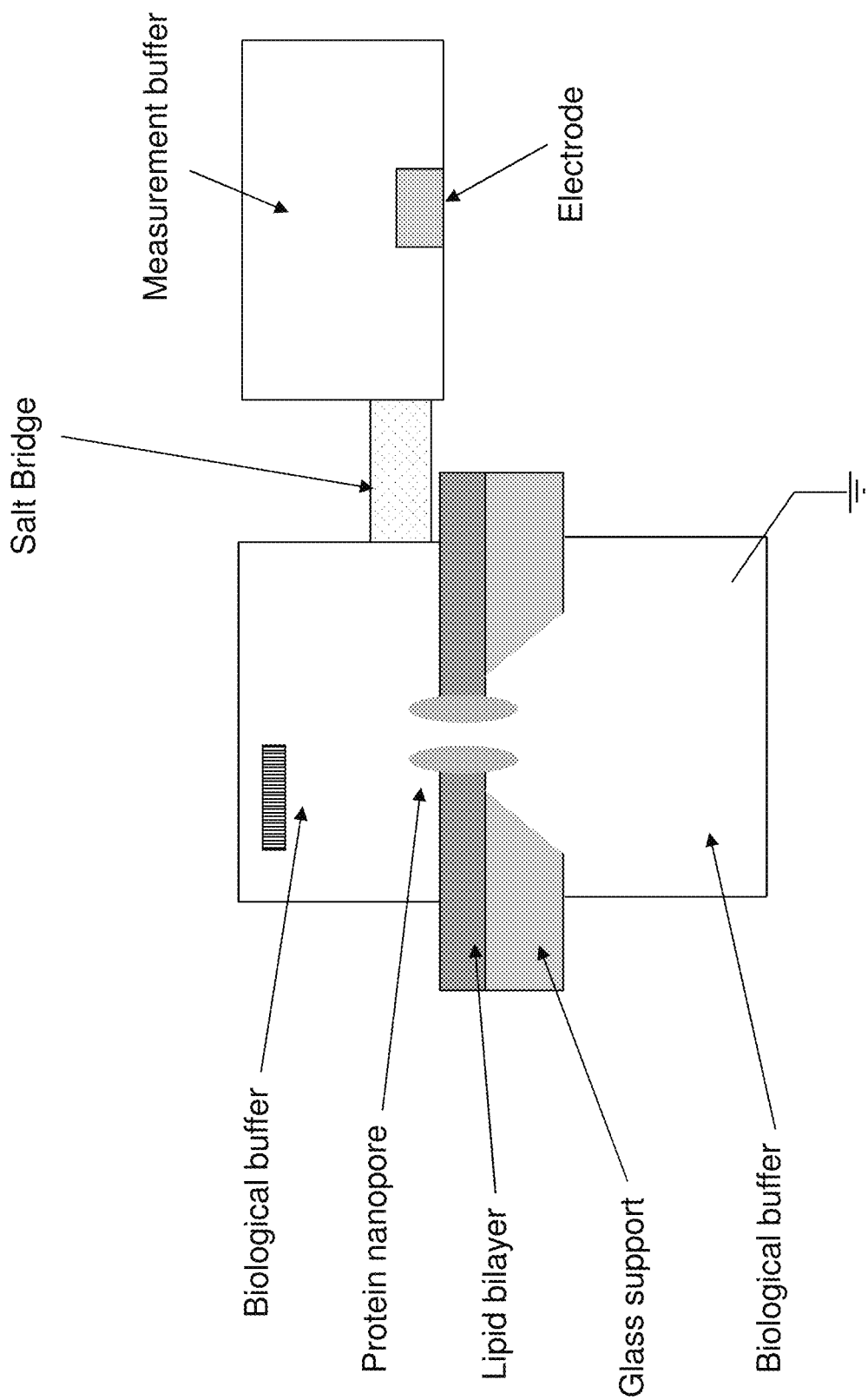
FIG. 4 shows an embodiment of the invention comprising a salt bridge.

In some embodiments the devices of the invention comprise a salt bridge which can be use to isolate liquid regions in the device. For example, a salt bridge can be used in order to provide for one buffer suited for biochemistry, and another suited for electrical measurement. The salt bridge isolation can also prevent sensitive reagents from undergoing electrochemical reactions at the electrodes, which can occur for some compounds at even low voltages. In some cases porous materials, like low-k dielectrics can be used. For example, a salt bridge can be incorporated between a chamber where the nanopore is held, and a chamber where the drive voltage and the resulting currents are measure. The salt bridge allows for the composition of each solution to be optimized to provide ideal biochemical behavior and ideal electrical measurement somewhat separately. FIG. 4 shows an embodiment comprising a salt bridge. In this embodiment, a biological buffer is in the fluid regions that are in direct contact with the protein nanopore. A salt bridge provides an ionic connection between the biological buffer and a fluid region having a measurement buffer. The fluid region comprises an electrode which acts as a drive electrode, and in some cases also acts as a measurement electrode.

In some embodiments, the devices utilize MESA structures. These structures can be used, for example, when building electrical cells straight onto either a silicon or an SOI wafer. The MESA designs as known in the CMOS industry can be used to guarantee insulation of the different cells in the device. See, e.g. U.S. Pat. No. 5,049,513.

Hybrid Nanopores—Surface Functionalization

One aspect of the invention is the use of a hybrid solid state-protein nanopore in the multiplexed nanopore sequencing device. We describe herein methods for functionalizing a solid-state pore either to enhance its ability to detect or sequence a polymer such as DNA, or to enable hybrid protein/solid state nanopore.

Two approaches are typically used for nanopore polymer (DNA) sequencing: the first uses a protein nanopore (e.g. alpha-hemolysin, or MspA) embedded in a lipid membrane, and the second uses a solid-state nanopore. Protein nanopores have the advantage that as biomolecule, they self-assemble and are all identical to one another. In addition, it is possible to genetically engineer them to confer desired attributes or to create a fusion protein (e.g. an exonuclease+alpha-hemolysin). On the other hand, solid state nanopores have the advantage that they are more robust and stable compared to a protein embedded in a lipid membrane. Furthermore, solid state nanopores can in some cases be multiplexed and batch fabricated in an efficient and cost-effective manner. Finally, they might be combined with micro-electronic fabrication technology.

One aspect of the invention comprises techniques for treating the surface of solid-state nanopores in order to either improve their sequencing performance or to enable the creation of an hybrid protein/solid-state nanopore. In such a hybrid, the solid-state pore acts a substrate with a hole for the protein nanopore, which would be positioned as a plug within the hole. The protein nanopore would perform the sensing of DNA molecules. This hybrid can the advantages of both types of nanopores: the possibility for batch fabrication, stability, compatibility with micro-electronics, and a population of identical sensing subunits. Unlike methods where a lipid layer much larger than the width of a protein nanopore is used, the hybrid nanopores are generally constructed such that the dimensions of the solid state pore are close to the dimensions of the protein nanopore. The solid state pore into which the protein nanopore is disposed is generally from about 20% larger to about three times larger than the diameter of the protein nanopore. In preferred embodiments the solid state pore is sized such that only one protein nanopore will associate with the solid state pore. An array of hybrid nanopores is generally constructed by first producing an array of solid state pores in a substrate, selectively functionalizing the nanopores for attachment of the protein nanopore, then coupling or conjugating the nanopore to the walls of the solid state pore using liker/spacer chemistry.

FIG. 5 shows an embodiment of the invention illustrating the chemistry used to produce an array of hybrid nanopores of the invention. The solid state pore can be constructed of one or multiple materials. In FIG. 5, two materials, S1 and S2 are used. In other cases, a single material can be used. Where two materials are used, for example, both the top and the bottom S1 layers can be fabricated using Al/AlOx, and S2 can comprise a gold layer. S2 can be used as a secondary material to facilitate controlled surface modification for attachment of the protein nanopore. This control would allow for more precise control over the position of an attached protein inside a nanopore. In one embodiment, phosphonate passivation chemistry specific towards S1-Aluminum is used, and thiol chemistry, specific to the gold portion of the sidewall, S2 is used. The thiol groups functionalizing S2 comprise pendant groups that attach to the linker/spacer which can be, for example, a protein or other biological molecule disposed at a controlled distance from the solid state pore sidewall and bottom/top. The size of the linker spacer molecule can be tailored to provide the appropriate spacing, for example by controlling molecular weight. By using organic molecules such as proteins, the spacers have enough flexibility to accommodate the different spacings which can result, for example from manufacturing variances in the size of the solid state pore. This control can be useful for controlling reagent diffusion in/out of the hybrid nanopores as well as spacing the protein to eliminate conformational restrictions and to potentially maximize signal to noise within a finite observation volume. The parameters can be controlled by adjusting the dimensions labeled as a, b, c, d, and e on the schematic illustration.

One aspect of the invention comprises devices and methods for obtaining a solid state pore sequencing device having a high portion of pores having only one nanopore per solid state pore. Protein nanopores embedded in a lipid membrane can suffer from the issue of Poisson-loading (loading of a single protein nanopore in each lipid membrane follows Poission statistics), in this case only a single protein nanopore will fit into each solid-state nanopore. With the present invention, the pores can be made and functionalized such that one nanopore is generally present in one solid state pore.

One aspect of the invention comprises the use of surface monolayers on a solid state pore. In some embodiments, SiN substrates are treated using functional methoxy-, ethoxy-, or chloro-organosilane(s) such as —NHS terminated, —NH2 (amine) terminated, carboxylic acid terminated, epoxy terminated, maleimide terminated, isothiocyanate terminated, thiocyanate terminated, thiol terminated, meth(acrylate) terminated, azide, or biotin terminated. These functional groups for the non-specific immobilization of aHL or another protein. In some cases, S1 is functionalized to have only passive, inactive functional groups on the S1 surface. These functional groups can include polymeric chains at controlled length to prevent non-specific adsorption of biological species and reagents across the S1 surface. Some examples of these functional groups are PEG, fluorinated polymers, and other polymeric moieties at various molecular weights. This chemistry is schematically illustrated as (X) and typically provides a passive layer to prevent non-specific noise throughout the detection signal of the hybrid nanopore.

In some embodiments, SiOx substrates are treated using functional organosilane(s) such as —NHS terminated, —NH2 (amine) terminated, carboxylic acid terminated, epoxy terminated, maleimide terminated, isothiocyanate terminated, thiocyanate terminated, thiol terminated, meth(acrylate) terminated, azide, or biotin terminated. These functional groups are useful for non-specific immobilization of aHL or another protein. For specific control over location and conformation of such proteins inside a hybrid nanopore, S1 can be functionalized to have only passive, inactive functional groups on the S1 surface. These functional groups may include polymeric chains at controlled length to prevent non-specific adsorption of biological species and reagents across the S1 surface. Some examples of these functional groups are PEG, fluorinated polymers, and other polymeric moieties at various molecular weights. This chemistry is schematically illustrated as (X) and typically provides a passive layer to prevent non-specific noise throughout the detection signal of the hybrid nanopore.

In some embodiments, ALD alumina (as substrate) is modified using phophonate chemistry. This includes phosphate, sulfonate, and silane chemistries since they all have weak affinities towards AlOx surfaces as well. The phosphonates can have any of the above chemistries on the terminus for surface treatment.

Where gold is the substrate, the invention comprises the use of functionalized thiol chemistries. The S2 layer is positioned to control the depth as which the protein or biological of choice is immobilized within the hybrid nanopore. The distance e in the figure controls the spacing of the linker/spacer such as a protein within the hybrid nanopore. The size of the liker/spacer can be adjusted by selecting the appropriate polymeric or rigid chemical spacer length of the linker between S2 and the protein attachment point. For example, this parameter can be controlled via the molecular weight and rigidity of the polymeric or non-polymeric linker chemistry used. Also, this can be controlled by the S2 electrode protrusion into hybrid nanopore. The linker chemistry used to attach alpha-HL or another protein to the hybrid nanopore sidewall substrate can consist of the pendant groups mentioned above, but may or may not also include a polymeric or rigid linker that further positions the protein into the center of the nanopore. This linker can distance can be controlled via control over the molecular weight and chemical composition of this linker. Some examples can include polypeptide linkers as well as PEG linkers.

The chemistries described above can be used as a conjugation mechanism for attachment of large molecule sensors such as proteins or quantum dots or functionalized viral templates or carbon nanotubes or DNA, if the nanopore is 10 s-100 s of nanometers in diameter. These large molecule sensors can be used to optically or electrochemically enhance detection via molecule-DNA interactions between H-bonds, charge, and in the case of optical detection via a FRET, quenching, or fluorescence detection event.

For example, if the nanopores are ~1 nm to 3 nm in diameter, the acid terminated silanes can be used to functionalize pores for better control over DNA translocation. Further, PEGylation with short PEGs may allow for passivation of pores to allow for ease of translocation.

In some embodiments, the invention provides surface chemistries for the attachment of proteins such as alpha-hemolysin to the solid state pore surface. Functional surface chemistries described above can be used to either A) conjugate protein via an engineered or available peptide residue to the nanopore surface, to anchor the protein or B) to functionalize the surface chemistry such that the hydrophilic region of that chemistry is presented to the surface to facilitate lipid bi-layer support. White et al., J. Am. Chem. Soc., 2007, 129 (38), 11766-11775, show this using cyano-functionalized surfaces, but any hydrophilic surface chemistry such as cyano-, amino-, or PEG terminated chemistries should support this function.

Specifically, the covalent conjugation of alpha hemolysin (or other proteins) to the surface of a solid state pore can be achieved via cystine or lysine residues in the protein structure. Further conjugation could be achieved via engineered peptide sequences in the protein structure or through CLIP or SNAP (Covalys) chemistries that are specific to one and only one residue engineered onto the protein structure. In more detail, protein lysine residues can be conjugated to NHS-containing chemistries, cystine residues to maleimide containing surface chemistries or SNAP to benzyl guanine/SNAP tags introduced onto the protein and CLIP to benzyl cytosine tags introduced onto the protein of choice.

One aspect of the invention comprises controlled and un-controlled polymerization approaches on pores. The synthesis of silane chemistries that involve silane monolayers consisting of a photocleavable/photoinitiatable group that can be used to graft polymers from the surfaces of nanopores is known. One example is from this literature is N,N (diethylamino)dithiocarbamoylbenzyl(trimethoxy)silane. While this work has been primarily conducted on derivatized SiOx surfaces (Metters et al) or derivatized polymeric surfaces (Anseth/Bowman et al), polymeric chains can potentially be grown from the sidewalls of nanopores to control diameter, functionality, DNA translocation speed, and passivation for optical and/or electrochemical detection platforms. The initiation kinetics can be slowed down using a chain transfer or radical termination agent such as a tetraethylthiuram disulfide or a thiol, to achieve potential for more precise chain lengths on the functionalized nanopore.

Uncontrollable grafting of polymers to the surface of nanopores could be achieved via polymerization of functional chains (in solution) that can be attached via conjugation through any of the silanes listed in above. This achieves the same functional nanopore via a "grafting to" approach instead of a "grafting from" approach.

The polymerization techniques described above can also be used to support lipid bi-layer formation for protein immobilization support or for direct covalent attachment of proteins to surfaces as discussed in Ib1-2. The interesting facet of grafting polymer chains to or from the surface of a nanopore is the ability to control pore diameter, function, mobility (diffusion of molecules through), by controlling molecular weight, density, length, or multifunctionality of these chains. This offers a more fine-tuned way to control bi-layer formation for aHL or methods for covalently attaching proteins with polymeric chains that can space the protein from side-walls of the nanopore substrate.

If using a polymeric approach described above, poly (acrylic acid) PAA or additional charged polymeric chemistries like NIPAAM or other hydrogels can be used to functionalize nanopores to create an electro-osmotic flow valve that changes inner-diameter based off pH or directionality via charge potential. This approach can be useful for governing the rate at which DNA translocated through a modified solid state pore and also to reanalyze DNA multiple times.

The devices of this invention can use H-bond interactions between functionalized electrodes with phosphate groups on ssDNA passing through the nanopore as described by Lindsay et al.

As described above, the hybrid nanopores of the present invention are generally prepared such that only a single protein nanopore will associate with each solid state pore by appropriately sizing the solid state pore and by using linker/spacer chemistry of the appropriate dimensions. In some cases, the solid state pores can accommodate more than one protein nanopore, and other approaches are used to ensure that only one protein nanopore is loaded into one pore, hole, or aperture in the device. Both the hybrid nanopores described above and the other nanopores used herein can include the use of a lipid layer for supporting the protein nanopore and acting as a spacer within the solid state pore.

In some cases loading can be done at a concentration at which a Poisson distribution dictates that at most about 37% of the apertures will have a single nanopore. Measurements on the pores will reveal which of the pores in the array have a single protein nanopore, and only those are used for sequencing measurements. In some cases loadings of single protein nanopores higher than that obtained through Poisson statistics are desired.

In some cases, repeated loading at relatively low concentrations can be used in order improve fraction of single protein nanopores. Where each of the pores can be addressed independently with a drive voltage, each pore could be connected to a fluidic conduit that supplies protein nanopores at a low concentration to the solid state pores, where the each conduit has a valve which can be controlled to allow or shut of the flow of fluid. The current across the solid state pore is monitored while the flow of fluid is enabled. Measurement of current while loading a lipid bilayer has been shown, see, e.g. JACS, 127:6502-6503 (2005) and JACS 129:4701-4705 (2007). When a protein nanopore becomes associated with the nanopore, a characteristic current/voltage relationship will indicate that a single pore is in place. At the point that a protein nanopore is associated, the flow of the liquid is interrupted to prevent further protein nanopore additions. The system can additionally be constructed to apply an electrical pulse that will dislodge the protein nanopore from the solid state pore where the electronics indicates that more than one protein nanopore has been incorporated. Once the multiple protein nanopores are removed, the flow of protein nanopores to the solid state pore can be resumed until a single protein nanopore is detected. These systems can be automated using feedback to allow the concurrent loading of multiple wells in the array without active user intervention during the process.

In some cases, steric hindrance can be used to ensure that a single protein nanopore is loaded into a single solid state pore. For example each protein nanopore can be attached to a sizing moiety that the size of the protein nanopore and the sizing moiety is such that only one will fit into each solid state pore. The sizing moiety can comprise, for example, one or more of a bead, nanoparticle, dendrimers, polymer, or DNA molecule whose size is on the order of the region between the protein nanopore and the solid state pore. These methods can be used in combination with membranes such as lipid bilayers. In some cases, the sizing moieties are removed after loading and before measurement. Alternatively, in some cases, the sizing moieties can remain associated with the protein nanopores after loading. In some embodiments, multiple sizing moieties are employed. Where membranes such as lipid bilayers are employed, each protein nanopore can be functionalized with arms, e.g. dendrimers-like arms, each having a membrane inserting moiety at its end (for example a non-porous transmembrane protein). The membrane inserting moieties will prevent the association of a second protein nanopore complex from entering the bilayer.

Electrostatic repulsion can also be used in order to obtain single protein nanopore loadings. Each polymer nanopore can be attached to a bead, nanoparticle, dendrimers, polymer, or DNA molecule that is highly charged. The charged protein nanopore complex in the pore will repel other charged protein nanopore complexes. In some cases, the charged moieties are removed after loading and before measurement. Alternatively, in some cases, the charged moieties can remain associated with the protein nanopores after loading. Charged protein-nanopore complexes can also be used with the systems in which attachment of the protein nanopore into the pore is actively monitored. The charged moiety can be used to actively remove the protein nanopore from the solid state pore using an electric field.

Optical trapping can also be employed in order to obtain single protein nanopore loadings. Optical traps can be used to capture complexes comprising a bead and a single nanopore protein. The bead can then be positioned over the solid state pore and released. Multiple pores can be loaded by sequential loading using a single optical trap, or an array of optical traps can be used to load multiple pores concurrently. The bead size and the laser power of the optical trap can be chosen such that no more than one bead at a time can be captured in the optical trap. After loading the protein nanopore into the solid state pore, the bead can be cleaved and washed away.

The protein nanopore to be inserted can be wild type or genetically engineered. The protein nanopore can comprise a fusion protein with an exonuclease or can be chemically linked to an exonuclease for sequencing using an exonuclease as described herein. Where an exonuclease is attached, it may have a DNA molecule, such as a template DNA bound to it at the time of loading. This DNA molecule can act as a moiety to provide steric or electrostatic hindrance as described above.

III. Methods of Fabricating Nanopore Sequencing Devices

One aspect of the invention involves the integration of nanopore microfluidics with CMOS technology. The integration of these technologies can be important obtaining the cost and reproducibility required for mass-production of a parallelized electronic nanopore sequencing system.

One aspect of the invention is a method of fabricating a multiplex polymer sequencing device having microfluidic and electronic features from a semiconductor substrate comprising: obtaining a semiconductor substrate; processing the semiconductor substrate to create an array of microfluidic features, wherein the microfluidic features are capable of supporting nanopores; and subsequently creating circuit elements on the substrate that are electronically coupled to the microfluidic features. In some cases the circuit elements are CMOS circuit elements. In some cases the CMOS circuit elements comprise amplifiers, analog to digital converters.

We have found that in fabricating a nanopore polymer sequencing device from a semiconductor substrate in which the semiconductor substrate comprises both microfluidic and electronic features. In such cases, we have found that in some cases there are advantages to first creating an array of microfluidic features, and only subsequently adding the electronic features, for example by CMOS processing. One advantage of this approach is that the electronic features are not subjected to the conditions required for creating the microfluidic features, including high temperatures and harsh chemical agents. Processing steps, such as planarization can be employed after creating the microfluidic features and before producing the electronic features.

One aspect of the invention is a method of fabricating a polymer sequencing device comprising the following steps in the order presented: obtaining a semiconductor substrate; processing the semiconductor substrate to create an array of CMOS circuits, without carrying out an aluminum deposition step; processing the semiconductor substrate having the CMOS circuits to produce microfluidic features, wherein the microfluidic features are capable of supporting nanopores; and subsequently performing an aluminum deposition step to create conductive features. In some cases the processing of step (c) to create the microfluidic features subjects the semiconductor substrate to temperatures greater than about 250° C.

We have found that in fabricating a nanopore polymer sequencing device form a semiconductor substrate having both microfluidic and electronic elements, that in some cases it is advantageous to prepare the electronic elements, for example, by CMOS, and subsequently prepare microfluidic features. We have found, however, that where this is done, any processes involving the introduction of aluminum should generally not be performed until after the creation of the microfluidic features. This approach has the advantage that the final device has aluminum features that may be advantageous for sensitive electronic measurements, but that the aluminum is introduced after the fabrication of the microfluidic features on the substrate. This process is advantageous in that aluminum features can be damaged above about 200 or 250, limiting the ability to effectively create microfluidic features without damaging the aluminum features.

The integration of an array of electrical/CMOS components (amplifiers) and bio/fluidics components (membranes/solutions/enzymes etc) can be achieved as described herein with a flip-chip technology approach. In this approach component layers are processed separately throughout some or all of their production processes, and are matched at or near the end of the assembly process. The separate process flows can be optimized independent of each other. In some embodiments, the process allows for the CMOS layer to be outsourced to a semiconductor foundry where, for example, only standard processes are required.

Figure 6:
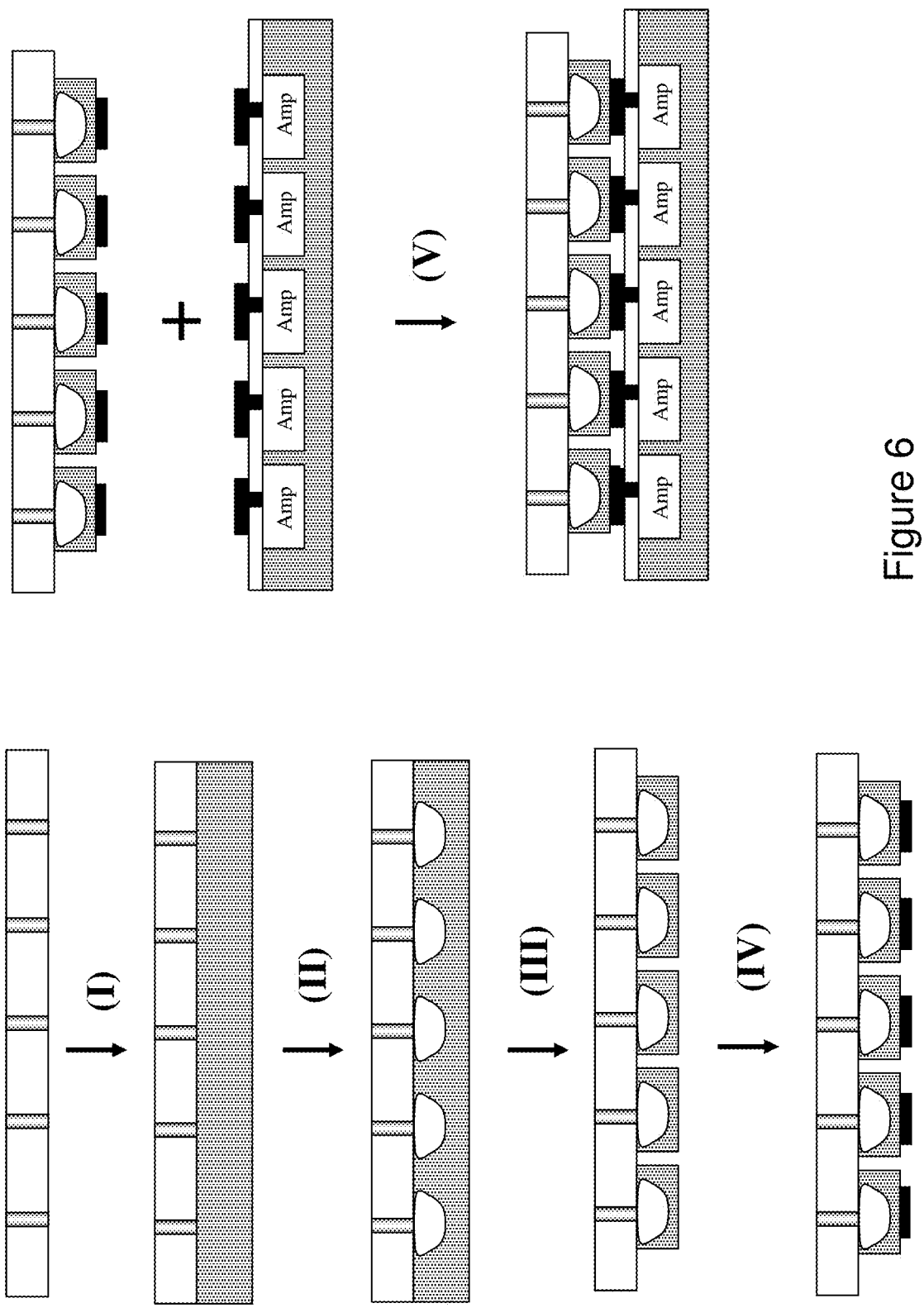
FIG. 6 shows a process of the invention wherein a nanopore/electrode is produced with a self-aligned etching process.

In one embodiment, the nanopore/electrode is produced with a self-aligned etching process. A schematic for one embodiment of this process is shown in FIG. 6. The process can start with an insulator layer such as a glass wafer. Channels and/or other microfluidic features are etched into the glass, for example with a highly directional dry etch process. As shown in FIG. 6, step (I), this insulator substrate can then be bonded with a wafer bond process a wafer (e.g. silicon wafer). This wafer can be used, for example to pattern electrodes.

As shown in step (II) a selective wet etch process can be used to create a self-aligned array of cavities, or discrete regions, in the silicon wafer. If necessary, the Si wafer can be thinned as shown in step (III) to remove excess material. As shown in steps (III) and (IV), individual electrodes can be defined by patterning the Si wafer with photolithography and a dry etch. An advantage of this self-aligned etching process, is that the alignment of the etch mask and the glass holes/cavities can be done without highly accurate alignment processes. Metal pads can be evaporated on each electrode to provide better electrical contact. This can be done before or after the electrode etch step. The process can be used to create an individually contained electrode for each measurement site.

One aspect of the invention is a method for fabricating a polymer sequencing device comprising: producing an insulator layer having microfluidic elements comprising an array of pores extending through the insulator; bonding the insulator layer with a semiconductor layer; exposing the semiconducting layer to etchant through the pores in the insulator to produce discrete reservoirs in the semiconductor layer; removing portions of the semiconductor layer to isolate the discrete reservoirs, and providing electrical contacts that allow current to be directed to each of the discrete reservoirs; bonding an electric circuit layer to the semiconducting layer such that the electric circuits on the electric circuit layer are electrically connected to the electrical contacts on the semiconductor layer.

In some cases the method further comprising the step of adding nanopores into each of the pores. The nanopores can comprise solid state nanopores, protein nanopores, or hybrid solid state/protein nanopores. In some cases the method comprises the use of two or more electrodes within the discrete reservoir.

One aspect of the invention is a method for fabricating a polymer sequencing device comprising: producing an insulator layer having microfluidic elements comprising an array of pores extending through the insulator; bonding the insulator layer with a semiconductor layer wherein the semiconducting layer comprises an array of wells corresponding to the pores on the insulator layer, whereby the bonding produces an array of discrete reservoirs; removing portions of the semiconductor layer to isolate the discrete reservoirs, and providing electrical contacts that allow current to be directed to each of the discrete reservoirs; and bonding an electric circuit layer to the semiconducting layer such that the electric circuits on the electric circuit layer are electrically connected to the electrical contacts on the semiconductor layer.

An alternative embodiment involves starting to with a Si wafer, growing a thick field oxide on top of the wafer, and patterning the oxide as was done above for the insulator layer. The subsequent steps described above can be used to produce a nanopore array.

In some embodiments, the signals coming out of the electrodes will be amplified in a CMOS amplifier stage. Each electrode can be matched up with its own amplifier stage by using flip chip technology as shown in step (V) of FIG. 6. In this approach a CMOS amplifier array is patterned on a Si wafer, with pitch and dimensions matching the electrode array on the bio component. The top of the CMOS chip consists of a matching array of electrodes (metal I/O pads). The input/output pads on the amplifier chip are bonded to the matching electrodes of the bio chip assembly. This can be done with solder bumps, thermally or ultrasonically.

In some embodiments microfluidic features can be created in the semiconductor substrate prior to wafer bonding. FIG. 7 shows the creation of microfluidic features. In step (I) an array of wells is created in a semiconductor substrate. In step (II), an insulator layer having microfluidic elements and pores extending through the insulating layer is wafer bonded with the semiconductor substrate such that the array of pores aligns with the array of wells to produce an array of cavities. In some embodiments, circuits are created on the semiconductor substrate as described above, for example using CMOS processes.

In some aspects of the invention, a SOI wafer is used as the substrate for creating the nanopore sequencing device. Fore example, with an SOI substrate having a top silicon layer, an insulator (oxide) layer, and a bottom silicon layer, the top silicon can be used as a top electrode, or a top electrode can be built onto the top electrode. The intermediary oxide layer can be used as the layer which contains the nanometer scale aperture, such as a nanopore protein within a supporting lipid bi-layer. In some embodiments, the bottom silicon can serve as serve as a ground. Once the SOI based device is constructed, polymeric materials such as polydimethylsiloxane can be used to produces microfluidic features such as channels and reservoirs. For example, in some cases, the device could be sealed with simple PDMS chips.

In some embodiments, electronic circuits and electrodes can be built into top and/or the bottom silicon layer, and the circuits can be electrically coupled to the fluidic regions surrounding the nanopore. In one embodiment, the top silicon in the SOI wafer is used to build an op-amp, which can be used to boost the signal prior to measuring the current. In some cases, full CMOS circuitry can be incorporated. In some cases, less complex circuitry can be incorporated, for example with the inclusion of a simple op-amp. The op-amp could provide some a benefit of noise immunity. The electric circuits on the chip, for example, the op-amp would generally be electrically isolated from the fluid, either through a dielectric coating (Si3N4, SiO2) or by a PDMS chip.

Figure 8:
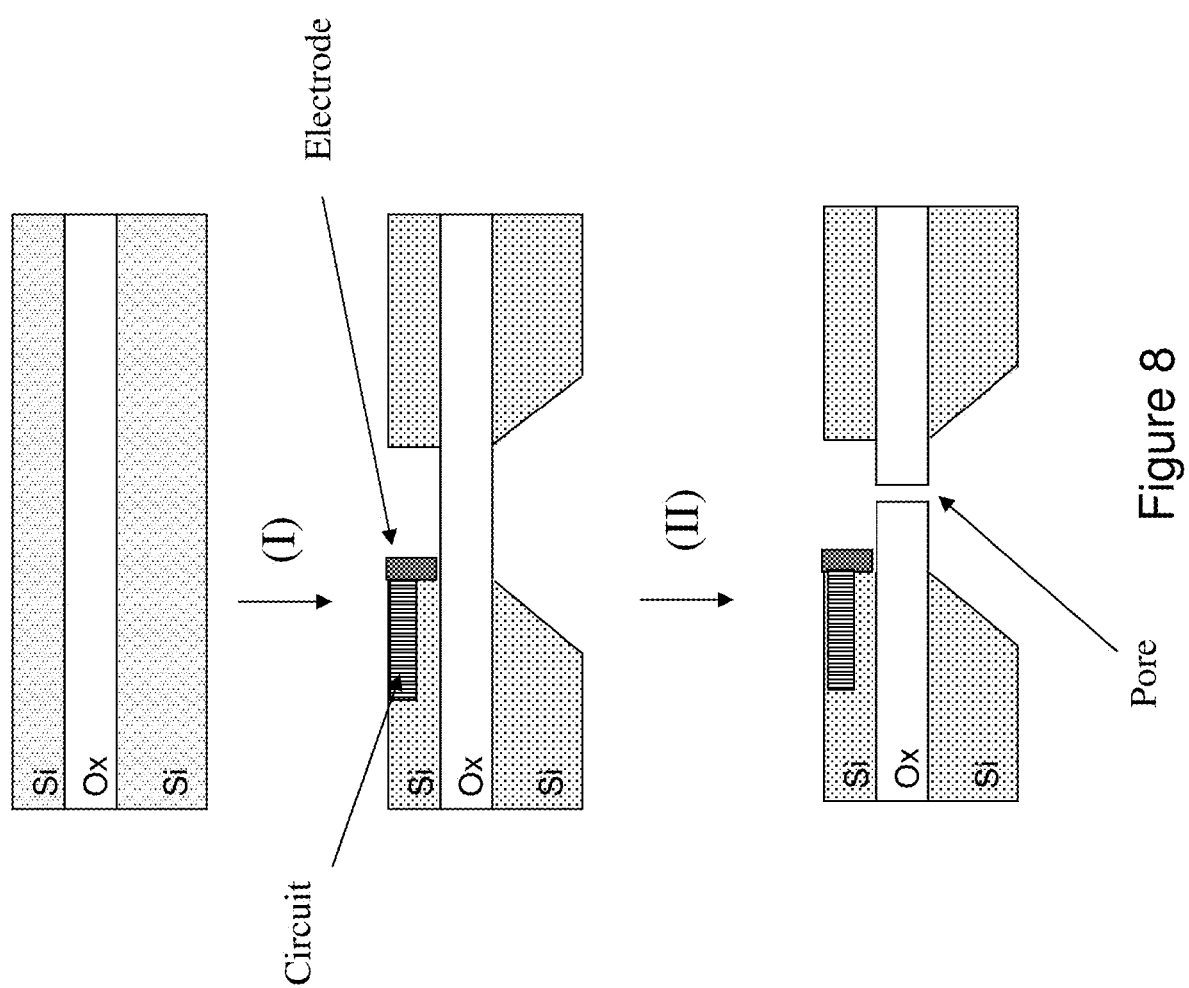
FIG. 8 shows a schematic for a process for producing nanopore arrays using an SOI wafer.

FIG. 8 shows a schematic for a process using an SOI wafer. In step (I), portions of the top silicon layer and the bottom silicon layer are removed to expose regions of the insulator (oxide) layer. This process can produce, for example, an array of regions in which the insulator is exposed on both sides. Step (I) also comprises the addition of circuits and electrodes into the top silicon layer. In some embodiments, electrodes and/or circuits can also be added to the bottom layer. In step (II) of FIG. 8, a pore is created in the insulator. This pore can be used to hold the nanopore of the invention which can be fabricated into the pore, or added to the pore subsequently as known in the art and as described herein.

Figure 9:
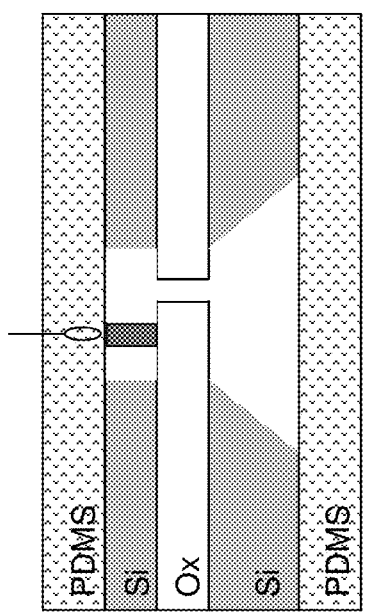
FIG. 9 illustrates how polymers such as PDMS can be used to fluidically seal portions of the device.

FIG. 9 illustrates that polymers such as PDMS can be used to fluidically seal portions of the device. In some cases, as shown in FIG. 9, electrical connections can be provided to electrodes on the device thought the polymer layers.

In some embodiments, the devices of the invention are built having a common ground design. Having a common ground avoids the complexity associated with providing separate pairs of electrodes for each well. In some cases, the bottom of each of the cells is electrically connected to provide a common ground. The ground produced in this manner could be floated to the best potential for the experiment. For example, as the reaction progresses, and species are generated, the potential of the solution may change.

In some aspects of the invention a structure which provides 4-point probing is created. 4-point probes are well known in the art to provide for accurate electrical measurements. The 4-point probe designs of the invention can be produced on glass wafers with electrodes such as gold (Au) or platinum (Pt) electrodes. They can also be produced on SOI or SOI-like wafers. In the 4 point probe designs of the invention, two large electrodes provide the drive current, and two smaller electrodes are used to measure potential drop across the bi-layer. As described herein, in some embodiment, the 4-point measurements of the invention involve using drive electrodes which drive the current through multiple nanopores, while having pairs of measurement electrodes for each of the nanopores. The smaller electrodes can be connected to a high impedance circuit to get good quality measurement characteristics while the drive electrodes are connected to a stable power supply.

One aspect of the invention is a method for fabricating a polymer sequencing device comprising: obtaining an SOI substrate comprising having a top silicon layer, an insulator layer, and a bottom silicon layer; processing the top silicon layer and bottom silicon layer to remove portions of each layer to produce an array of exposed regions in which both the top and bottom surfaces of the insulator layer are exposed; processing the top silicon layer or the bottom silicon layer or both the top silicon layer and bottom silicon layer to add electrodes and electrical circuits; and processing the insulator layer to produce an array of pores through the exposed regions of the insulator layer.

In some cases the method further comprises adding polymer layers to produce microfluidic features. In some cases the method further comprises inserting a nanopore into the pores in the insulator layer.

Where a protein nanopore such as alpha hemolysin is used as the nanopore, the nanopores can be fabricated by, for example, coating a portion of a pore within the device with a primer to which the lipid layer or other supporting linker/spacer will associate. In some cases, the level of a solution that is in contact with the holes into which the pores are to be deposited can be raised or lowered such that the surface of the liquid is disposed within the hole at the desired level. Surface active agents on the liquid can then react with the nanopore at the level at which the surface of the liquid contacts the pore. This can create a functionalized region of the hole that can be used to specifically interact with the lipid layer or linker/spacer.

IV. Nanopore Sequencing Systems

The invention includes sequencing system which incorporate the devices and methods described herein. The systems of the invention incorporate the multiplex nanopore polymer sequencing device described herein, and also include a processing system for driving the electronics, and a processing system for gathering, storing, and analyzing the data produced.

Generally, the raw data from the sequencing run will be processed by various algorithms in order to correlate the electronic measurements with the sequence of the polymer. Some algorithms that can be used to increase the base calling capability of the devices are described herein, others are known in the art. In some cases, the systems of the invention incorporate feedback capability, allowing for changing the sequencing conditions dynamically due to measured signals. Some algorithms for dynamic measurements are described herein. The systems of the invention will also provide for handling and introducing samples into the devices.

V. Methods of Nanopore Sequencing

The invention comprises methods of sequencing using the multiplex polymer sequencing devices described herein.

Enzymatic Control of Translocation Rate

Figure 10:
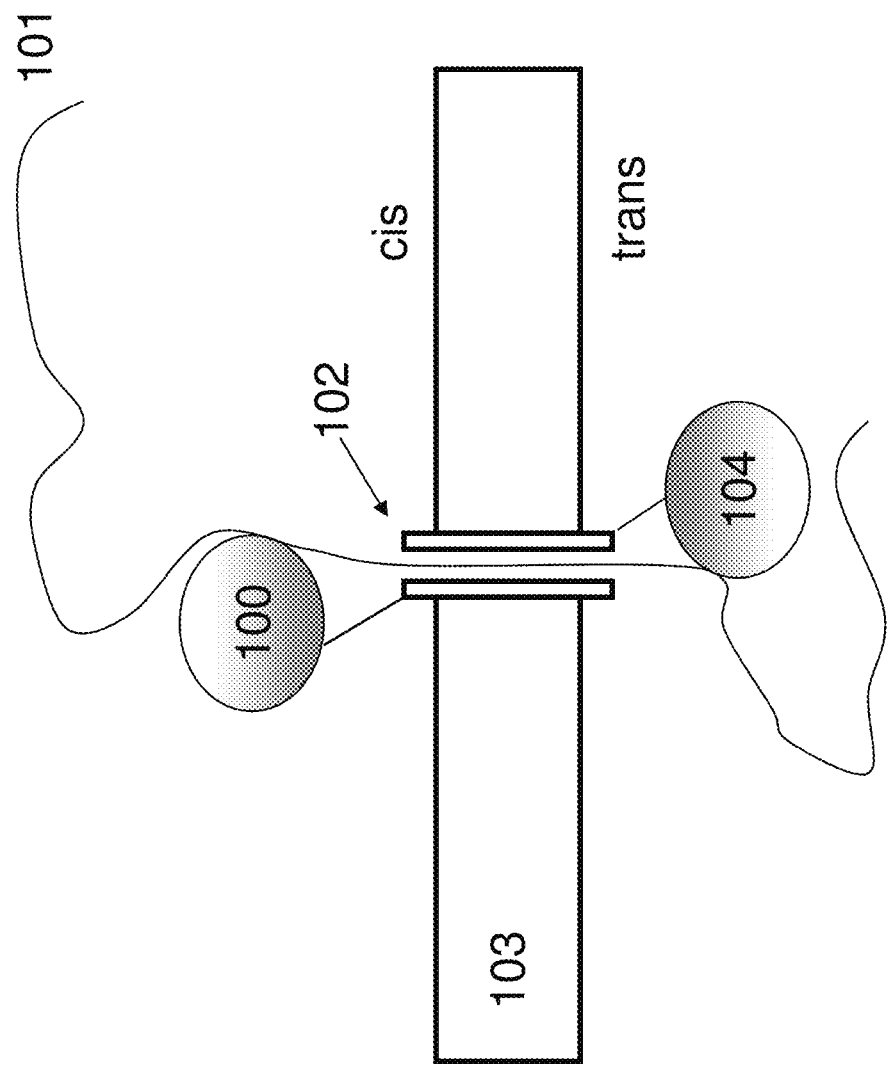
FIG. 10 shows the passage of DNA or RNA translocating under an applied voltage though a nanopore structure within a physical barrier.

One aspect of the invention comprises controlling the translocation of a polymer molecule through the nanopore. For the purposes of single molecule sequencing it can be advantageous to control the translocation of DNA through nanopore structures under applied voltage. See, for example US Patent Application 2006/0063171. Protein components on either the cis or trans side of the nanopore can be utilized to control the rate of the translocation through the nanopore, which can facilitate certain sequence detection methods. Shown in diagrammatic form in FIG. 10 is the passage of DNA or RNA (101) translocating under an applied voltage though a nanopore structure (102) within a physical barrier (103). Proteinaceous components can be located on either or both sides of the nanopore structure (100, 104) to interact with the translocating nucleic acid strands. Optionally, one or more of the interacting components can be covalently, or non covalently tethered to the nanopore structure (102) or barrier (103) as indicated below.

Figure 11:
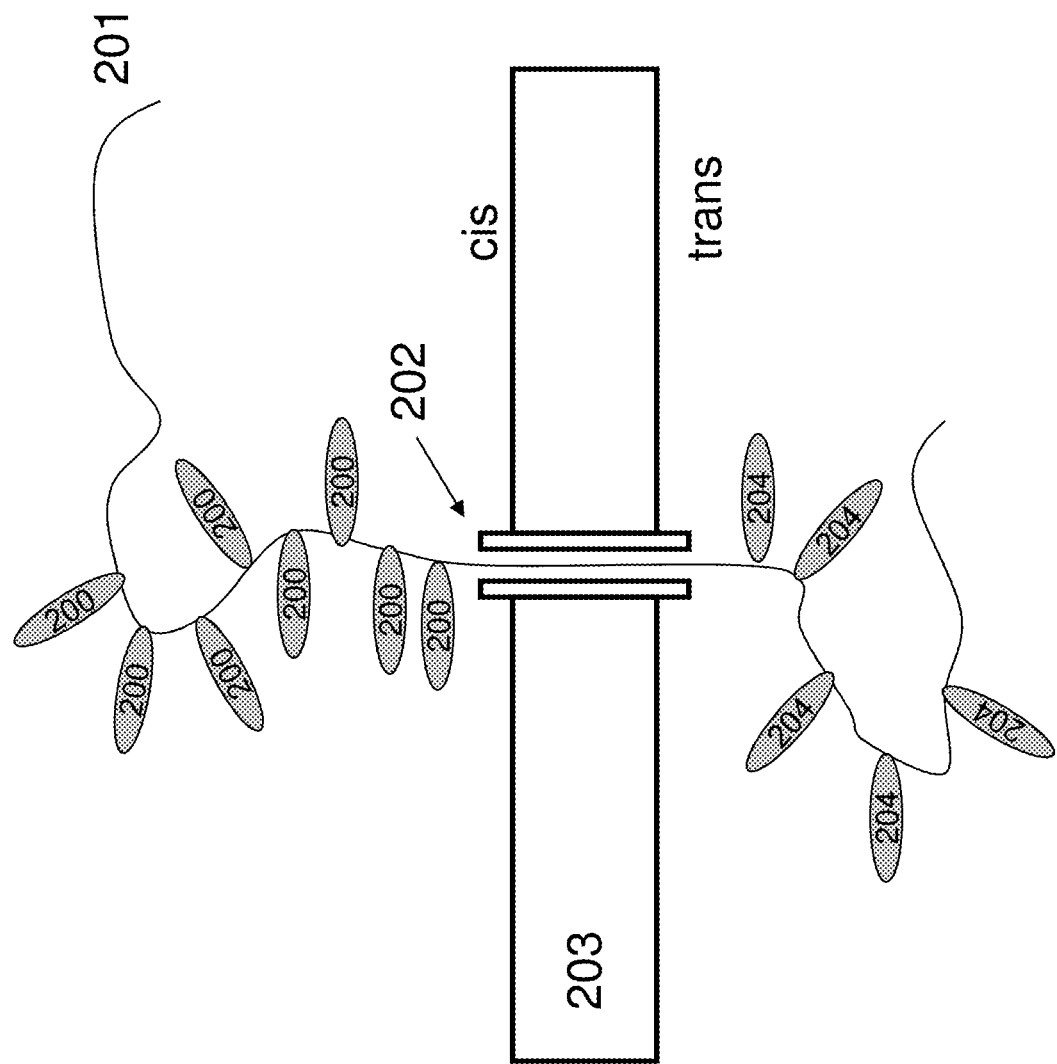
FIG. 11 shows the passage of DNA or RNA translocating under an applied voltage though a nanopore structure within a physical barrier where the barrier comprise DNA binding proteins.

The proteins can be chosen from a host of DNA or RNA metabolizing or translocating enzymes (see, e.g., FIG. 10), or DNA or RNA binding proteins (see, e.g., FIG. 11). For example, these enzymes can be chosen from various polymerases including, but not limited to, phi29 DNA polymerase, T7 DNA pol, T4 DNA pol, E. coli DNA pol 1, Klenow fragment, T7 RNA polymerase, and E. coli RNA polymerase, as well as associated subunits and cofactors. The nucleic acid strand translocating through the nanopore can be comprised of either the template or a nascent strand synthesized by the polymerase, e.g., a displaced nascent strand (e.g., from a rolling circle amplification reaction) or an RNA transcript. Optionally, the protein components can be chosen from a broad class of DNA translocation enzymes including DNA and RNA helicases, viral genome packaging motors, and chromatin remodeling ATPases. Certain examples of such protein components are described, e.g., in: Mechanisms for nucleosome movement by ATP-dependent chromatin remodeling complexes. Saha A, Wittmeyer J, Cairns B R. Results Probl Cell Differ. 2006; 41:127-48, Mechanisms of nucleic acid translocases: lessons from structural biology and single-molecule biophysics. Hopfner K P, Michaelis J. Curr Opin Struct Biol. 2007 February; 17(1):87-95. Epub 2006, Structure and mechanism of helicases and nucleic acid translocases. Singleton M R, Dillingham M S, Wigley D B. Annu Rev Biochem. 2007; 76:23-50, Non-hexameric DNA helicases and translocases: mechanisms and regulation. Lohman T M, Tomko E J, Wu C G. Nat Rev Mol Cell Biol. 2008 May; 9(5):391-401.

In a preferred mode of operation, the rate of nucleic acid translocation can be controlled by the concentration of a reactant or cofactor. For example, DNA translocases couple hydrolysis of nucleotide triphosphate cofactors to the translocation of DNA. The E. coli FtsK enzyme can advance the DNA at speed of about 5000 bases per second (at 25° C.) by hydrolyzing ATP. Under conditions of limiting ATP the rate can be modulated to slow the translocation rate for optimal sequence detection. FtsK enzyme can translocate DNA in either direction which can be utilized in such a configuration to facilitate redundant single molecule sequencing to increase consensus accuracy. It is understood by those skilled in the art that similar modes of control of DNA translocation by polymerases and helicases could likewise be affected by the concentration of nucleotide or metal cofactors. Redundant sequencing approaches could also be affected by intrinsic or extrinsic exonuclease activities. (See, e.g., U.S. Pat. No. 7,476,503; and U.S. Ser. No. 12/413,258, filed Mar. 27, 2009, both of which are incorporated herein by reference in their entireties for all purposes.) The kinetics of the enzymes can be altered by mutation or conditions to maximize the likelihood of sequence detection. (See, e.g., U.S. Ser. No. 12/414,191, filed Mar. 30, 2009; and U.S. Ser. No. 12/384,112, filed Mar. 30, 2009), both of which are incorporated herein by reference in their entireties for all purposes.)

The rate of nucleic acid translocation through nanopores under an applied voltage can also be controlled by the binding of proteins, small molecules, and/or the hybridization of complimentary strands (see, e.g., FIG. 11). The nanopore (202) physically occludes the passage of the nucleic acid strand with the bound enzyme, small molecule, or complementary strand (200, 204). The kinetics of nucleic acid translocation can be controlled by the concentration of 200 (cis side) and 204 (trans side). For example, the binding element could be: E. coli SSB, T4 gene32, Tth SSB, Taq SSB, T7 gene 2.5, or any other of the broad class of single-stranded DNA binding proteins, which are known to be involved in almost every aspect of DNA metabolism. Additionally useful are the recombinational enzymes like recA or the eukaryotic proteins Rad51 and Dmc1 because their binding properties can be modulated by the addition of ATP, ADP, and nonhydrolyzable ATP analogs (see, e.g., Structure and Mechanism of *Escherichia coli* RecA ATPase, Charles E. Bell, Molecular Microbiology, Volume 58, Issue 2, Pages 358-366).

In certain embodiments, polymerases are used to modulate the passage of a nucleic acid strand through a nanopore. For example, it has been demonstrated that the passage of DNA through a nanopore structure can be controlled by the binding of Klenow fragment DNA polymerase in the presence of varying concentrations of cognate nucleotide (Specific Nucleotide Binding and Rebinding to Individual DNA Polymerase Complexes Captured on a Nanopore; Nicholas Hurt, Hongyun Wang, Mark Akeson and Kate R. Lieberman; J. Am. Chem. Soc., 2009, 131 (10), pp 3772-3778). Binding events can be individual and stochastic or cooperative (e.g. gene32 polymerization on single-stranded DNA) For example, see: On the thermodynamics and kinetics of the cooperative binding of bacteriophage T4-coded gene 32 (helix destabilizing) protein to nucleic acid lattices. S C Kowalczykowski, N Lonberg, J W Newport, L S Paul, and P H von Hippel; Biophys J. 1980 October; 32(1): 403-418.). In general, conditions that favor binding to the nucleic acid strand will slow translocation of the nucleic acid strand to the other side, and conditions that are less favorable to binding will permit relatively faster translocation. These factors can be modulated advantageously to promote efficient sequence detection, e.g., by allowing the reaction to proceed at a rate that provides for a desirable balance between accuracy and throughput.

One aspect of the invention is the use of processive DNA-binding enzyme to enzymatically regulate the rate of ssDNA tranlocation through the nanopore. For example, λ-exonuclease processively degrades one strand of a dsDNA template in the 5'-3' direction. The single-stranded part would snake through the nanopore, and the excised dNMPs would diffuse away (because the ssDNA would leave no room for them to pass through the nanopore). The rate of ssDNA translocation through the nanopore would now be limited by the rate of k-exonuclease activity, which could be modulated by Mg concentration, buffer conditions, and potential mutagenesis of the enzyme. k-exonuclease is described in Science. 2003 Sep. 26: 301(5641):1914-8.

In some cases we can use a DNA-binding enzyme to act as a plug to the nanopore and regulate ssDNA translocation rate non-enzymatically, For example, Exonuclease I degrades ssDNA. However, one could use an enzymatically inactive Exonuclease I (or e.g. leave Mg out of the solution buffer) that still binds tightly to ssDNA. Again, the unbound ssDNA would snake through the nanopore, whereas the exonuclease bound to the ssDNA would act as a plug and prevent translocation. Applying a strong enough potential can rip the ssDNA from the tightly bound exonuclease, advancing the ssDNA through the nanopore. By applying short pulses of large potential (translocation step) separated by periods of lower potential (allows rebinding of exonuclease), then one can pull the ssDNA through the nanopore in steps, for example one base at a time. The rate and duty cycle of the pulses could be altered to optimize the translocation rate and measurement duration.

For this embodiment, DNA binding proteins other than an exonuclease can be used. For example, a DNA polymerase locked in the closed state (e.g. by having calcium but no magnesium in the solution) may be used. In this case, the dsDNA primer can get peeled off one base at a time as the high potential pulse pulls the ssDNA through the pore.

Alternatively, a histone can be used. 146 base pairs at a time of dsDNA generally wrap around a histone complex like a spool. As above, the histone would act as a stop to the nanopore. High potential pulses would unravel the spool one base at a time. As with the polymerase, one of the two strands in the dsDNA would still have to be peeled off by the nanopore, which only allows ssDNA to pass through.

Once aspect of the present invention is to use a processive polymerase such as Phi29 with a nanopore. The polymerase is applied on the upstream side of the nanopore, as well as the DNA template to be sequenced and primer, if any. dNTPS are added to the solution at a concentration that allows a sufficiently long time between base incorporation events to facilitate accurate readout from the nanopore for each base position. The use of a processive enzyme allows the baseline nanopore signal to be free of disturbance caused by the binding and unbinding of polymerase. Another aspect of the present invention is to use a strand displacing enzyme and to thread the displaced product rather than the template through the nanopore. In this way, the direction of DNA motion is in the same direction as the applied electric force. This allows increased readlength, reduction in buildup of extraneous DNA at the upstream side of the pore as well as other problems. Another aspect of the invention is to use an enzyme with two or more slow steps in the translocation step. This would allow for decreased incidence of events that are too short to be reliably detected. An additional advantage of using the displaced product rather than the template, is that the template can be maintained in a double-stranded state, thus increasing the stability of the template, and allowing for longer readlength.

Figure 12:
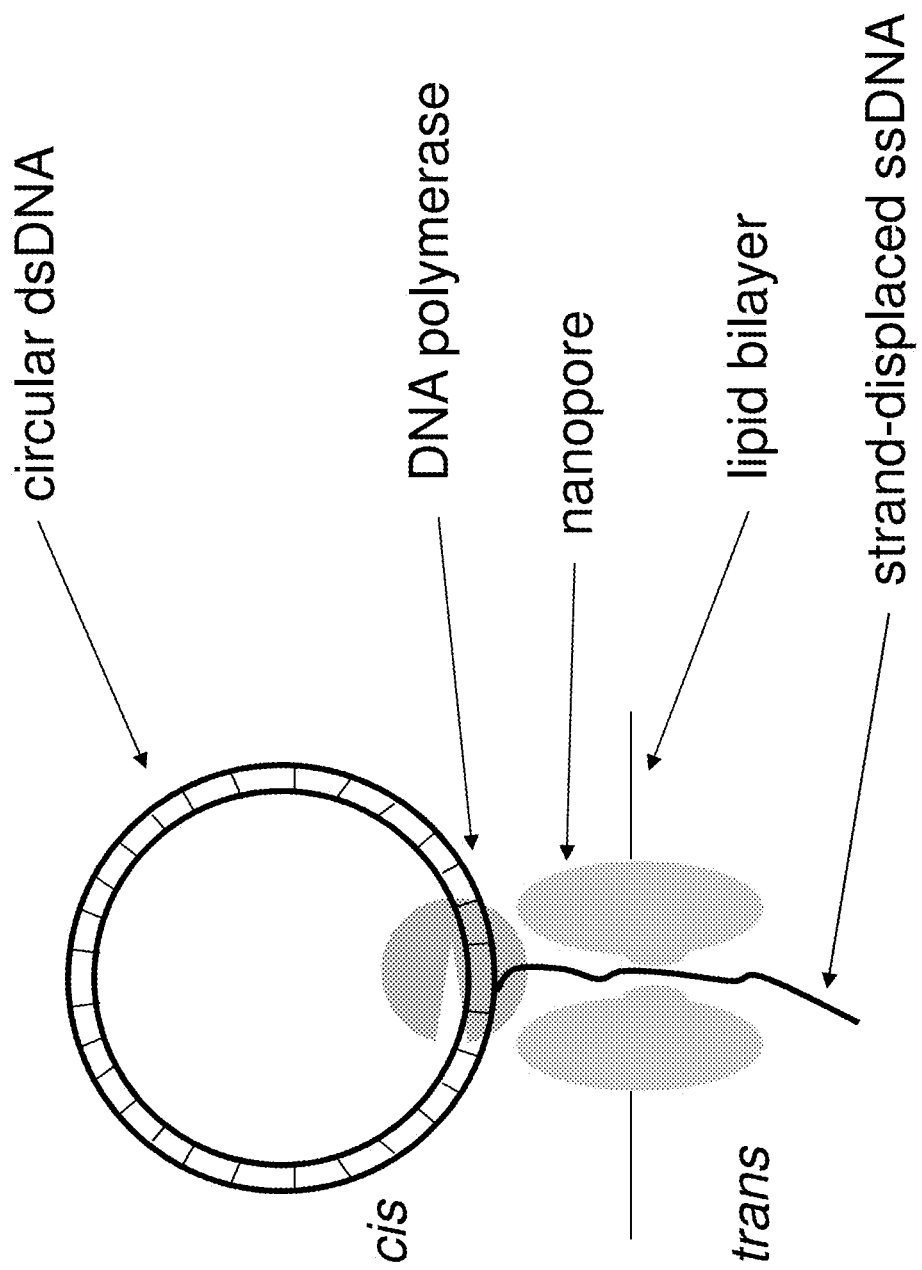
FIG. 12 shows an embodiment for controlling translocation during sequencing in which a DNA polymerase enzyme with strand displacement is used to create a single strand of DNA which is then translocated through the nanopore.

One embodiment for controlling translocation during sequencing is illustrated in FIG. 12. A DNA polymerase enzyme with strand displacement is used to create a single strand of DNA which is then translocated through the nanopore. The circular template will result in a replication of the same sequence multiple times (rolling circle amplification), allowing for higher accuracy. The reagents necessary for performing DNA synthesis, including nucleotides and cofactors are provided on the cis side of the nanopore in order to support synthesis.

Figure 13:
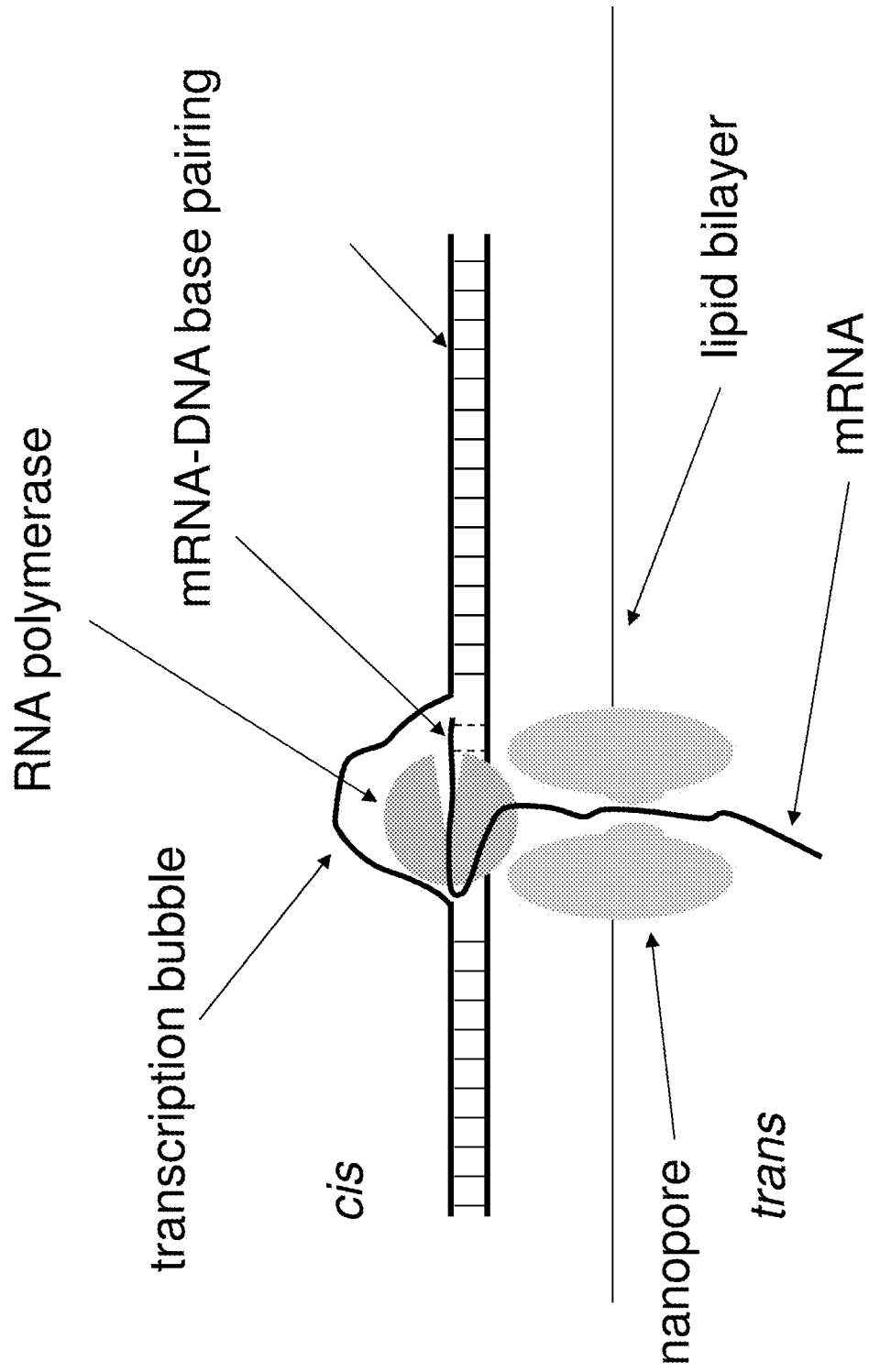
FIG. 13 shows an embodiment for determining sequence information about a template polymer by controlling translocation.

Another embodiment for determining sequence information about a template polymer by controlling translocation is shown in FIG. 13. A DNA dependent RNA polymerase is used to produce an RNA transcript, which is translocated through the channel and sequenced.

Electronic Control of Translocation Rate—Molecular Braking

Figure 14:
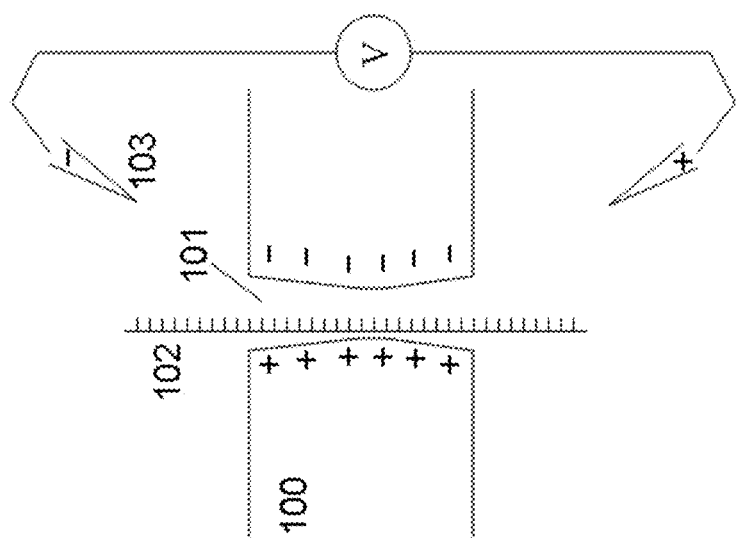
FIG. 14 illustrates electrical control of translocation of a molecule through a nanopore.

One aspect of the invention is the control of translocation by electrical processes. In other embodiments, translocation of a molecule (e.g., a polynucleotide) through a nanopore can be controlled electrically. For example, and with reference to FIG. 14, one skilled in the art will realize that electric fields within the supporting membrane (100) and transverse to the nanopore (101) can be used to manipulate a single-stranded DNA molecule (102) because the DNA backbone phosphates generally carry a net negative charge. In essence, the field attracts DNA toward the positive terminal and pulls the DNA against any physical barrier. Steric interactions (i.e., microscopic friction) with the barrier reduce the kinetic energy of the translocating DNA, initially induced by an additional bulk solution field (103), through conversion to heat. This effect is termed "Molecular Braking," and the nanostructure that is the "Molecular Brake" includes, but is not limited to, the supporting membrane (100), transverse electrodes (which may or may not be the supporting membrane; fabrication discussed below), and the nanopore (101).

Figure 15:
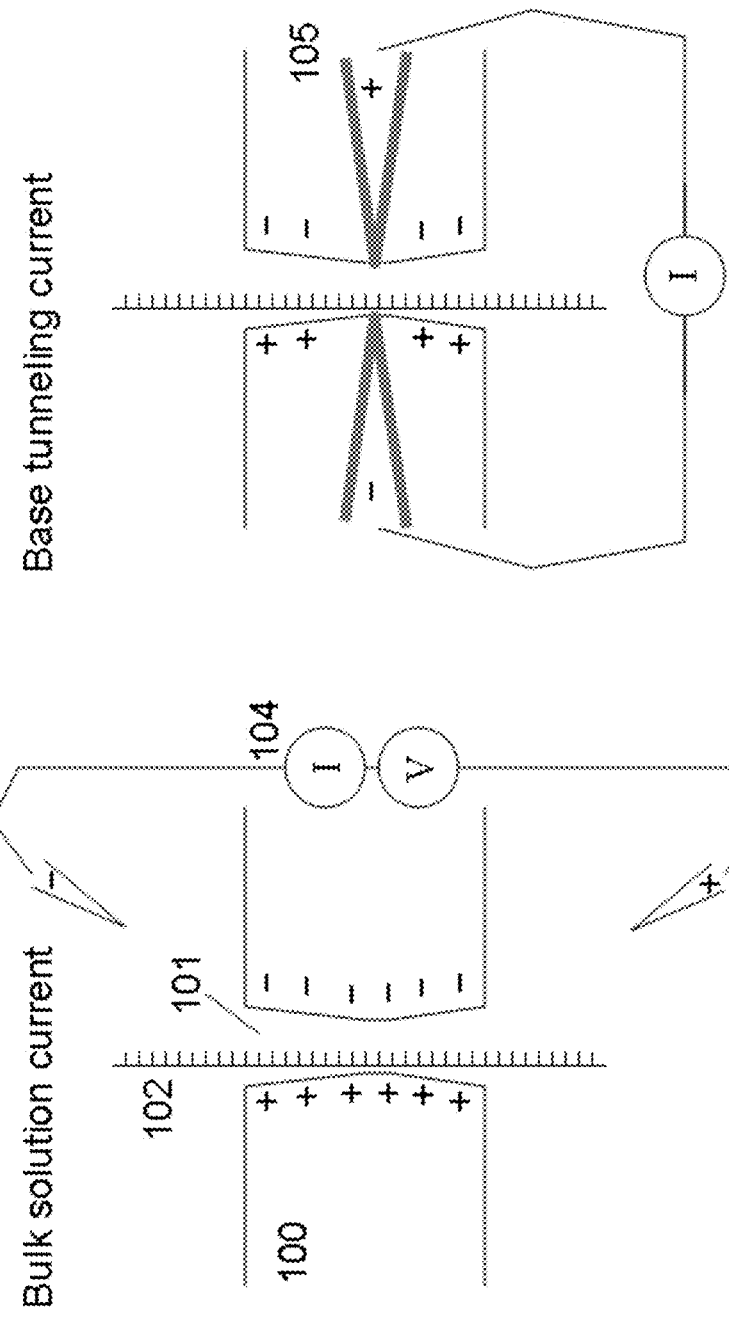
FIGS. 15A and 15B illustrate the use of a molecular brake to control translocation through the membrane.

Optionally, the transverse electric field can be either AC or DC. Optionally, the Molecular Brake can be applied when the functional current readout of the DNA translocation is either through additional bulk solution electrodes (104) or through nanograp detection, i.e., through a tunneling current between electrodes embossed in the supporting membrane (105), as shown in FIGS. 15A and 15B.

Figure 16:
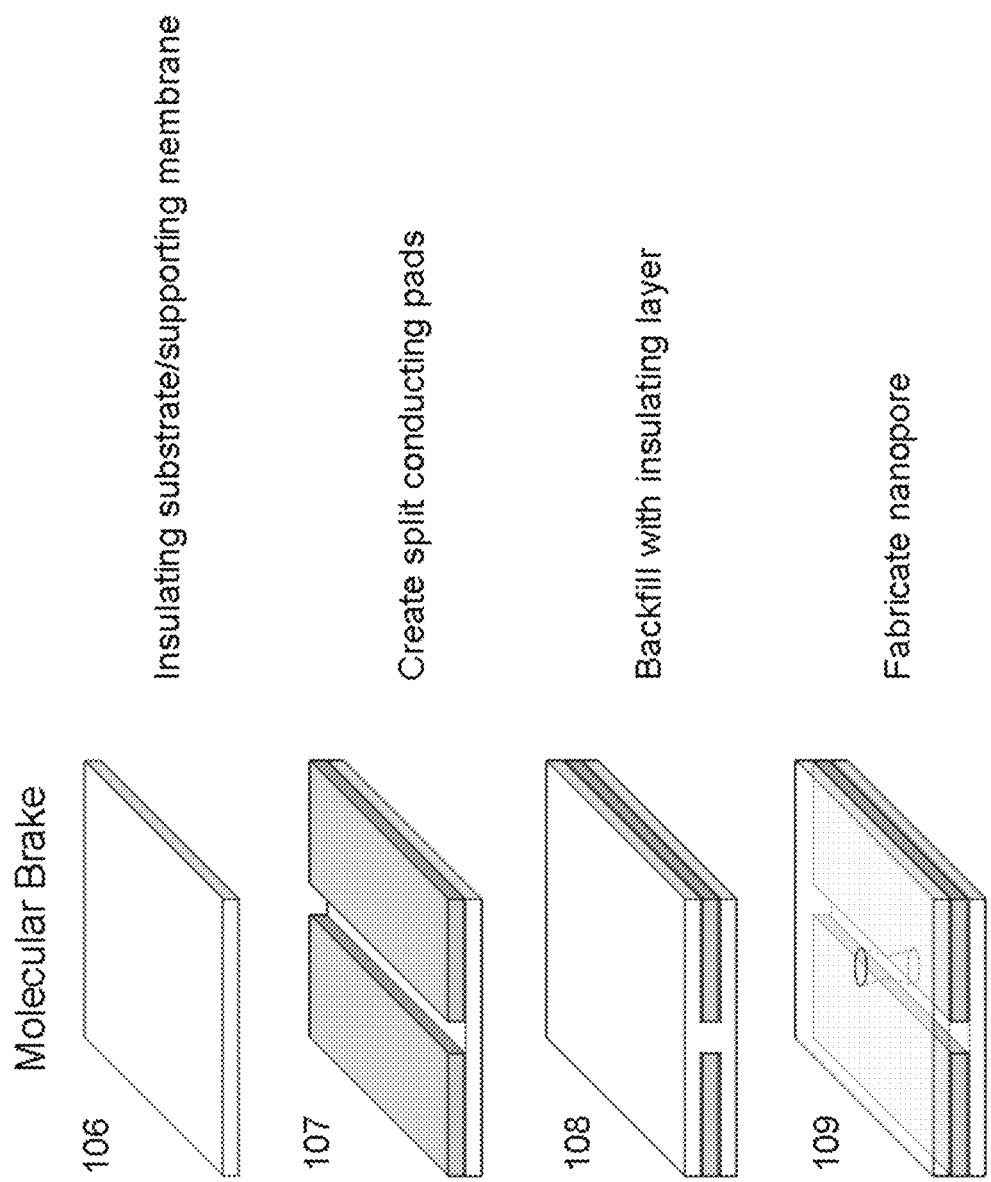
FIG. 16 shows a process for producing a molecular brake.

Several means of fabricating such a Molecular Brake are available to one skilled in the art, e.g., on an insulating substrate (106), growing a thin metal film and dividing into two pads separated by a very thin gap (107; similar to Liang and Chou, Nano Letters, 8:5 1472 (2008)), evaporating on an insulating "cover" (108), and fabricating a nanopore through the channel (109) by, e.g., SEM drilling or transverse electron beam ablation lithography, examples of each of which are shown in FIG. 16.

Figure 17:
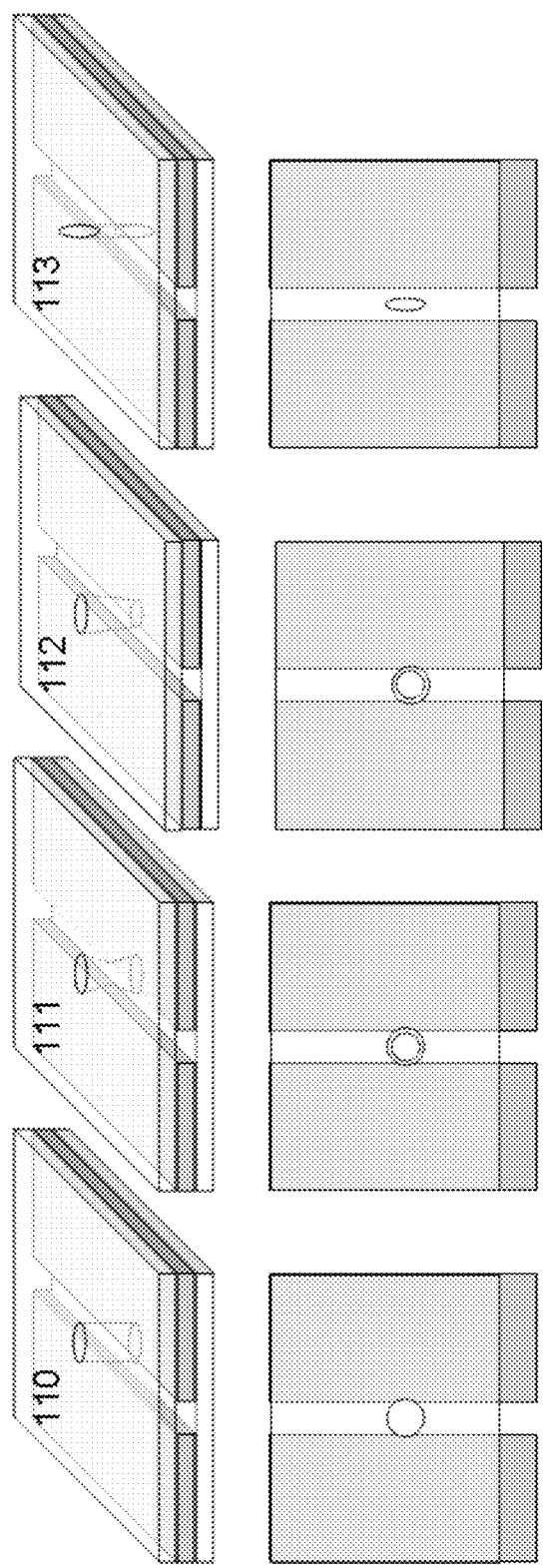
FIG. 17 illustrates nanopores having different profiles.

Optionally, and with reference to FIG. 17, the nanopore can have a cylindrical profile (110), hourglass profile (111), conical profile (112) or an elliptical cylindrical profile (113), and in preferred operation would have a minimal transverse diameter of less than 3 nm and length of less than 500 nm.

Although shown as having straight walls, the walls may also be tapered or otherwise shaped while retaining the overall cylindrical, conical, hourglass, or elliptical cylindrical profile. Further, in certain preferred embodiments the hourglass profile would be used as this profile reduces the steepness of the entropic barrier as DNA enters the pore, and the bulk solution voltage drop from cis to trans occurs over just a few nanometers at the tightest constriction of this pore (see, e.g., Comer et al., Biophys. J. 96:593-608, (2009)). Further, the location within the nanopore at which detection occurs may be positioned at the center of the nanopore, or may be nearer to either the cis or trans end of the nanopore, and is optionally located at a point in the nanopore that is constricted relative to other positions within the nanopore.

Beyond Molecular Brakes, it is possible to use a stack of conducting pads that are electrically addressable to convey the DNA in lock step through the nanopore. Local inhomogeneities in the DNA charge distribution enable this such that even if the conducting layers are thicker than the phosphate backbone spacing, active transport may still be possible, termed the "Molecular Sidewalk." When charge variation is naturally present along the DNA target template, and this is constrained laterally in an alternating potential, e.g., by a nanopore through a stack of differentially-charged plates, then DNA regions will preferentially localize within that potential and may be held against thermal energy. If that periodic potential is translocated from cis to trans, then the DNA that is caught within that potential will be transported in lock-step. Further, should the DNA encounter symmetric energy barriers for moving cis versus trans as the Molecular Sidewalk potential sweeps to trans, the bulk solution voltage will break that symmetry and may induce motion to trans. Shown in FIG. 18 is a DNA molecule (one position marked with an "x" for clarity) being transported down through the pore with alternating fields.

Figure 19:
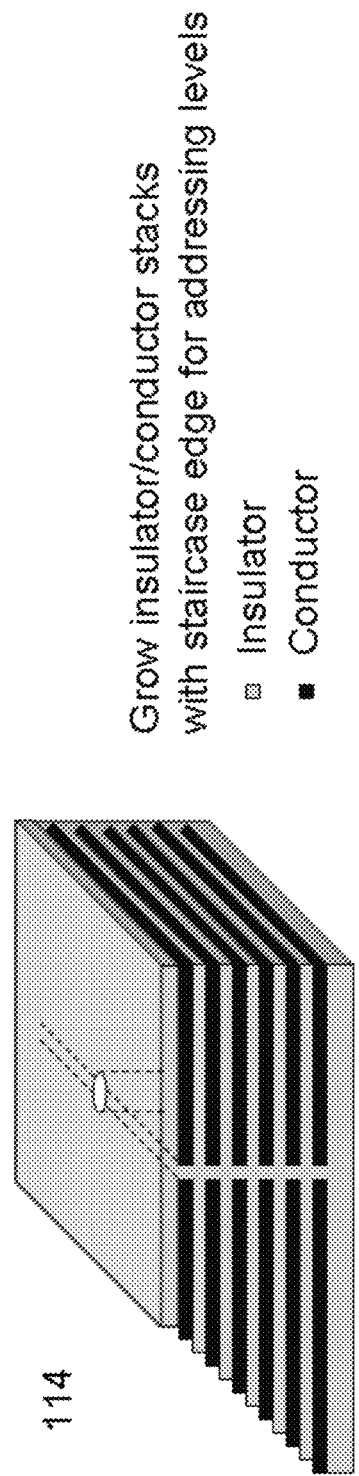
FIG. 19 shows a structure with multiple layers of conducting pads that are electrically isolated and individually addressable.

The function of the Molecular Sidewalk can occur by either aforementioned detection modes. The fabrication architecture of Molecular Brakes can be extended to multiple layers of conducting pads that are electrically isolated and individually addressable. (See, e.g., FIG. 19.)

Optionally, the Molecular Sidewalk may also be combined with braking methods including but not limited to Molecular Braking. In one implementation, a cis-side Molecular Brake is combined with a trans-side Molecular Sidewalk. One skilled in the art realizes that DNA bunching may occur for the Molecular Sidewalk if not carefully implemented, due to, e.g., sequence context variation that causes a given region of the strand to localize to a local potential minimum. This combination may yield entropic and enthalpic stretching of the DNA as the Molecular Sidewalk pulls the DNA through the pore, with the Molecular Break retarding that motion. Optionally, a nanogap detector could be located between the Molecular Brake and Molecular Sidewalk in the supporting membrane, where the DNA may be optimally positioned for detection. Optionally, braking may be achieved with DNA binding moieties including but not limited to proteinaceous compounds (e.g., RecA or Gene 32) or short nucleic acid polymers (i.e., random or nonrandom sequences of various lengths that anneal to the target template and must be dissociated from said template by force as translocation occurs), as described above.

In certain preferred embodiments, the per base translocation rate through all devices or combinations of devices would be between 100 Hz and 100 MHz.

Electronic Control of Translocation Rate—Molecular Iris

Even with the ability to differentiate the distinct current-based signals ("signatures") produced by passage of the four different bases through the nanopore, single-molecule sequencing with nanopores is fundamentally challenged by the ability to detect and characterize homopolymer regions of a target template. The primary reason for this is due to the identical signals produced for subsequent positions of the same base, and difficulties quantifying how many of the same signals are being detected. In certain embodiments of the instant invention, an approach, termed the "Molecular Iris," is used to increase system resolution by making base-wise translocation through the nanopore more clock-like, thereby promoting individually detectable current signatures for every base translocation through the nanopore.

This approach is analogous to a molecular-scale ratchet and pawl system where the pawl tension is very stiff relative the energy that is moving the ratchet (e.g., high energetic barrier to move forward; much, much higher barrier to move backward). Without being bound by any particular theory of operation, the general implication is that a given position of the ratchet will be sampled on a longer time scale than the overall timescale associated with translocation. For the nanopore system, a polynucleotide passes through the nanopore and represents the ratchet with the bases as teeth. The pawl in this system is an element on the pore wall that interacts with the bases, e.g., intercalates between the bases. Interaction of the pawl with a given base causes translocation to effectively pause at that base, allowing the current signature of the base to be accurately and individually detected. As such, each base position can be sampled for a higher duty cycle relative overall base-to-base translocation due to the presence of the pawl.

Figure 20:
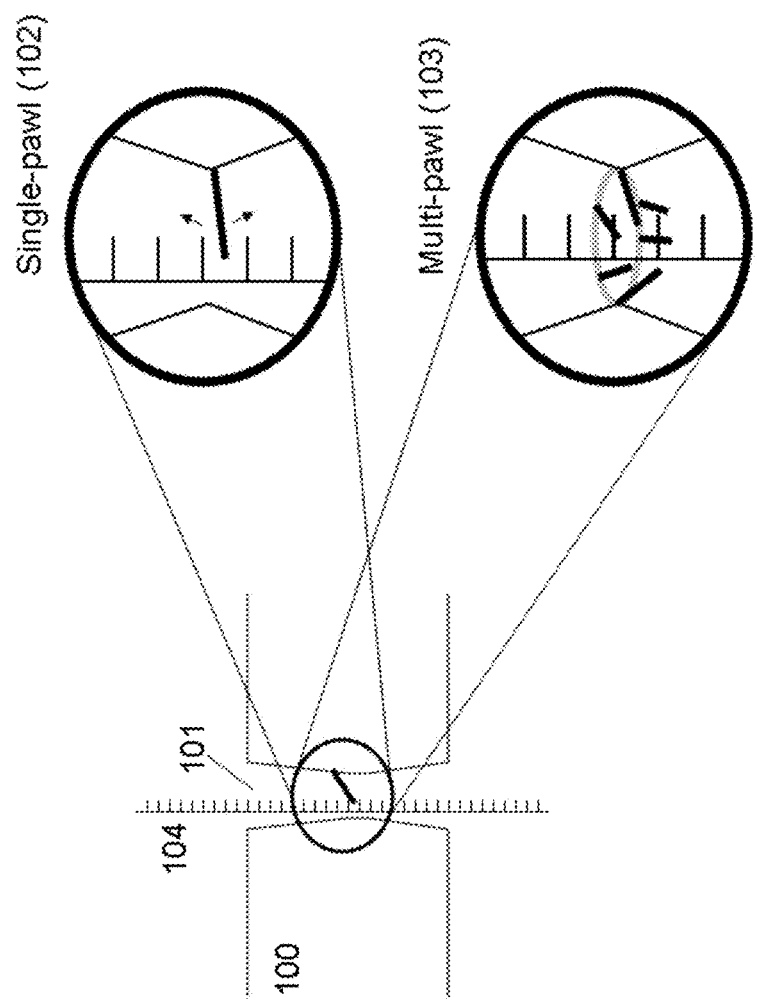
FIG. 20 illustrates a molecular pawl.

An embodiment of this aspect of invention is shown in FIG. 20. A key feature of the membrane (100) supported nanopore (101) system is the pawl (102), or set of pawls (103), that are inside the nanopore barrel and interact with single-stranded polynucleotide (e.g., DNA) (104). Because these device elements restrict motion through the barrel by partially closing it off, we term this system the "Molecular Iris."

Figure 21:
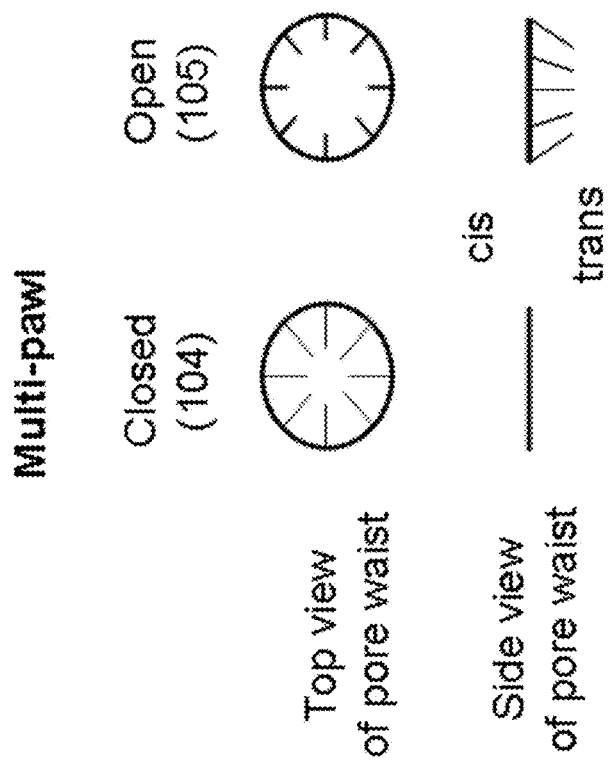
FIG. 21 shows a multi-pawl aperture.

The multi-pawl case is illustrated in FIG. 21. For the multi-pawl case, the closed (104) state is generally the state at which the nanopore barrel is most restricted and the open (105) state is generally the state at which the nanopore barrel is least restricted. In certain embodiments, the closed configuration has all pawls directed toward the molecule passing through the nanopore (e.g., pointed inward), and the open configuration has all pawls directed away from the molecule (e.g., pointed upward or downward, or otherwise retracted away from the molecule.) Optionally, the pawls may move in concert or independently. Various other embodiments of open and closed configurations will be clear to those of ordinary skill in the art.

Pawls may include but are not limited to nucleic acids or amino acids, either in side chain or polymer forms, small-molecules such as ethylene glycol or solid state materials with modulated physical properties (e.g., piezoelectric material that expands/contracts in an external field). Pawls may be embedded in either a synthetic nanopore, biological nanopore, or a chimera of both.

One skilled in the art will recognize that biological nanopores (e.g., multi-subunit nanopores, including but not limited to naturally occurring alpha hemolysin and MspA) or subunit concatemers (in which the DNA monomer code is copied and concatenated, resulting in a single polypeptide for the entire protein) can be mutated for attachment of pawls. Such methods include mutagenesis to add or substitute extra residues that would interact with the DNA (including but not limited to polar residue phenylalanine, tryptophan and histine, or charged residues aspartate, glutamate, lysine, arginine, or histidine), residue mutation to cysteine for disulfide linking chemistry to proteinaceous or solid state pawls, or other methods. One particularly useful approach is to incorporate unnatural amino acids into the protein nanopore order to produce the molecular iris. In this way, the desired chemical properties can be engineered into the protein, e.g. in a repeated subunit, without having to perform reactions on the protein after it is formed. Methods of incorporating non-natural amino acids are well known in the art. Fusion proteins can also be used to produce such structures.

There are several advantages of including a pawl or pawl complex in a nanopore over standard nanopore sequencing. (1) A pawl that interacts strongly with each base may confer extra sensitivity and specificity to the current flowing around that base, including but not limited to hydrophobic ring stacking (e.g., between the base and a tryptophan pawl) or steric effects (e.g., between the base and a proline). (2) A multi-pawl complex means that several elements must move to allow DNA translocation, which is likely to render transport more uniform in speed (i.e., more clock-like), though one skilled in the art will realize that overall speed can additionally or alternatively be controlled by pore size and driving voltage. (3) Because the pawl must move to step from one base to the next (i.e., the Molecular Iris goes from a closed state to open and back to closed for a single translocation), a significant current may be discharged even during homopolymer sequencing, which can be keyed upon for base calling of sequential nucleotides having the same base composition.

Multiple Stage Nanopore Sequencing

One aspect of the invention involves using multi-staged nanopores for obtaining polymer sequencing information. In nanopore DNA sequencing, base calling is performed by detecting the current blocking events as ssDNA or single dNMPs translocate through the pore (often either a modified alpha-hemolysin protein pore or a solid-state pore). See e.g. Nature Biotechnology, 26 (10):1146-1153, (2008). A combination of the amplitude and the duration of the current block is used to distinguish the four nucleotides from one another. However, the amplitude of current blockage for each nucleotide has a Gaussian distribution, and the distributions from each of the four nucleotides can overlap significantly (more or less so depending on the solution conditions), increasing the likelihood of miscall errors. A means of performing consensus calling in order to reduce this error source is described below.

If one nanopore embedded in a membrane that separates two compartments is considered one stage, then by having more than one membrane, we can concatenate multiple stages. For example, once the analyte (e.g. ssDNA or dNMP) has passed through the first stage nanopore, it could then pass directly through a second nanopore, or a second stage of measurement. If the current blockage through each stage is statistically independent (e.g. noise is dominated by random diffusion and the channels are narrow), then one can compare the two reads and perform consensus base calling based on the two measurements. The multistage nanopore devices of the invention can have 2, 3, 4, 5 or more stages. The number of stages can be generalized to N stages (N independent sets of nanopores) to further improve base calling accuracy to the required level.

In one embodiment, each stage's electrodes are not shared. Thus, for N stages, there would be a total of 2N electrodes (one above and another below each stage).

Figure 22:
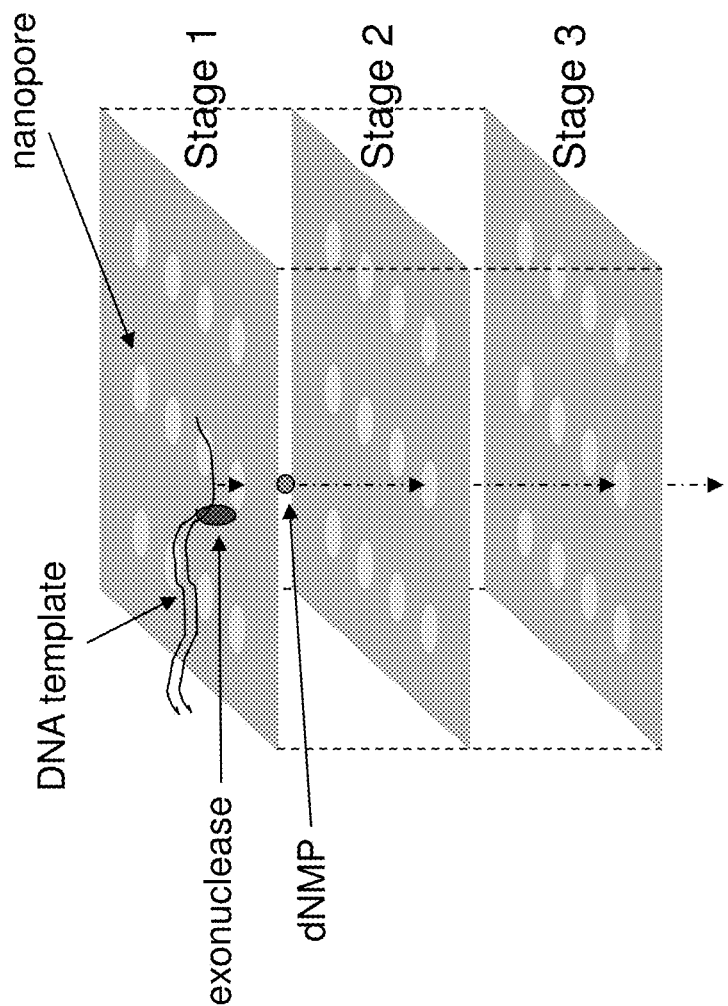
FIG. 22 shows a structure for multiple stage nanopore sequencing.

In another embodiment, adjacent stages share an electrode (e.g. Stage 1 has an electrode on top, and then its bottom electrode serves as the top electrode for Stage 2, which would also have its own bottom electrode). Thus, for N stages there would be a total of N+1 electrodes. An example three-stage system is shown in FIG. 22 (electrodes are not shown).

In one embodiment, the sequencing strategy involves attaching an exonuclease to the nanopore, cleaving dNMPs from dsDNA, and detecting the passage of these dNMPs through the nanopore, then for the multistage nanopore device described herein would only have an exonuclease attached to the first stage's nanopores, but would obtain multiple opportunities to measure the monomers.

Another advantage of this technique is that it can reduce the number of missed pulses, since each nucleotide could be directed to pass through a pore several times and thus have several opportunities to be measured.

This multi stage devices and methods of the invention could be used with solid-state nanopores, protein nanopores, and hybrid protein/solid-state nanopores. Furthermore, a similar technique could be used with a tunneling current measurement scheme.

Each stage can comprise multiple nanopores, e.g. each state can be a layer of nanopores, each with 2-10-100, 1000 or more nanopores. The number of pores in the various layers can be coupled such that flow continues through only one set of pores. In other cases, the pores can be decoupled. In some cases, current measurement made at each stage, in other cases, measurements made only after multiple stages.

One embodiment comprises a linked complex of two or more nanopores in series—and one electrical measurement system. Distribution of current blockage duration will be the convolution of the exponential distributions of those for each individual nanopore. In some embodiments, each of the N nanopores could be different—e.g. more effective at distinguishing particular bases. These structures can be created, for example, by genetically engineering the multiple nanopores as fusion proteins. Alternatively, the individual nanopores can be linked, e.g. hydrophobically. In some cases "terminating" nanopores can be added to control nanopore concatenation. In some cases, specific top and bottom terminating nanopores can be used to control nanopore concatenation.

Use of Tunneling Current and Multiple Stages

One aspect of the invention is the use of tunneling current and multi-staged nanopores. It has been suggested that the ability to discriminate between bases can be enhanced by using a tunneling current technique and by forming base-specific hydrogen bonds between the nucleotide being detecting and a chemically modified pore or tunneling current probe. This has been described for use in conjunction with a transverse tunneling current measurement. For example, the probe could be functionalized with one of four nucleotides (e.g. cytosine), and then the tunneling current would be greatly enhanced when the complementary nucleotide (e.g. guanine) passes through the pore. See references Proc. Natl. Acad. Sci. USA 103, 10-14 (2006); Nano Lett. 7, 3854-3858 (2007).

Figures 23A, 23B:
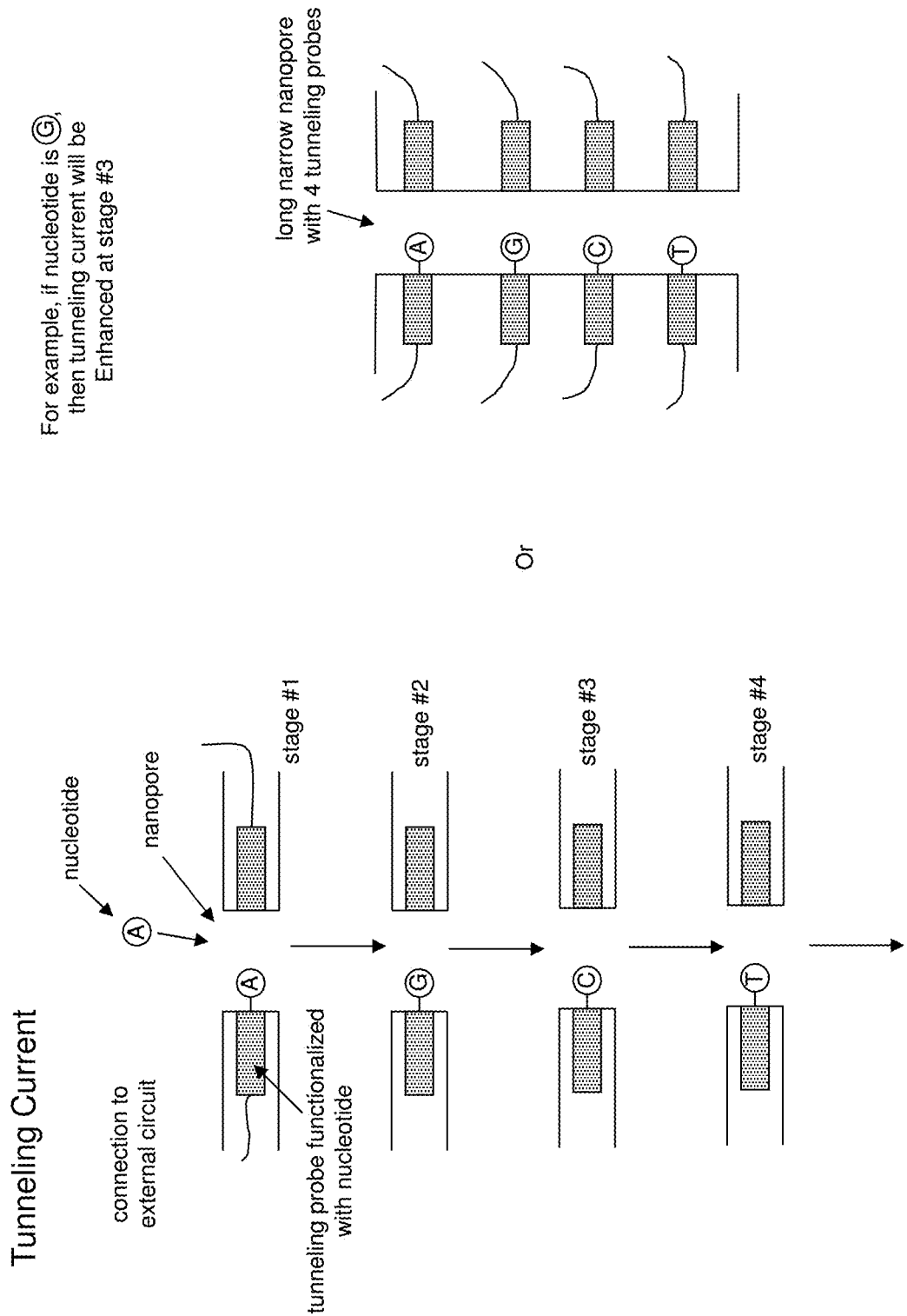
FIG. 23A shows a schematic drawing of a multi-staged tunneling current measurement system.
FIG. 23B shows an alternative multi-stage tunneling embodiment having one channel with several transverse tunneling measurement stages.

A potential disadvantage of this technique, however, is that it would require four readers (each functionalized with a distinct nucleotide) sequencing duplicate strands in synchrony, a difficult task to achieve Nature Biotechnology, 26 (10):1146-1153, (2008). We have discovered that a multistage nanopore system of the current invention can address this issue. Instead of four readers sequence four duplicate strands, the device of the current invention would have multiple stages of readers, for example, four stages of readers wherein each is functionalized with a distinct nucleotide for sequencing the same strand. FIG. 23(a) shows a schematic drawing of a multi-staged tunneling current measurement system. In this case, the multi-staged tunneling current nanopore system consists of all solid-state nanopores or of hybrid protein/solid state nanopores.

FIG. 23(b) shows an alternative multi-stage tunneling embodiment having one channel with several transverse tunneling measurement stages. For example, the device can comprise, one long solid-state nanopore that contains 4 tunneling current probes along its length, each functionalized with a different nucleotide.

Use of Tunneling Current

One aspect of the invention involves the measurement of tunneling current to determine sequence information using a multiplex solid state array of nanopores. Given typical drive voltages of a few hundred mV, typical ionic currents flowing through a <3 nm diameter nanopore are in the picoamp or tens of picoamp range. Using state-of-the-art detectors, the detection of such small currents can generally be accomplished with ~kHz bandwidths. For example, events (e.g. nucleotides traversing the nanopore for sequencing applications) can be detected faithfully where their duration is on the order of milliseconds.

Since nucleotides under a 120 mV potential can traverse an alpha-hemolysin nanopore in microseconds, Nature Biotechnology, 26 (10):1146-1153, (2008), one solution has been to insert an adaptor molecule into the alpha-hemolysin nanopore in order to slow down the nucleotide traversal, JACS, 128:1705-1710 (2006). Another solution suggested in the literature has been to instead measure the transverse tunneling current between 1 nm diameter probes situation across a nanopore Nano Lett. 5, 421-424 (2005); Phys. Rev. E 74, 011919 (2006); J. Chem. Phys. 128, 041103 (2008); Nano Lett. 6, 779-782 (2006); Biophys. J. 91, L04-L06 (2006). The advantage of this technique is that tunneling currents can be in the nanoamp range Nano Lett. 7, 3854-3858 (2007), which would enable state-of-the art detectors to measure the microsecond timescale events, such as the translocation of nucleotides through unmodified pores.

Descriptions of tunneling current nanopore systems in the literature generally describe solid-state nanopores, since these can be fabricated along with the nano-electronic components required for tunneling current measurements. Fabricated nanopores, however, can also have a large variation in size, shape, orientation, surface chemistry, etc. between individual nanopores. This has been noted in a review article as a challenge for tunneling current nanopore sequencing, since the tunneling current is very sensitive to orientations of and distances between the electrodes and the nucleotides to be detected Nature Biotechnology, 26 (10): 1146-1153, (2008). One literature proposal is to use carbon nanotubes as a nanopore, as carbon nanotubes have a reproducible size/shape and bind nucleotides in a specific manner Nano Lett. 7, 1191-1194 (2007).

One aspect of the invention comprises creating a hybrid protein/solid-state nanopore for tunneling current nanopore sequencing. The use of protein nanopores, such as alpha-hemolysin, for DNA sequencing has been well documented in the literature JACS, 128:1705-1710 (2006). A great advantage of protein nanopores is that each nanopore is very similar to every other nanopores, yielding an homogeneity in nucleotide orientation/position between each event in each different nanopore. Furthermore, protein nanopores can readily be mutated or hybridized with a linker molecule in order to enhance many properties of the nanopore sequencing system (e.g. increase the nucleotide residence time within the pore, or enhance discrimination between nucleotides). Tunneling current measurements with standard protein nanopore sequencing systems are impossible, though, because protein nanopore are generally embedded in a lipid bilayer JACS, 128:1705-1710 (2006). In the current invention, the surface functionalized solid-state scaffolding in which the protein nanopore is embedded enables integration with tunneling current electronics. The use of tunneling current can be particularly useful when combined with the multistage nanopore designs described above.

Sequencing Using Combined Polymerase/Exonuclease Activity

One aspect the invention utilizes a polymerase/exonuclease pair to push then pull back a DNA strand in the nanopore. In some cases, two separate enzymes can be used, in other cases, the enzyme activities can be in a single enzyme. For instance, in the same enzyme such as Phi29 DNA polymerase. One method for carrying out the invention comprises: 1) adding nucleotides and making use of the polymerization process to push/pull the dna through the nanopore for detection, 2) Removing nucleotides through a wash step, allowing exonuclease activity to kick in and push/pull the dna in the opposite direction of the polymerase activity, 3) Repeating step 1 and cycling. Adjusting the relative rates rate of exonuclease or polymerase speed can be achieved through mutations such as those described herein for polymerases. The relative rates can also be controlled by reaction conditions, such as by controlling the concentration of the nucleotides in solution available for the polymerase. At high nucleotide concentrations, the polymerase will proceed relatively rapidly, and at low nucleotide concentrations the polymerase will proceed more slowly. In addition, if the desire is to read a cleaved moiety, it has been suggested to use an exonuclease to cleave off a base, which then passes through the pore and detected. The invention disclosed here uses a polymerase/exonuclease pair to first polymerize, and use a modified cleaved phosphate group as the detection moiety. Then, after one or more bases, activate exonuclease activity and detect the cleaved base. This allows not only the ability to perform multiple reads on the same strand of DNA, but allows different detection moieties. This method of incorporating both polymerase and exonuclease activity can improve overall sequencing accuracy.

Nanopore-in-Well

One aspect of the invention comprises placing the nanopore within a well structure. Single-molecule nanopore DNA sequencing schemes have been described in which a nanopore is embedded in a flat or nearly flat membrane. An exonuclease is fixed adjacent to the nanopore. As the exonuclease chews up double-stranded DNA, dNMPs are released. A voltage applied across the membrane pulls the released dNMPs through the nanopore, where they are detected and differentiated from one another using current blockage amplitudes, nanopore residence times, or other metrics. See Clark et al., Nature Nanotechnology 4(4), 265-270 (2009).

A problem with this approach is that there is a probability that the dNMP will diffuse away into the bulk solution before the applied voltage can pull it through the nanopore. This situation would lead to a missed base call if the next dNMP to be released by the exonuclease is pulled through the nanopore before the diffusing dNMP makes its way back to the nanopore opening. Furthermore, this dNMP might later diffuse back to the nanopore opening or into a different nanopore's opening (in the case of parallel nanopore sequencing), leading to a false-positive base call.

One aspect of the invention is a structure in which the nanopore is held in a well structure rather than on a relatively flat plane in order to reduce the likelihood that, upon release by an exonuclease, a dNMP will diffuse into the bulk solution. Thus, this aspect of the invention can increase the fidelity with which a dNMP is pulled through the nanopore immediately upon release by the exonuclease. In this invention, the nanopore is depressed within a well (see FIG. 24(b)). The well decreases the probability of the dNMP diffusing into bulk solution in two ways.

While not to be bound by theory, we believe that using the well structures of the invention improve accuracy both by entropy and by enthalpy. Through entropy: on the flat membrane, if the dNMP diffuses first in the z-direction then it will go directly into the nanopore. It will stay in the nanopore despite a subsequent diffusion of e.g. 100 units in the x- or y-direction. However, if it first diffuses in the x- or y-direction by e.g. 100 units, then it has already diffused away from the nanopore opening, and it will not enter the nanopore upon a subsequent z-direction diffusion event. This asymmetry may delay the dNMP from passing through the nanopore before the next dNMP does so. However, if the nanopore is depressed in a well, the asymmetry is not as severe. If the dNMP first diffuses in the x- or y-direction by e.g. 100 units, it may bounce of the wall of the well and end up positioned over the nanopore opening. A subsequent diffusion event in the z-direction would result in the dNMP passing through the nanopore and being detected.

Figures 24A, 24B:
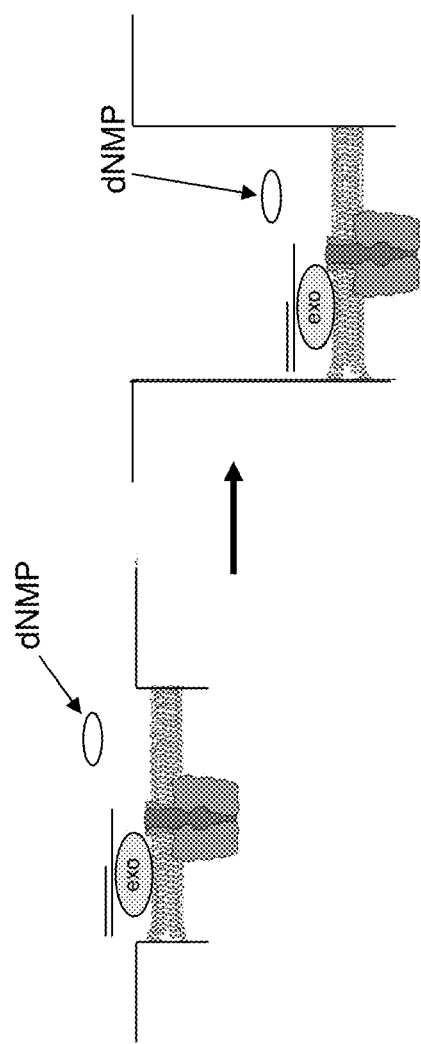
FIGS. 24A and 24B illustrate a nanopore is depressed within a well.

Through enthalpy: in the case of the flat membrane, the current density "field" lines fan out in a roughly spherical shape, and the density decreases rapidly as the radial distance from the nanopore center increases. Thus, if the dNMP does diffuse away from the nanopore center and against the energy barrier (through thermal fluctuations depending on the thermal Boltzmann factor kBT) by e.g. 100 units, the energy barrier for the particle to move e.g. another 100 units away from the nanopore is lower, and thus it is even easier for it to diffuse even further away. On the other hand, the current density "field" lines within the well are parallel and maintain the same density until the opening of the well is reached, upon which the lines fan out as before. Within the well, the energy barrier for the particle diffusing e.g. 100 units away from the nanopore is not decreasing as the dNMP gets further and further away (but remains inside the well). Thus, within the well, the particle is less likely to diffuse against the energy barrier due to the applied voltage. FIG. 24(b) illustrates a nanopore in a well structure of the invention. In some embodiments, the height to width of the well is about 1 to 1, about 2 to 1, about 3 to 1, about 5 to 1, about 10 to 1, or more than 10 to 1. In some cases the average height and average width is used. The shape of the well structure can be any suitable shape.

One aspect of the invention comprises the use of a magnetic or paramagnetic label onto the polymer to be sequenced, and using a magnetic field to control the translocation of the polymer through the nanopore. In some cases, the magnetic field will be used in conjunction with drive electrodes. In some cases the magnetic field alone can be used to translocate the polymer. Where only the magnetic field is used to translocate, the system can be simplified because no drive electronics are needed, and the currents required for electronically driving the molecules through the pore are not required.

AC Field Dielectrophoresis

One aspect of the invention is the incorporation of AC dielectrophoresis to assist in transporting the molecules of interest through a nanopore. In some sequencing methods, e.g. utilizing exonucleases as described above, there is a probability that a molecule of interest, such as a dNMP will diffuse away into the bulk solution before the applied voltage can pull it through the nanopore. This situation would lead to a missed base call if the next dNMP to be released by the exonuclease is pulled through the nanopore before the diffusing dNMP makes its way back to the nanopore opening. Furthermore, this dNMP might later diffuse back to the nanopore opening or into a different nanopore's opening (in the case of parallel nanopore sequencing), leading to a false-positive base call.

It is known that DNA can be moved or sorted by dielectrophoresis (the gradient of an electric field, such as that through a nanopore under an applied potential, can apply a force to a polarizable material). See Electrophoresis, 23 (16): 2658-2666. Furthermore, there are peaks in the frequency spectrum at which DNA is most highly polarizable and at which dielectrophoresis is most effect. The same effect will likely apply to individual dNMPs. By applying a potential with a DC offset (for the electrophoretic component of pulling a charged particle through the nanopore) and an AC component at a peak in the dielectrophoretic frequency spectrum of an individual nucleotide, the movement of a nucleotide through the nanopore is enhanced.

This technique would reduce errors in nanopore sequencing by enhancing the probability that a dNMP gets pulled directly through the nanopore after excision by the exonuclease. This technique may also be applied to the method of nanopore sequencing in which a ssDNA is pulled through the pore, and it would enhance the probability that the ssDNA would be pulled successfully all the way through the pore.

In this embodiment of the invention, the nanopore sequencing takes place without any DC component of the applied electric field. This is advantageous because DC drive can result in either electrolysis of water or the dissolution of metal ions at the drive electrodes, both of which stand to degrade the performance of the system unless the drive electrodes are far from the detection center. In this embodiment, the motive force to preferentially drive the DNA in one direction is dielectrophoresis. A local zone of constricted electric fields is established and because of the large dipole moment of DNA over a wide range of applied frequencies, the DNA molecules feels a net force attractive towards the high-AC-electric-field region of the fluid. This high AC electric field region can be implemented either through the presence of an electrode or through a constriction in the fluid path that obliges the AC electric field lines to converge due to the equation of continuity. See Chou et al. Biophysical Journal, 83, 2179-2179 (2002).

This zone of high AC field is positioned proximal to the detection nanopore such that a DNA molecule traversing the nanopore is likely to have one end fall into the potential well of the high AC field region. When this happens, there will then be a net force causing the molecule thread through the nanopore at a constant rate, Turner S W, Cabodi M, Craighead H G, Phys Rev Lett. 2002 Mar. 25; 88(12), thus allowing readout of the DNA molecule along its length. To initially load the molecules, a DC drive force is required, however it need only be for a duration long enough to thread the molecule. For this purpose a loading pulse is applied for a duration long enough to cause a nearby DNA molecule to thread the nanopore, but not long enough to exhaust the non-electrolytic (and non-dissolving) capacity of the nearby electrode. This force would bring the molecule into the capture region of the dielectricphoretic trap, at which point the AC field is applied and the DC charge displacement can be slowly reversed at a rate that does not overwhelm the dielectrophoretic trap. In this way the net charge on the electrode is returned to neutral without unthreading the molecule. The sensing of the nanopore conductance is performed by measuring the current voltage relationship in the AC regime.

Another aspect of the invention is methods to measure nanopore conductance during a changing electric field environment without losing fidelity. In some operating regimes, the applied frequency must be low compared with the base transit time. For example at some ionic strengths, DNA is known to have a large dipole moment at 400 Hz, which is high enough to avoid electrolysis for many practical electrode designs, but is much slower than the base transit time, which means that AC techniques for measuring the effect of one base on the conductance cannot be used. To overcome this, the measurement is performed in a quasi-DC mode in which the instantaneous field is known because of the predictable dependence of the AC field with time.

In another embodiment the instantaneous drive voltage is measured to allow explicit comparison of the current with the instantaneous voltage. In this mode, groups of bases are read in a group and then re-read in the opposite direction. At the points in time when the instantaneous field is low (near the turn-around times) the system loses resolution on the bases, potentially creating zones of confusion. Thus, one aspect of the invention is a selection of an amplitude an frequency that arrange it so that the zones of confusion resulting from field reversal do not coincide on the DNA sequence to create blackouts of information, but rather each subsequent thrust places a zone of confusion in a region that has been unambiguously covered by a prior thrust or will be covered by a future thrust. It is an aspect of the invention that much of the sequence will be covered more than once, allowing for error correction on the sequence even from a single molecule. This aspect of the invention can be appreciated also using a combination of DC and AC fields.

Field Modulation—Noise Reduction

In one aspect of the invention, the electric field across the pore is modulated at a specific frequency or set of frequencies, and the measurement electronics are tuned to be sensitive to signals corresponding to the modulation frequency or frequencies. The modulation frequency will generally higher than the frequency at which the measured events are occurring. In some cases the modulation frequency is 5 times, 10 times, 100 times, or 1000 times the frequency at which the monomers are being detected through the pores. In some cases, a frequency modulation on top of the driving field e.g. at a frequency 10× or greater than the applied field is provided. By coupling the detection frequency to a perturbation frequency in this manner, higher sensitivity can be achieved by filtering out unwanted current fluctuations.

Polymerase in Microchannel

One aspect of the invention comprises measuring sequence information about a nucleic acid polymer by incorporating a polymerase enzyme within a channel. For the purposes of the devices and methods described above, the channel comprising the polymerase can be seen to act as a nanometer scale aperture. The requirements of the channel for this embodiment can be different than that for other embodiments described herein. Instead of using a very narrow and short nanopore (on the order of a few nm in diameter and length), we use a nanochannel that can be longer and can be a few nm to tens or hundreds of nanometers in diameter.

In one embodiment, a DNA polymerase-DNA template construct is placed inside the nanochannel. Nucleotides in solution are labeled on their terminal phosphates with any type of label (a few nm to hundreds of nm in diameter) that will cause a detectable change in current flow within the nanochannel (e.g. metal nanoparticles, dielectric nanoparticles, highly charged nanoparticles or biomolecules, large polymers or dendrimers, etc.). A voltage is applied across the axial length of the nanochannel, and the current is measured. When the polymerase incorporates the labeled nucleotide into the growing DNA strand, the current will either increase or decrease in a detectable way for the duration of incorporation (several milliseconds-hundreds of milliseconds). This signal can be distinguished from diffusion of labeled nucleotides into and out of the nanochannel because such events will be much shorter in duration (tens to hundreds of microseconds). In some embodiments, after incorporation, the polymerase cleaves and releases the label from the nucleotide with the cleavage and release of the phosphate.

In addition, the impact on conductivity of a transiently immobilized label can be made to be different to the conductivity change brought about by the presence of a freely diffusing (and drifting) label. In some embodiments of the invention, labels are chosen whose conductivity, when mobile, is matched with the conductivity of the surrounding medium, but which when immobilized can cause either an increase or decrease in the conductivity of the channel, depending on the buffer conditions, the molecular volume, the permeability of the label molecule structure, and other parameters. In this way, the freely diffusing molecules are invisible in the conductivity signal, because they participate in electrical conduction to the same degree as the surrounding medium. In other embodiments, the labels are chosen so that freely diffusing labels induce an increase while an immobilized label causes a decrease in conductivity. In other embodiments the free labels decrease conductivity while the bound labels increase it. By providing an opposite sign of the influence it is possible to differentiate free from bound label while being able to see both. In other embodiments, the labels produce a different impact on conductivity before and after they have been disconnected from their analyte molecule. In this mode it is possible to visualize all three phases of the cycle: diffusive entry into the channel, binding in the molecule, and then release of the label after nucleotidyl transfer. In this way, productive vs. unproductive binding can be distinguished. In some embodiments, the connected label is invisible by conductivity matching, while the cleaved label is visible. In another embodiment, the free label is detectable while the cleaved label is invisible due to conductivity matching.

The detection of events for this aspect of the invention can be inherently different from other nanopore sequencing methods, because the detected signal is providing information about the time in which a nucleotides unit is bound within the active site of an enzyme.

The diffusive mobility of a free label can be different than that of a label still attached to a nucleotide. Since this technique uses electrical detection, the sample rates of measurement can be tens to hundreds of kilohertz. Thus, a branching event (nucleotide is temporarily incorporated, but then dissociates without the label being cleaved) could be distinguished from a true incorporation: a branching event will have the same slope (in a current vs. time graph) at the beginning and end of a pulse, whereas a true incorporation would have a steeper slope at the pulse end, when the free label diffuses away quickly.

Any suitable type of label (molecule, nanoparticle, quantum dot) of any shape (sphere, ellipsoid, pyramidal, etc.) that would yield a detectable change in the current signal could be used. Any shaped nanochannel could be used (conical, cylindrical, box-like, etc.). The polymerase could be in the middle of the nanochannel, at either entrance, or disposed at any suitable place within the nanochannel. See e.g. Williams et al. U.S. Pat. No. 7,625,701B2.

Attachment of Template to the Nanochannel

One aspect of the invention comprises performing nanopore sequencing in a system in which a template polymer is attached to the nanochannel. In one suggested method of nanopore DNA sequencing, see e.g. Clark et al., Nature Nanotechnology 4(4), 265-270 (2009), an exonuclease is coupled to a protein nanopore (e.g. alpha-hemolysin), either as a fusion protein or through a linker molecule. The exonuclease degrades double-stranded or single-stranded DNA base by base, and then an applied voltage pulls the diffusing dNMP through the nanopore (the exonuclease should be in close proximity to the mouth of the nanopore to decrease the likelihood that dNMPs will diffuse away). A drop in the current through the nanopore as dNMP passes through serves to identify the dNMP. It is challenging to create such a complex without compromising characteristics of the exonuclease, the protein nanopore, or both. Even with such a complex, read-lengths would generally be limited by the processivity of the exonuclease because the read ends once the exonuclease lets go of the template strand of DNA.

This aspect of the invention comprises a protein nanopore that has a linker molecule to attach dsDNA or ssDNA (see FIGS. 25A-D). For example, the protein nanopore can be fused to a streptavidin that will capture biotinylated DNA. Other DNA linking techniques known in the art can be used. In the method of this invention, an exonuclease can bind to the template DNA strand and begin cleaving off dNMPs, which are pulled by the applied potential through the protein nanopore. An advantage of this technique is an increase read-lengths beyond the processivity of the exonuclease, because if one exonuclease falls of the DNA template, the template is still bound to the same nanopore. Another exonuclease in the solution can then rebind the DNA template and sequencing can continue. Read-lengths are thus only limited by the length of the DNA template. Furthermore, a fusion/linked complex of exonuclease/protein nanopore does not have to be constructed.

Figure 25B:
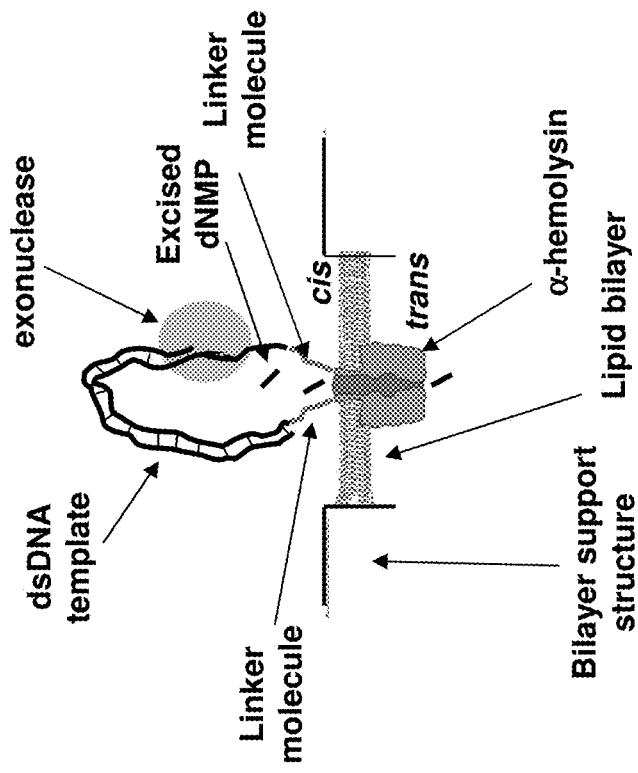
FIGS. 25A-25D each show a protein nanopore that has a linker molecule to attach DNA.
Figure 25A:
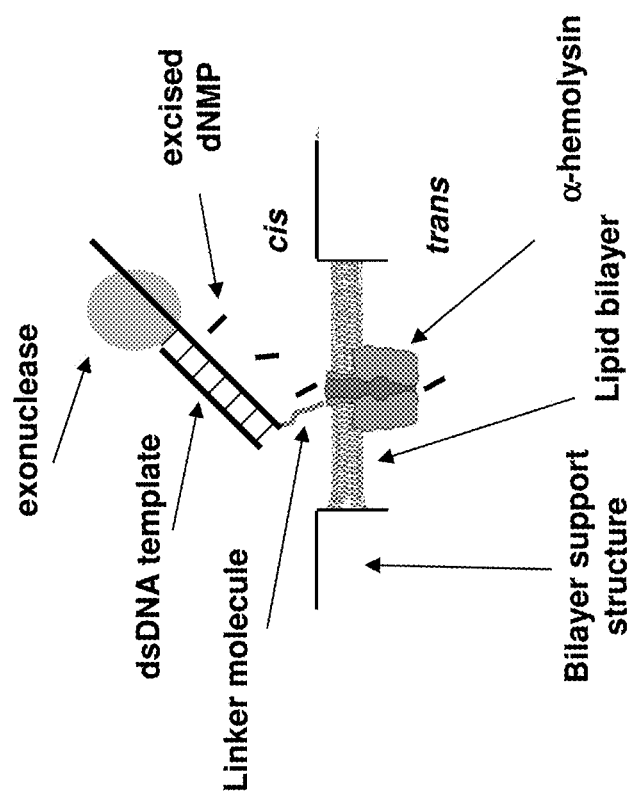
Figure 25D:
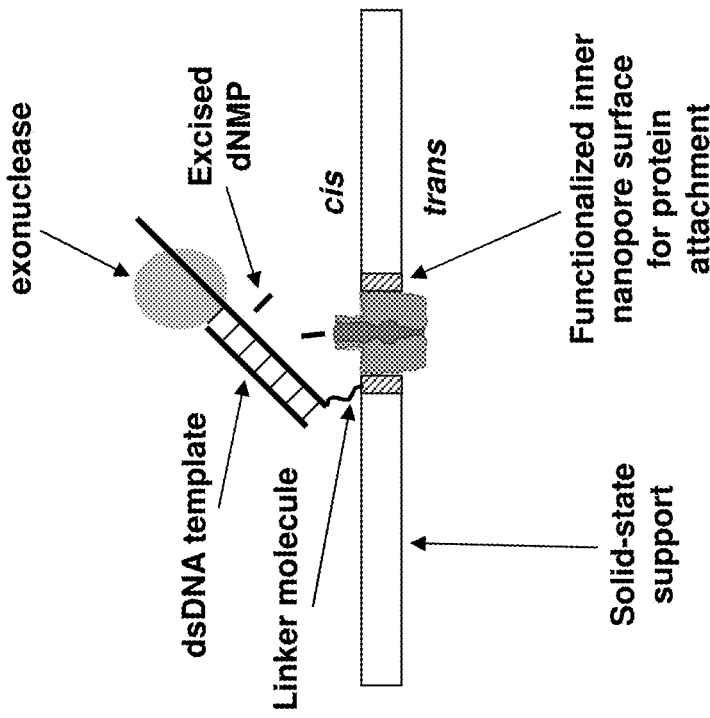
Figure 25C:
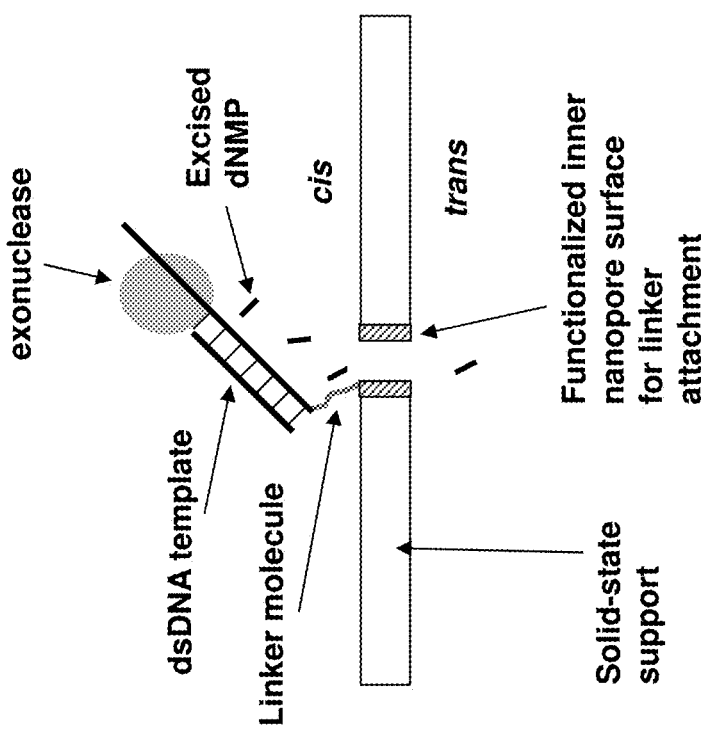

FIG. 25(A) shows a double stranded DNA template molecule attached to a protein nanopore held within a membrane. Here, an alpha hemolysin protein nanopore suspended in a lipid bilayer is used. In some cases the template nucleic acid will be a single stranded nucleic acid such as single stranded DNA. The template DNA is attached on the cis side of the nanopore with a linker, and the an exonuclease is acting on the template DNA to excise dNMPs. The excised dNTPs are driven through the nanopore and detected as they pass through the pore. Having the DNA template near the nanopore increases the likelihood that the dNMPs will be effectively transported through the nanopore. In FIG. 25(B), the DNA is attached to the nanopore in two locations on the DNA strand. Here, the template is a double-stranded DNA, and one of the strands is attached with linker to opposite sides of the nanopore by linker molecules; one linker attached to the 5' end and the other linker attached to the 3' end of the DNA strand. By attaching both ends of the template DNA, the dNMPs are excised near the nanopore throughout the exonuclease cleavage of the strand. Attachment at two locations on the DNA template can be useful for the sequencing of long DNA template molecules. FIG. 25(C) shows the attachment of the DNA template to a solid state nanopore. FIG. 25(D) shows the attachment of the DNA template to a hybrid solid state/protein nanopore.

While in this aspect of the invention the exonuclease may not be in as close proximity to the protein nanopore as it is were it fused or linked to the nanopore, it will generally be close enough. Due to the radius of gyration of DNA, a 250 bp DNA strand would be within ~35 nm of the pore entrance, and a 2.5 kbp DNA strand would be within ~120 nm of the pore entrance. In order to decrease the likelihood that dNMPs are lost in solution, the nanopore could be placed in a well, as described herein.

In some embodiments, both the exonuclease and the nucleic acid are tethered in close proximity to the nanopore. In order to allow for interaction between the bound species, one of the pair is attached such that it has enough mobility to diffuse into contact with the other. In some cases, one of the exonuclease or template is attached loosely, on a relatively long tether (e.g. a polyethylene glycol chain), and the other is attached more rigidly near the entrance of the pore. For example, in some embodiments, the exonuclease is bound so that it is held near the entrance to the pore, and the template nucleic acid is attached via linker molecule that allows it to diffuse into the exonuclease for reaction. Where the template nucleic acid is relatively long, and the distance between the attachment points of the exonuclease and the template proximate to the nanopore are close, the length and flexibility of the linker need not be as great.

In another embodiment, the template is anchored on both ends. This tends to keep the exonuclease close to the nanopore mouth. For example, if the template is dsDNA, then both ends could be biotinylated and fixed to one or more streptavidins flanking the nanopore. An example of a template anchored at both ends is shown in FIG. 25.

The attachment of the template can be utilized with a solid state nanopore, a protein nanopore, or a hybrid nanopore. The template DNA strand could also be attached to a hybrid protein/solid-state nanopore or to the functionalized edge of a solid-state nanopore. For example, a solid-state nanopore can be surrounded with an annulus of gold or small gold spheres, and a thiolated DNA template can be used to provide attachment for the template.

Methods for Multiple Pass Sequencing

Figure 26:
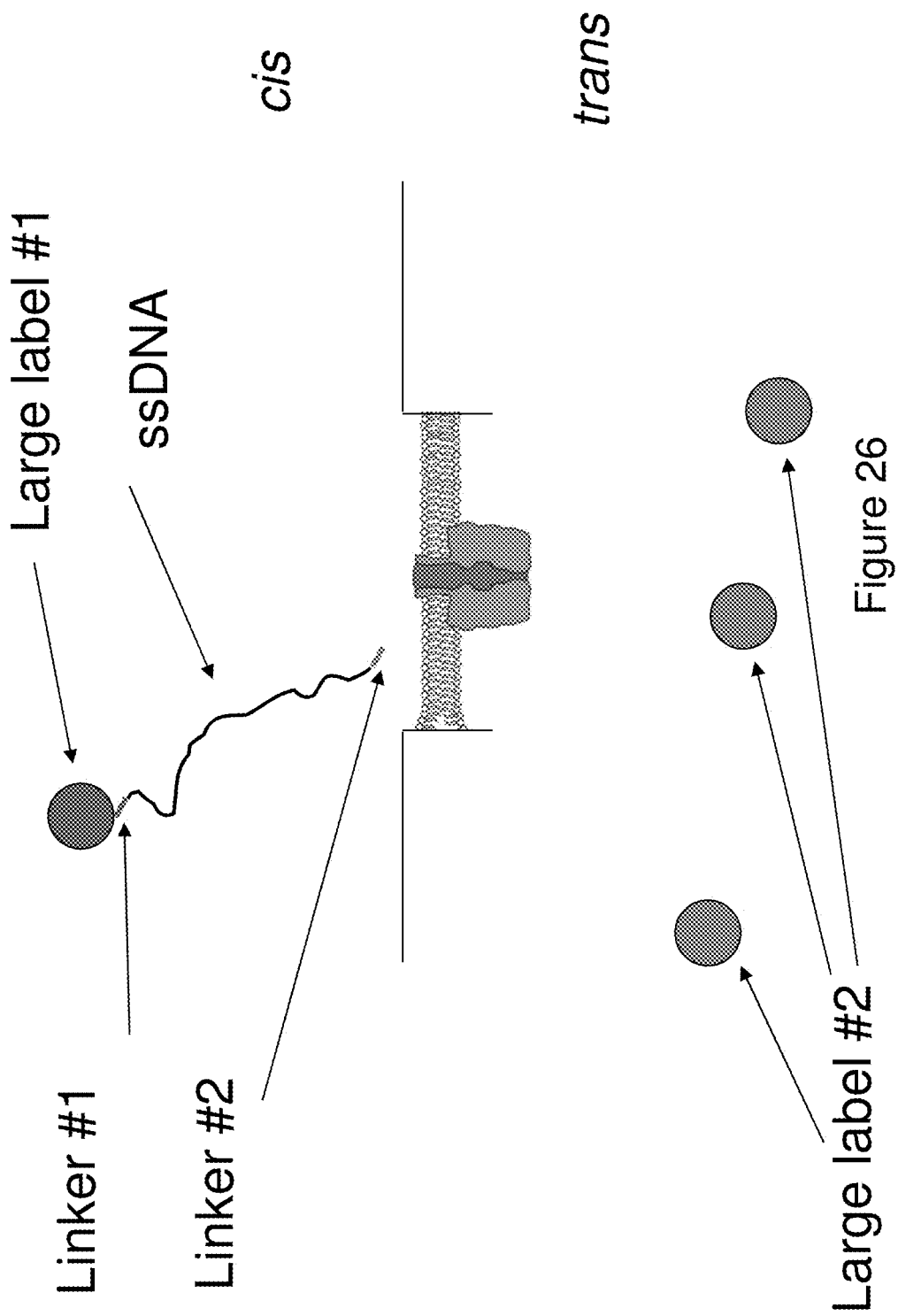
FIG. 26 shows a method for multi-pass sequencing.
Figure 27B:
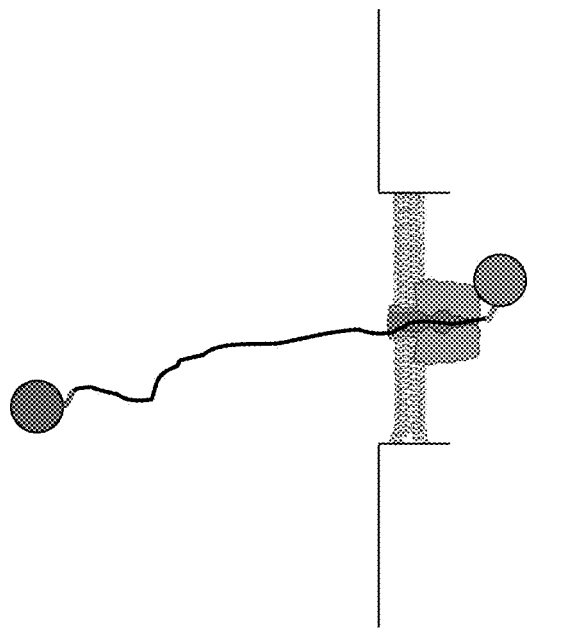
FIGS. 27A and 27B show drawing the DNA back and forth, while it is retained by the pore.
Figure 27A:
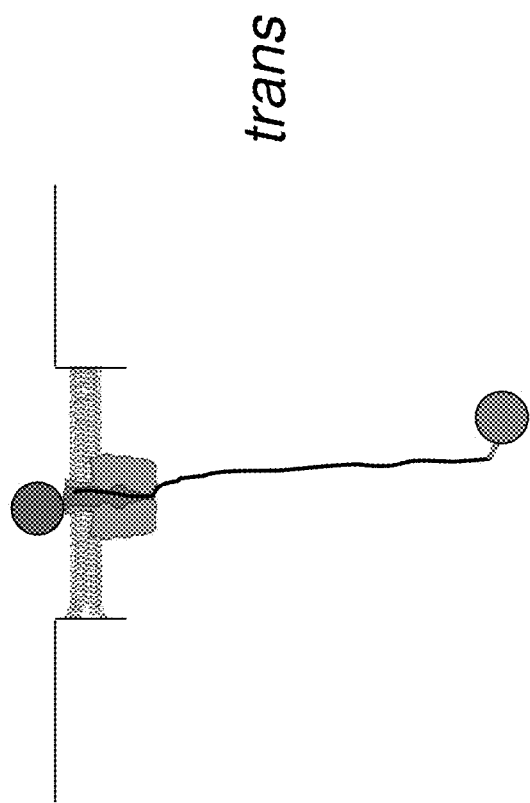

One aspect of the invention is a method for performing consensus nanopore sequencing of a single molecule of ssDNA. The method allows for a ssDNA molecule to be sequenced repeatedly, significantly improving the accuracy of nanopore sequencing. The method comprises the following steps: Step 1: start with solution of ssDNA to be sequenced, Step 2: attach a linker molecule (e.g. biotin) to 3' end of the ssDNA, Step 3: Conjugate to a large label (e.g. streptavidin) that cannot pass through the nanopore, Step 4: attach a linker molecule to 5' end of the ssDNA, Step 5: Add labeled ssDNA to cis side of nanopore. Apply potential difference across nanopore, which will electrophoretically draw one molecule of ssDNA at a time through nanopore, Step 6: trans side of nanopore should contain another large label (that specifically binds to the linker molecule on 5' end of ssDNA). Once the ssDNA begins passing through the nanopore, this large label attaches to the 5' end, Step 7: Sequence the ssDNA as it is drawn through the nanopore to the trans side, Step 8: When it reaches the end and gets trapped (can be detected by no change in current), reverse the potential. One can either sequence the ssDNA backwards, or one can push the ssDNA all the way back to the cis side and start over again, Step 9: When enough consensus sequences have been obtained, use standard biochemistry techniques (including pH or temperature changes, or photocleavage) to cleave labels from ssDNA and allow it to pass completely to trans side, Step 10: Start again with a new strand of ssDNA. The method is illustrated in FIG. 26 and FIG. 27.

In some embodiments, the 3' end could go through the nanopore first. Any suitable linker molecule that can be attached to the end of ssDNA could be used, along with any large particle/protein/molecule that will specifically attach to this linker and trap the ssDNA in the nanopore. In some cases, instead of using a linker/label to trap the ssDNA, one could simply hybridize complementary DNA to each end of the ssDNA to make it double-stranded (single dsDNA cannot pass through the nanopore). This method could be implemented by creating universal adapter sequences (e.g. polyA or polyT tails) at each end of the ssDNA.

Event Driven Detection

One aspect of the invention is a method for determining sequence information about a polymer molecule comprising: (a) obtaining a device having an array of nanopores, each connected to upper and lower fluid regions; wherein the device comprises electronic circuits electrically connected to electrodes in either the upper fluid regions or lower fluid regions or both the upper and lower fluid regions; (b) placing a polymer molecule in an upper fluid region; (c) applying a voltage across the nanopore whereby the polymer molecule is translocated through the nanopore; (d) using the electronic circuits to monitor the current through the nanopore over time, wherein the electronic circuits process the incoming current over time to record events, thereby generating event data; and (e) using the event data of step (d) to obtain sequence information about the polymer molecule.

In some cases the events comprise a change in current level above a specified threshold. In some cases the electronic circuit records the events, the average current before the events and the average current after the events.

In some cases the event data is generated without reference to time. In some cases a clock circuit is used such that the relative time that the events occurred is also determined.

In some cases the event data generated by the electronic circuits on the device is transmitted from the device for further processing. In some cases the information is transmitted optically.

Base Calling Methods

Figure 28:
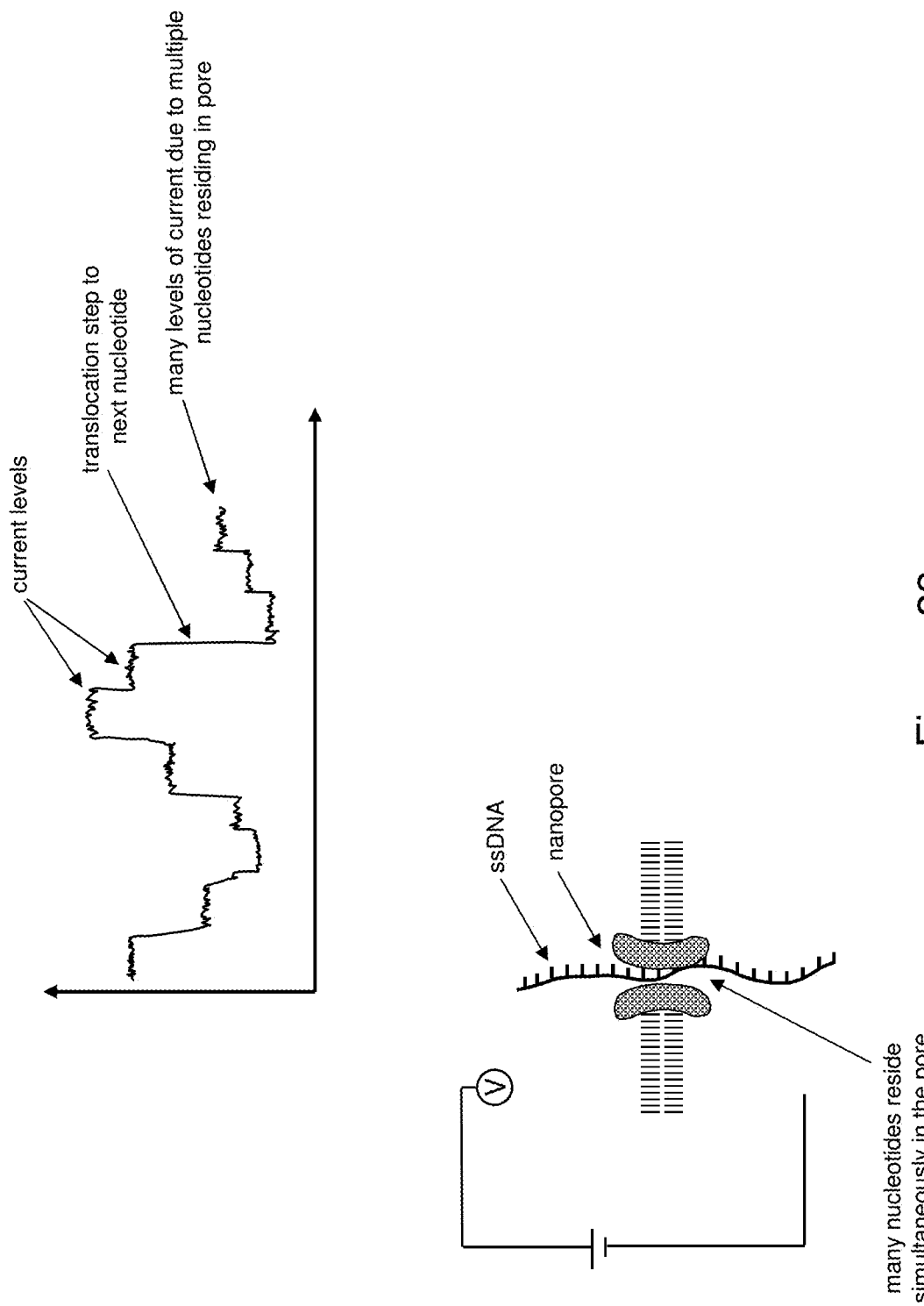
FIG. 28 shows current levels corresponding to different portions of a DNA strand passing through a nanopore.

Nanopore sequencing generally does not achieve single nucleotide resolution, especially in embodiments that might be scaled to a commercially viable DNA sequencing system. Rather, the amplitude of electric current passing through the nanopore (which constitutes the signal) depends on the identity of the several bases that reside in the pore throughout the duration of the current measurement. Thus, rather than there being 4 distinct current levels (for A,G,C,T) when the ssDNA translocates through the nanopore, there are 4 to the N levels (N=the number of bases that affect the current measurement), some of which may be degenerate (see FIG. 28). Furthermore, the bases residing in the center of the nanopore likely affect the current measurement more than those near the entrance or exit.

One aspect of the invention is a method for processing information from nanopore sequencing obtaining improved base calling. In some cases, the method will enable single base calling from raw data that in unprocessed form cannot call to the level of a single base. The invention involves deconvoluting the current measurements in order to achieve single nucleotide resolution. For example, if one knows that only 3 contiguous bases on the ssDNA strand determine the current measurement at any give time, then there are $4^3=64$ possible current levels (some of which might be degenerate). One embodiment involves synthetically creating 64 different ssDNA strands with all the possible 3-base combinations, and then pre-calibrating the system by measuring the current blockage levels from each of these ssDNA strands. Subsequent measurements on ssDNA in which the sequence is unknown are then compared to this pre-calibration measurement. In an alternative embodiment, the four current levels associated with 4 DNA homopolymers (e.g. AAA, GGG, CCC, TTT) are determined, allowing the amount by which each position contributes to the current level (e.g. by comparing AAA to TAA to AAT) to be derived. For example, where it is measured that the nucleotide in the center of the nanopore contributes to 75% of the current blockage, the previous nucleotide (−1) contributes 15%, and the subsequent nucleotide (+1) contributes 10%, then a deconvolution can be performed calculate the predicted current blockage from the various combinations, which can in turn be used to obtain the sequence on an unidentified ssDNA strand by measuring its current blockage.

Because the response time of the measurement system (enzyme plus electrical junction) can be slow in comparison to the single-nucleotide rate through the pore, the measure signal is a convolution of the current perturbation and a impulse function (hereafter called the base-spread function or "bsf"). Deconvolution of the observed signal which arises from convolution with a known kernel in the method of the invention can be done by, for example, Wiener deconvolution, Jansson deconvolution, or Richardson-Lucy deconvolution.

Basecalling such a signal requires the following steps: deconvolution, peak finding, and peak classification. A fourth optional step which is likely desirable is a quality estimation ("QV" estimation). Peak finding entails finding maximal points in the deconvolved signal which match the characteristics of known peaks (i.e. proper amplitude and width). An example of such an algorithm is a matched filter or derivative crossing algorithm. Peak classification can be approached by many different statistical classification algorithms such as heuristic decision-tree algorithms, Bayesian networks, hidden Markov models, and conditional random fields.

The application of a deconvolution algorithms generally assumes a known bsf with constant properties across the signal. The establishment of the form bsf can be identified from control sequence as described above.

Given the nature of single-molecule measurements it is highly likely that the bsf will vary from trace to trace and even within local regions of a given trace. This complicates the use of off-the-shelf deconvolution algorithms. Where the bsf changes on a relatively slow time scale then a windowed deconvolution can be applied by segmenting the signal first.

Windowed deconvolution is applied, for example, where we can estimate the bsf for each window. If we can rely on the kinetics of the signal having isolated peaks then the form of the bsf can be estimated by identifying such peaks in the signal. Alternatively a blind deconvolution technique can be applied, i.e. optimize the bsf across the window until the best contrast is obtained (similar to auto-focus or automated image restoration algorithms).

In addition, where resequencing is being performed, and the accuracy of any individual measurement is high, then in some cases, single base resolution is not required in order to align a measured sequence with the reference genome, and the known sequence information can be used in conjunction with these methods to improve accuracy. For example, the reference sequence can be convolved with the known bsf and the matching can be performed in the convolved space.

Figure 29:
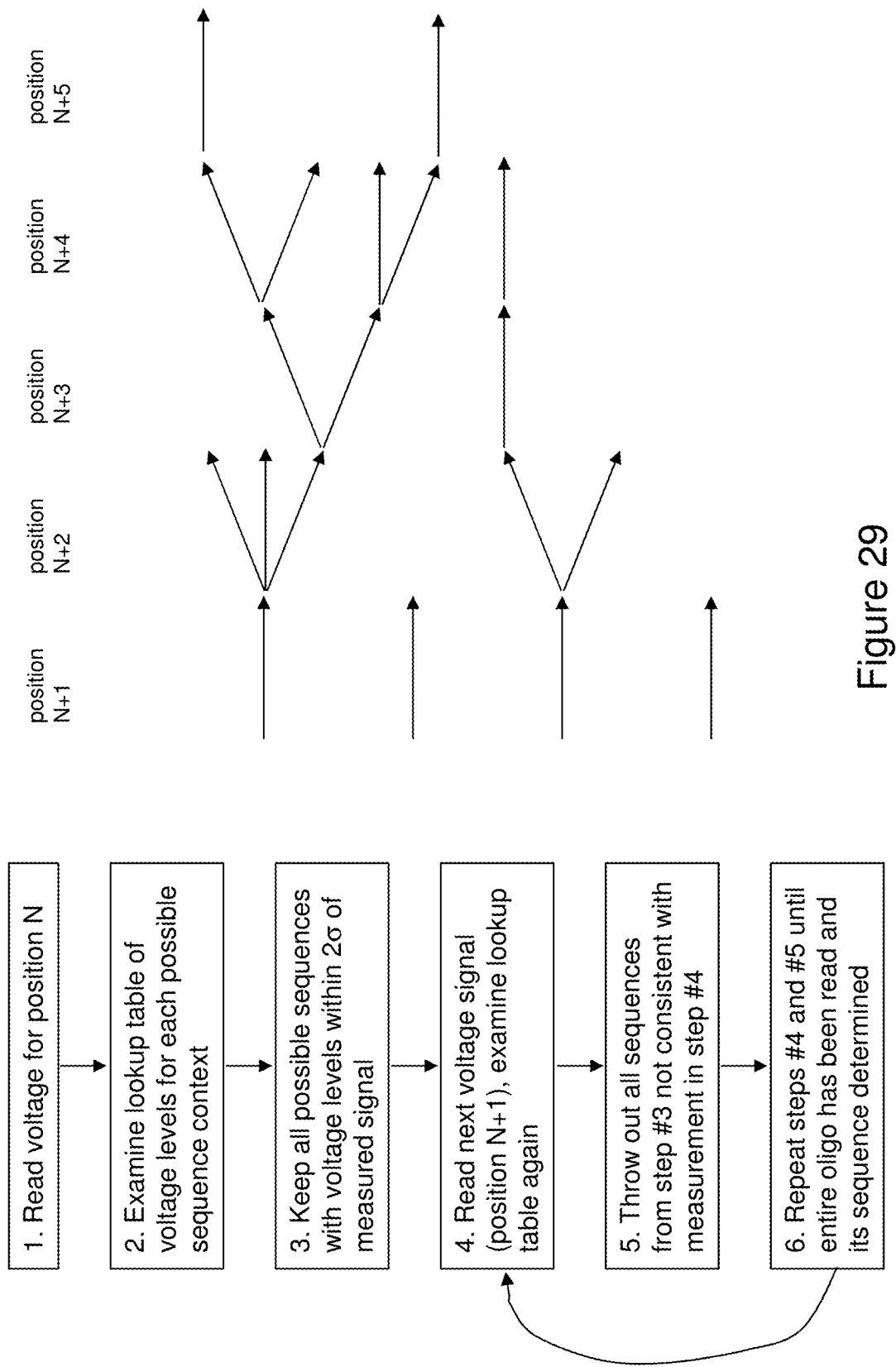
FIG. 29 shows an algorithm for using a lookup table for base calling.

When measuring the voltage and setting a threshold (e.g. 2 sigma) for comparison to a lookup table of all possible sequence context voltages, one might adjust this threshold or the baseline at each position in the template based on slow, global fluctuations (perhaps due to fluctuations in the power source); or based on a noise model indicating that this template region results in noisier signals; or based on fluctuating cross-talk noise from neighboring nanopores. An algorithm for using a lookup table in this manner is shown in FIG. 29.

One aspect of the invention is a method for determining the sequence of a polymer having two or more types of monomeric units in a solution comprising: (a) actively translocating the polymer through a pore; (b) measuring a property which has a value that varies depending on whether and which of the two or more a type of monomeric unit is in the pore, wherein the measuring is performed as a function of time, while the polymer is actively translocating; and (c) determining the sequence of the two or more types of monomeric units in the polymer using the measured property from step (b) by performing a process including the steps of: (i) deconvolution, (ii) peak finding, and (iii) peak classification.

In some cases the polymer is a nucleic acid, the monomeric units are nucleotide bases or nucleotide analogs, and the measured property is current. In some cases the deconvolution comprises (a) carrying out measurements of current as a function of time on nucleic acids having known sequences to produce calibration information, and (b) using the calibration information perform the deconvolution. In some cases deconvolution uses a Weiner, Jansson, or Richardson-Levy deconvolution.

In some cases the peak classification is performed by a heuristic tree algorithm, Bayesian network, hidden Markov model, or conditional random field. In some embodiments the method further comprises step (iv) of quality estimation.

In some cases the measurements are on nucleic acids having known sequences comprising known n-mers. In some cases the known n-mers are 3-mers, 4-mers, 5-mers or 6-mers.

In single-molecule nanopore sequencing based on exonuclease release of a base into a nanopore that separates two chambers with a voltage drop between them, three metrics include the amplitude of the current blockage (associated with numerous characteristics of the nucleotide, such as size and charge), the duration of the current blockage (associated with the nucleotide's interaction with the inside of the pore), and the interpulse duration (associated with the dead-time in between exonuclease events). One aspect of the invention is algorithms for combining information about these three metrics to determine the identity of a base.

In single-molecule nanopore sequencing based on exonuclease release, generally only one current reading is obtained per nucleotide that flows through the nanopore. Thus, if the probability distribution of current blockage (likely Gaussian-like) for a nucleotide is highly overlapping with that of a different nucleotide, then there may be a large probability of miscall if only this metric is used. One can combine this information with information from the probability distribution of current blockage duration (likely exponential-like) for each nucleotide. In one algorithm of the invention, one takes the measurements of current blockage amplitude and current blockage duration, computes a probability of nucleotide-identity for each metric (based on previously calibrated experiments and determination of the probability distributions), and adds these probabilities in quadrature to obtain an overall probability of nucleotide-identity. For example, if $P_A(\text{duration})=x$, and $P_A(\text{amplitude})=y$, then $P_A(\text{overall})=\sqrt{\{x^2+y^2\}}$.

Alternatively, one could weight the metrics depending on their relative importance or relative uncertainty. Thus, if one placed an importance of q on pulse duration, then $P_A(\text{overall})=\sqrt{\{q*x^2+(1-q)*y^2\}}$. In the case of an exonuclease chewing up dsDNA, the interpulse duration likely depends on the sequence context and the secondary structure of the DNA. The measurement of interpulse duration could be added into the quadrature computation, e.g. $P_A(\text{interpulse duration})=z$ and $P_A(\text{overall})=\sqrt{\{x^2+y^2+z^2\}}$ or with appropriate weighting.

A second algorithm uses the probability of base-identity obtained from one metric to alter the probability distribution of a second metric, after which the altered probability distribution the second metric is used to call the base. For example, Base 1 and Base 2 have overlapping current blockage amplitude probability distributions (call them P1 and P2). Once the current blockage duration is measured and compared against the probability distribution of the current blockage duration, one can create a new current blockage amplitude probability distributions for each base, call P1' and P2'. If the current blockage duration measurement was more likely to come from Base 1, then P1' would be wider than P1, and P2' would be narrower than P2, but the area under each distribution would remain the same. Thus, the overlap between P1' and P2' is different from the overlap between P1 and P2. One then uses P1' and P2' and the current blockage amplitude measurement to identify the unknown nucleotide. In a similar manner, the information from the interpulse duration measurement could also be used to alter P1' and P2' and obtain P1" and P2".

Dynamic Interventional Nanopore Sequencing

One aspect of the invention involves dynamically reversing the driving field in order to obtain repeated reads of the same sequence to improve accuracy. In embodiments of sequencing in which ssDNA is electrophoretically drawn through a nanopore (either solid-state or protein), low inherent base calling accuracy can be a problem. For example, if the rate of translocation of each nucleotide through the nanopore follows an exponential distribution, there will be many fast translocation events that will lead to low SNR event measurements. Furthermore, the current blockage levels of each of the four nucleotides will likely have overlapping distributions, leading to the possibility of miscall errors. A method of real-time re-sequencing of ssDNA regions in which low accuracy is suspected would greatly improve the overall accuracy of nanopore sequencing.

Where ssDNA is electrophoretically drawn through a nanopore—from the cis chamber to the trans chamber, applying a reverse potential can move the ssDNA backwards—from the trans chamber toward the cis chamber. Reversing the potential in real time when, for example, a suspicious base call is made can enable an additional measurement of that region of the nucleotide. For example, an algorithm could automatically reverse the potential if the following events are detected: 1. A very short duration current pulse is detected, which likely has low signal-to-noise, 2. A current pulse's amplitude is in between the peaks of the distributions for two different bases, in which case the probability of a miscall is high, 3. An unusually long pulse (indicated the possible existence of homopolymers, which could lead to deletion or insertion errors), 4. The time in between two pulses is unusually long, implying a large likelihood of a miscall. or 5. There is more noise than usual at this template position (due to a drift in the baseline, due to stochastic cross-talk from neighboring nanopores, or due to sequence context).

The invention involves dynamically controlling the applied potential in order to enable re-sequencing of low-accuracy regions of the ssDNA. One embodiment involves training the basecaller on known ssDNA templates in order to improve its ability to detect low-accuracy regions.

Figure 30:
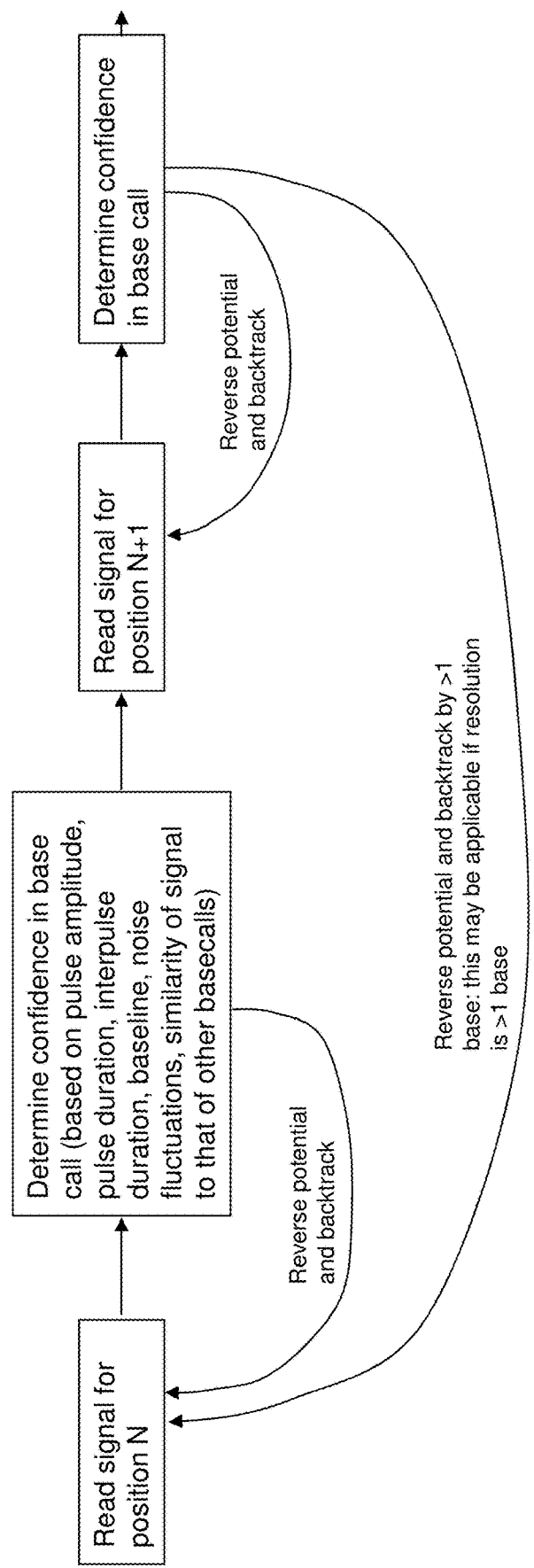
FIG. 30 provides a flow chart illustrating dynamic interventional nanopore sequencing.

In some cases, when reversing the potential, the reverse current could be measured, in order to measure the sequence in the reverse direction while the ssDNA is moving backwards. In addition, when switching the potential back to its normal sign (i.e. reversing the reversed potential), one could lower the amplitude of the voltage in order to draw the ssDNA through the nanopore more slowly to enable a higher SNR read of the suspicious nucleotide. In some cases, the potential could be reversed with an amplitude/duration such that only 1 nucleotide is re-sequenced, or more than one nucleotide is resequenced. A flow chart illustrating is method is shown in FIG. 30.

In order to practice dynamic intervention, it is important that the capacitance of the system be in a suitable range in order to allow reversal of the current at the required frequency. We have determined that in some embodiments, where the electrical resistance across the nanopore is about 5 giga-ohms, the capacitance should be less than about 3.2 fF in order to have a response time of 0.1 ms. For a resistance of 5 giga-ohms and a response time of about 1 ms the capacitance should be less than about 32 fF. For a resistance of 5 giga-ohms and a response time of about 10 ms the capacitance should be less than about 320 fF. For a resistance of 5 giga-ohms and a response time of about 0.01 ms the capacitance should be less than about 0.32 fF. Thus, for use with dynamic intervention, the nanopore structures are produced to have a capacitance that falls in this range or lower. The capacitance of the nanopore structures can be lowered, for example, by controlling the geometry of the structures that make up the nanopore, and by controlling the materials that comprise the nanopore structure. In some cases, the hybrid nanostructures described herein can produce lower capacitance nanopore structures by minimizing the amount of or by eliminating the area of lipid bilayer surrounding the nanopore.

In some embodiments, the capacitance of a nanopore structure comprising a phospholipid bilayer is lowered by incorporating non-conductive transmembrane proteins. The transmembrane proteins can have the effect of increasing the thickness of the bilayer, and the increase in thickness can result in a lowering of the capacitance of the bilayer and therefore the nanopore structure. The non-conductive transmembrane protein can any suitable protein including plugged nanopore proteins or transmembrane signaling proteins. The proteins can be fusion proteins having some portions that are membrane soluble and other portions that are water soluble. The relative size of the portions can be controlled to control the properties of the membrane layer. Magnetic Particles for Control of Polymer Translocation One aspect of the invention involves the use of magnetic particles that are associated with the pore or membrane the pore resides in. The magnetic particle's movement could be controlled by magnetic fields, which would have little effect on the rest of the system, as most biologically relevant molecules are not sensitive to magnetic fields.

In one embodiment the magnetic particle is tethered to the nanopore close to the entry point of the polymer. Without a magnetic field, this particle would be free to float around the polymer, and would not tend to inhibit its motion through the pore (FIG. 31(a)). When a magnetic field is applied the particle is pulled in a direction that results in the complete or partial plugging the pore, or in pinning of the polymer (FIG. 31(b)).

Similar pore regulations mechanism exist naturally, and have been referred to as "Ball and Chain" pore regulators. See, e.g. Jiang et al. Nature, Vol. 417, 523-526, 2002.

In some cases, by controlling the field strength and makeup of the device, pinning the biopolymer to the pore can sufficiently slow the movement through the pore. In some cases, a lock step movement can be created, for example, using a pulsed magnetic field. A pulsed magnetic field may allow the particle to pin-release-pin the biopolymer allowing for further controlling translocation rates and detection times. In addition, the magnetic particle may be used to change the overall electrical characteristics of the pore, such that one can read out when the biopolymer is pinned, and when it is not.

In other embodiments, magnetic particles can exert a force to control pore characteristics. For example, a magnetic force can cause the natural pore opening to change in size or shape (FIG. 31(c)). In addition, the magnetic particle can influence the shape of the membrane the nanopore is embedded in, thus influencing shape/size of the nanopore indirectly. (FIG. 31(d)).

EXAMPLES

Example 1: Sequencing with Polymerase Enzyme in Nanochannel—SiN

In one embodiment, an array of 256×256 nanochannels, each with approximate dimensions 100-nm×40-nm×40-nm, are fabricated in a silicon nitride (SIN) substrate using techniques well-known in the art. While surfaces outside the nanochannels are passivated with an inert polymer, such as PEG, the inner surface of each channel is modified with biotinylated silane using techniques well-known in the art. A ϕ29 DNA polymerase, modified to have a C- or N-terminal biotin tag, is conjugated to streptavidin. A DNA template, e.g. a cyclic DNA template such as a SMRTbell (Pacific BioSciences) with a primer, is captured by the polymerase. This streptavidin/polymerase/DNA complex is then loaded onto the nanochannel array at a concentration and for a duration such that ~37% nanochannels contain only a single complex (Poisson loading). The nanochannels are bathed in a solution containing the necessary components for both DNA synthesis by the polymerase (e.g. metal ion, four nucleotide analogs, etc.) and for current flow through the channel (e.g. salt). A voltage of ~100-800 mV is applied across the nanochannels. The nucleotide analogs are labeled at their terminal-phosphate with a latex particle. Each of the four analogs types, corresponding to the four nucleotides, is labeled with a different sized latex particle (e.g. 10-nm, 15-nm, 20-nm, 25-nm diameters). While the cognate nucleotide is being incorporated by the polymerase into the growing strand complementary to the DNA template, the label alters the current flowing through the nanochannel. Each type of label alters the current in a way distinct from the other labels, and thus the identity of the incorporated base is determined. As a natural part of the incorporation process, the polymerase cleaves the label from the nucleotide, allowing the growing DNA strand to be label-free.

Example 2: Sequencing with Polymerase Enzyme in Nanochannel—SiOx

In another embodiment, an array of 256×256 nanochannels, each with approximate dimensions 100-nm×40-nm×40-nm, are fabricated in a silicon oxide (SiOx) substrate using techniques well-known in the art. While surfaces outside the nanochannels are passivated with an inert polymer, such as PEG, the inner surface of each channel is modified with biotinilated silane using techniques well-known in the art. A $\phi$29 DNA polymerase, modified to have a C- or N-terminal biotin tag, is conjugated to streptavidin. A DNA template, e.g. a cyclic DNA template such as a SMRTbell (Pacific BioSciences) with a primer, is captured by the polymerase. This streptavidin/polymerase/DNA complex is then loaded onto the nanochannel array at a concentration and for a duration such that ~37% nanochannels contain only a single complex (Poisson loading). The nanochannels are bathed in a solution containing the necessary components for both DNA synthesis by the polymerase (e.g. metal ion, four nucleotide analogs, etc.) and for current flow through the channel (e.g. salt). A voltage of ~100-800 mV is applied across the nanochannels. The nucleotide analogs are labeled at their terminal-phosphate with a latex particle. Each of the four analogs types, corresponding to the four nucleotides, is labeled with a different sized latex particle (e.g. 10-nm, 15-nm, 20-nm, 25-nm diameters). While the cognate nucleotide is being incorporated by the polymerase into the growing strand complementary to the DNA template, the label alters the current flowing through the nanochannel. Each type of label alters the current in a way distinct from the other labels, and thus the identity of the incorporated base is determined. As a natural part of the incorporation process, the polymerase cleaves the label from the nucleotide, allowing the growing DNA strand to be label-free.

Example 3: Sequencing with Polymerase Enzyme in Nanochannel—Polymeric Substrate

In another embodiment, an array of 256×256 nanochannels, each with approximate dimensions 100-nm×40-nm×40-nm, are fabricated in a polymeric substrate with backbone containing thiol-acrylate using techniques well-known in the art. While surfaces outside the nanochannels are passivated with an inert polymer, such as PEG, the inner surface of each channel is modified with biotinylated maleimide using techniques well-known in the art. A $\phi$29 DNA polymerase, modified to have a C- or N-terminal biotin tag, is conjugated to streptavidin. A DNA template, e.g. a cyclic DNA template such as a SMRTbell (Pacific BioSciences) with a primer, is captured by the polymerase. This streptavidin/polymerase/DNA complex is then loaded onto the nanochannel array at a concentration and for a duration such that ~37% nanochannels contain only a single complex (Poisson loading). The nanochannels are bathed in a solution containing the necessary components for both DNA synthesis by the polymerase (e.g. metal ion, four nucleotide analogs, etc.) and for current flow through the channel (e.g. salt). A voltage of ~100-800 mV is applied across the nanochannels. The nucleotide analogs are labeled at their terminal-phosphate with a latex particle. Each of the four analogs types, corresponding to the four nucleotides, is labeled with a different sized latex particle (e.g. 10-nm, 15-nm, 20-nm, 25-nm diameters). While the cognate nucleotide is being incorporated by the polymerase into the growing strand complementary to the DNA template, the label alters the current flowing through the nanochannel. Each type of label alters the current in a way distinct from the other labels, and thus the identity of the incorporated base is determined. As a natural part of the incorporation process, the polymerase cleaves the label from the nucleotide, allowing the growing DNA strand to be label-free.

Example 4: Sequencing with Polymerase Enzyme in Nanochannel—SiN and Silica Particles on Nucleotides In another embodiment, an array of 256×256 nanochannels, each with approximate dimensions 100-nm×40-nm×40-nm, are fabricated in a SiN substrate using techniques well-known in the art. While surfaces outside the nanochannels are passivated with an inert polymer, such as PEG, the inner surface of each channel is modified with biotinilated silane using techniques well-known in the art. A $\phi$29 DNA polymerase, modified to have a C- or N-terminal biotin tag, is conjugated to streptavidin. A DNA template, e.g. a cyclic DNA template such as a SMRTbell (Pacific BioSciences) with a primer, is captured by the polymerase. This streptavidin/polymerase/DNA complex is then loaded onto the nanochannel array at a concentration and for a duration such that ~37% nanochannels contain only a single complex (Poisson loading). The nanochannels are bathed in a solution containing the necessary components for both DNA synthesis by the polymerase (e.g. metal ion, four nucleotide analogs, etc.) and for current flow through the channel (e.g. salt). A voltage of ~100-800 mV is applied across the nanochannels. The nucleotide analogs are labeled at their terminal-phosphate with a latex particle. Each of the four analogs types, corresponding to the four nucleotides, is labeled with a different sized silica particle (e.g. 10-nm, 15-nm, 20-nm, 25-nm diameters). While the cognate nucleotide is being incorporated by the polymerase into the growing strand complementary to the DNA template, the label alters the current flowing through the nanochannel. Each type of label alters the current in a way distinct from the other labels, and thus the identity of the incorporated base is determined. As a natural part of the incorporation process, the polymerase cleaves the label from the nucleotide, allowing the growing DNA strand to be label-free.

Example 5: Simulation Demonstrating Base Calling Using Signals Characteristic of More than One Base to Call Bases at Single Base Resolution A simulation was performed that demonstrated the ability to determine the identity of a DNA sequence as it translocates through a nanopore, given that the resolution of the measurement system is >1 nucleotide (i.e. the measurement is influenced by the identity and position of a number of nucleotides, e.g. 5 that reside within the nanopore at any given moment). The algorithm uses a lookup table as shown in FIG. 29. The algorithm is for use with a lookup table created for the signals yielded by every possible permutation of the several bases that affect the measurement. Some of these signals will be degenerate with one another within the error of the measurement. Given a measurement, this algorithm compares the signal with the lookup table and keeps track of all the possible 5-mers that could account for the measurement.

After each single-nucleotide translocation through the nanopore, the algorithm looks up the possible 5-mers for that measurement and then throws away all the possibilities from the previous measurement that are not consistent with the most recent measurement. Thus, even if the first measurement yielded many possible sequences, it is likely that after several measurements there will only be one or a few possible sequences that are consistent with all the measurements (this will depend on the distribution of voltages in the lookup table and on the accuracy of the measurements).

The above description is intended to be illustrative and not restrictive. It readily should be apparent to one skilled in the art that various embodiments and-modifications may be made to the invention disclosed in this application without departing from the scope and spirit of the invention. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated by reference in its entirety for all purposes.

What is claimed is:

1. A method for sequencing a nucleic acid using a nanopore comprising:
   providing a substrate having an upper solution above the substrate and a lower solution below the substrate, the substrate comprising a nanopore connecting the upper solution and lower solution, the nanopore sized to pass a single stranded nucleic acid;
   providing a voltage across the nanopore to produce a measurable current flow through the nanopore;
   providing a polymerase-nucleic acid complex comprising a strand displacing DNA polymerase and a circular nucleic acid template and providing the components required for DNA synthesis whereby the polymerase produces a nascent DNA strand which is translocated through the nanopore while the nascent DNA strand is produced;
   measuring the current through the nanopore over time as the nascent strand is translocated through the nanopore;
   determining a sequence of the nascent DNA strand as it translates through the pore using the measured current over time, whereby the polymerase proceeds around the circular template, then continues to produce the nascent DNA strand such that a sequence in the nascent DNA strand corresponding a sequence in the circular template is determined more than once.

2. The method of claim 1 wherein the DNA polymerase is tethered to the nanopore.

3. The method of claim 2 wherein the DNA polymerase is covalently tethered.

4. The method of claim 2 wherein the DNA polymerase is non-covalently tethered.

5. The method of claim 1 wherein the DNA polymerase comprises a phi29 DNA polymerase, a T7 DNA pol, a T4 DNA pol, an *E. coli* DNA pol 1, or a Klenow fragment.

6. The method of claim 1 wherein the DNA polymerase comprises a phi29 DNA polymerase.

7. The method of claim 1 wherein the nanopore is a solid state nanopore.

8. The method of claim 1 wherein the nanopore is a hybrid solid state-protein nanopore.

9. The method of claim 1 wherein the nanopore is a protein nanopore.

10. The method of claim 1 wherein the nanopore comprises alpha-hemolysin or MspA.

11. The method of claim 1 wherein transverse tunneling current across the nanopore is measured.

12. The method of claim 1 wherein current blockage is measured.

13. The method of claim 1 wherein the translocation rate of the DNA is controlled by the concentration of a reactant or cofactor.

14. The method of claim 1 wherein the translocation rate of DNA is controlled by the concentration of nucleotides or metal cofactors.

15. The method of claim 1 wherein the kinetics of the polymerase are altered to improve sequence detection.

16. The method of claim 15 wherein the kinetics are altered by mutations.

17. The method of claim 1 wherein both DC and AC drive voltages are applied.

18. The method of claim 1 wherein measuring of the sequence more than once allows for error correction.

19. The method of claim 1 wherein the signal from N-mers within the pore are used to determine the sequence of the DNA strand wherein N is three or greater.

20. The method of claim 19 wherein the N-mers are 4-mers.

21. The method of claim 19 wherein the N-mers are 5-mers.

22. The method of claim 19 wherein the N-mers are 6-mers.

23. The method of claim 19 wherein the N-mers include 4-mers.

24. The method of claim 19 wherein the N-mers include 5-mers.

25. The method of claim 19 wherein the N-mers include 6-mers.

26. The method of claim 1 wherein the substrate comprises a semiconductor chip comprising an array of nanopores.

* * * * *